United States Patent
Wall et al.

(10) Patent No.: US 12,139,529 B2
(45) Date of Patent: Nov. 12, 2024

(54) ANTIBODY-PEPTIDE FUSION PROTEINS FOR TREATING AMYLOID DISORDERS

(71) Applicants: UNIVERSITY OF TENNESSEE RESEARCH FOUNDATION, Knoxville, TN (US); Attralus, Inc., San Francisco, CA (US)

(72) Inventors: Jonathan S. Wall, Knoxville, TN (US); James S. Foster, Knoxville, TN (US); Spencer Guthrie, San Francisco, CA (US); Jaume Pons, San Francisco, CA (US); Michael L. Klein, San Francisco, CA (US)

(73) Assignees: UNIVERSITY OF TENNESSEE RESEARCH FOUNDATION, Knoxville, TN (US); ATTRALUS, INC., Burlingame, CA (US)

( * ) Notice: Subject to any disclaimer, the term of this patent is extended or adjusted under 35 U.S.C. 154(b) by 0 days.

(21) Appl. No.: 18/298,953

(22) Filed: Apr. 11, 2023

(65) Prior Publication Data

US 2023/0416347 A1    Dec. 28, 2023

Related U.S. Application Data

(63) Continuation of application No. PCT/US2022/072413, filed on May 18, 2022.

(60) Provisional application No. 63/190,191, filed on May 18, 2021.

(51) Int. Cl.
*C07K 16/18* (2006.01)
*A61K 51/10* (2006.01)
*C07K 14/00* (2006.01)

(52) U.S. Cl.
CPC .......... *C07K 16/18* (2013.01); *A61K 51/1093* (2013.01); *C07K 14/001* (2013.01); *C07K 2317/77* (2013.01); *C07K 2317/92* (2013.01); *C07K 2319/30* (2013.01)

(58) Field of Classification Search
CPC .. C07K 16/18; C07K 14/001; C07K 2317/92; C07K 2317/77; C07K 2319/30; A61K 51/1093
See application file for complete search history.

(56) References Cited

U.S. PATENT DOCUMENTS

| | | |
|---|---|---|
| 4,816,567 A | 3/1989 | Cabilly |
| 5,545,806 A | 8/1996 | Lonberg |
| 5,545,807 A | 8/1996 | Surani et al. |
| 5,569,825 A | 10/1996 | Lonberg |
| 5,625,126 A | 4/1997 | Lonberg |
| 5,633,425 A | 5/1997 | Lonberg |
| 5,648,237 A | 7/1997 | Carter |
| 5,661,016 A | 8/1997 | Lonberg |
| 5,789,199 A | 8/1998 | Joly |
| 5,840,523 A | 11/1998 | Simmons |
| 5,959,177 A | 9/1999 | Hein |
| 6,040,498 A | 3/2000 | Stomp |
| 6,075,181 A | 6/2000 | Kucherlapati |
| 6,150,584 A | 11/2000 | Kucherlapati |
| 6,180,370 B1 | 1/2001 | Queen et al. |
| 6,417,429 B1 | 7/2002 | Hein |
| 6,420,548 B1 | 7/2002 | Vezina |
| 6,982,321 B2 | 1/2006 | Winter |
| 7,087,409 B2 | 8/2006 | Barbas, III |
| 7,125,978 B1 | 10/2006 | Vezina |
| 8,105,594 B2 | 1/2012 | Solomon et al. |
| 8,808,666 B2 | 8/2014 | Wall et al. |
| 9,683,017 B2 | 6/2017 | Wall et al. |
| 10,046,050 B2 | 8/2018 | Wall et al. |
| 10,213,506 B2 | 2/2019 | Wall et al. |
| 10,308,685 B2 | 6/2019 | Wall et al. |
| RE47,838 E | 2/2020 | Wall et al. |
| 11,530,257 B2 | 12/2022 | Jones et al. |
| 12,030,934 B2 | 7/2024 | Wall |
| 2010/0322932 A1 | 12/2010 | Solomon et al. |
| 2014/0079691 A1 | 3/2014 | Mcconnell et al. |
| 2016/0016999 A1 | 1/2016 | Wall et al. |
| 2019/0038745 A1 | 2/2019 | Lentzsch |
| 2019/0070285 A1 | 3/2019 | Martin et al. |
| 2019/0083616 A1 | 3/2019 | Wall et al. |
| 2019/0352383 A1 | 11/2019 | Chakravarthy et al. |
| 2020/0002410 A1 | 1/2020 | Lentzsch et al. |
| 2022/0411489 A1 | 12/2022 | Wall et al. |
| 2023/0265178 A1 | 8/2023 | Wall et al. |

FOREIGN PATENT DOCUMENTS

| | | |
|---|---|---|
| WO | 199110741 A1 | 7/1991 |
| WO | 199515982 A2 | 6/1995 |
| WO | 1996033735 A1 | 10/1996 |
| WO | 1996034096 A1 | 10/1996 |

(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Ailles, L. et al. (Oct. 1993). "Induction of Perlecan Gene Expression Precedes Amyloid Formation During Experimental Murine AA Amyloidogenesis," Laboratory Investigation 69(4):443-448.
Almagro, J.C. et al. (Jan. 1, 2008). "Humanization of Antibodies," Frontiers in Bioscience 13:1619-1633.
Altschul, S.F. et al. (Oct. 5, 1990). "Basic Local Alignment Search Tool," J. Mol. Biol. 215(3):403-410.
Ancsin, J.B. (2003, e-pub. Jul. 6, 2009). "Amyloidogenesis: Historical and Modern Observations Point to Heparan Sulfate Proteoglycans as a Major Culprit," Amyloid 10(2):67-79.

(Continued)

*Primary Examiner* — Olga N Chernyshev
(74) *Attorney, Agent, or Firm* — MORRISON & FOERSTER LLP

(57) ABSTRACT

Provided herein are antibody-peptide fusion proteins comprising an amyloid-reactive peptide linked to an antibody. Also provided herein are methods of treating amyloid-based diseases by administering an antibody-peptide fusion protein.

9 Claims, 27 Drawing Sheets

Specification includes a Sequence Listing.

(56) References Cited

FOREIGN PATENT DOCUMENTS

| | | | |
|---|---|---|---|
| WO | 1998024893 | A2 | 6/1998 |
| WO | 1998024893 | A3 | 8/1998 |
| WO | 199960024 | A1 | 11/1999 |
| WO | 2003074567 | A2 | 9/2003 |
| WO | 2008091954 | A2 | 7/2008 |
| WO | 2016032949 | A1 | 3/2016 |
| WO | 2019006062 | A1 | 1/2019 |
| WO | 2019241216 | A1 | 12/2019 |
| WO | 2021097360 | A1 | 5/2021 |
| WO | 2022246433 | A1 | 11/2022 |

OTHER PUBLICATIONS

Boerner, P. et al. (Jul. 1, 1991). "Production of a Antigen-Specific Human Monoclonal Antibodies from In Vitro-Primed Human Splenocytes," J. Immunol. 147(1):86-95.

Bowie, J.U. et al. (Jul. 12, 1991). "A Method to Identify Protein Sequences That Fold Into a Known Three-Dimensional Structure," Science 253(5016):164-170.

Brüggemann, M. et al. (1993). "Designer Mice: The Production of Human Antibody Repertoires in Transgenic Animals," Year in Immuno. 7:33-40.

Buck, F.S. et al. (Jul. 1989). "Ethnic Distribution of Amyloidosis: An Autopsy Study," Modern Pathology 2(4):372-377.

Charlton, K.A. (2004). "Expression and Isolation of Recombinant Antibody Fragments in E. coli," Methods Mol Biol 248:245-254.

Chothia, C. et al. (1987). "Canonical Structures for the Hypervariable Regions of Immunoglobulins," J. Mol. Biol. 196:901-917.

Clackson, T. et al. (Aug. 15, 1991). "Making Antibody Fragments Using Phage Display Libraries," Nature 352:624-628.

Cole, S.P.C. et al. (1985). "The EBV-Hybridoma Technique and Its Applicaton to Human Lung Cancer," in Monoclonal Antibodies and Cancer Therapy, Alan R. Liss, p. 77-96.

Comenzo, R.L. et al. (Jun. 15, 2002). "Autologous Stem Cell Transplantation for Primary Systemic Amyloidosis," Blood, The Journal of the American Society of Hematology 99(12):4276-4282.

Corpet, F. (Nov. 25, 1988). "Multiple Sequence Alignment With Hierarchical Clustering," Nucleic Acids Res. 16(22):10881-10890.

De Lorenzi, E. et al. (2004). "Pharmaceutical Strategies Against Amyloidosis: Old and New Drugs in Targeting a "Protein Misfolding Disease"," Current Medicinal Chemistry 11(8):1065-1084.

Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.

Fishwild, D.M. et al. (Jul. 1996). "High-Avidity Human IgGκ Monoclonal Antibodies from a Novel Strain of Minilocus Transgenic Mice," Nature Biotechnol. 14:845-851.

Gertz, M.A. et al. (Jul. 7, 2020). "Systemic Amyloidosis Recognition, Prognosis, and Therapy: A Systematic Review," JAMA 324(1):79-89.

Graham. F.L. et al. (1977). "Characteristics of a Human Cell Line Transformed by DNA from Human Adenovirus Type 5," J. Gen Virol. 36:59-72.

Hamers-Casterman, C. et al. (Jun. 3, 1993). "Naturally Occurring Antibodies Devoid of Light Chains," Nature 363:446-448.

Hammerling, G.J. et al. Eds. (1981). "Monoclonal Antibodies and T-Cell Hybridomas," Chapter 12 in Research Monographs in Immunology Elsevier: New York, NY, 3:563-681.

Harris, W.J. (1995). "Production of Humanized Monoclonal and Antibodies for in vivo Imaging and Therapy," Biochem. Soc. Transactions 23:1035-1038.

Higgins, D.G. et al. (1988). "CLUSTAL: A Package for Performing Multiple Sequence Alignment on a Microcomputer," Gene 73(1):237-244.

Higgins, D.G. et al. (1989). "Fast and Sensitive Multiple Sequence Alignments on a Microcomputer," CABIOS Communications 5(2):151-153.

Hongo, J.A.S. et al. (1995). "Development and Characterization of Murine Monoclonal Antibodies to the Latency-Associated Peptide of Transforming Growth Factor Beta1," Hybridoma 14(3):253-260.

Hoogenboom, H.R. et al. (Sep. 20, 1992). "By-Passing Immunisation Human Antibodies From Synthetic Repertoires of Germline VH Gene Segments Rearranged In Vitro," J. Mol. Biol. 227(2):381-388.

Huang, X. et al. (Apr. 1992). "Parallelization of a Local Similarity Algorithm," Comput. Appl. Biosci. 8(2):155-165.

Hurle, M.R. et al. (1994). "Protein Engineering Techniques for Antibody Humanization," Curr. Op. Biotech. 5(4):428-433.

Jaikaran, E.T.A.S. et al. (2001). "Islet Amyloid and Type 2 Diabetes: From Molecular Misfolding to Islet Pathophysiology," Biochimica et Biophysica Acta 1537(3):179-203.

Jakobovits, A. et al. (Mar. 18, 1993). "Germ-Line Transmission and Expression of a Human-Derived Yeast Artificial Chromosome," Nature 362(6417):255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.

Johnson, G. et al. (2003). "The Kabat Database and a Bioinformatics Example," Chapter 2 in Methods in Molecular Biology, Lo, B.K.C, Humana Press, Totawa, N.J., 248:11-25.

Jones, P.T. et al. (May 29, 1986). "Replacing the Complementarity-Determining Regions in a Human Antibody With Those From a Mouse," Nature 321:522-525.

Kisilevsky, R. (1994). "Proteoglycans and Other Basement Membrane Proteins in Amyloidosis," Molecular Neurobiology 9(1):23-24.

Kisilevsky, R. (Nov. 1990). "Heparan Salfate Proteoglycans in Amyloidogenesis: An Epiphenomenom, A Unique Factor, or the Tip of a More Fundamental Process?," Laboratory Investigation 63(5):589-591.

Kohler, G. et al. (Aug. 7, 1975). "Continuous Culture of Fused Cells Secreting Antibody of Predefined Specificity," Nature 256:495-497.

Lee, C.V. et al. (2004). "Bivalent Antibody Phage Display Mimics Natural Immunoglobulin,".J. Immunol. Methods 284(1-2):119-132.

Lee, C.V. et al. (2004). "High-Affinity Human Antibodies From Phage-Displayed Synthetic Fab Libraries With a Single Framework Scaffold," J. Mol. Biol. 340:1073-1093.

Lee, J. et al. (May 1999). "Control of Fed-Batch Fermentations," Biotechnology Advances 17(1):29-48, 21 pages.

Li, J. et al. (Mar. 7, 2006). "Human Antibodies for Immunotherapy Development Generated via a Human B Cell Hybridoma Technology," Proc. Natl. Acad. Sci. USA 103(10):3557-3562.

Li, J.P. et al. (May 3, 2005). "In Vivo Fragmentation of Heparan Sulfate by Heparanase Overexpression Renders Mice Resistant to Amyloid Protein A Amyloidosis," PNAS 102(18):6473-6477.

Lin, C.Y. et al. (May 2007). "Toxic Human Islet Amyloid Polypeptide (h-IAPP) Oligomers Are Intracellular, and Vaccination to Induce Anti-Toxic Oligomer Antibodies Does Not Prevent h-IAPP-Induced β-Cell Apoptosis in h-IAPP Transgenic Mice," Diabetes 56:1324-1332.

Lofberg, H. et al. (1987). "The Prevalence of Renal Amyloidosis of the AA-Type in a Series of 1, 158 Consecutive Autopsies," Acta Path. Microbiol. Immunol. Scand. Sect. A 95:297-302.

Lonberg, N. et al. (1995, e-pub. Jul. 10, 2009). "Human Antibodies From Transgenic Mice," Int. Rev. Immunol. 13(1):65-93.

Lonberg, N. et al. (Apr. 28, 1994). "Antigen-Specific Human Antibodies From Mice Comprising Four Distinct Genetic Modifications," Nature 368(6474):856-859.

Marks, J.D. et al. (1991). "By-Passing Immunization Human Antibodies from V-gene Libraries Displayed on Phage," J. Mol. Biol. 222:581-597.

Marks, J.D. et al. (Jul. 1992). "By-Passing Immunization: Building High Affinity Human Antibodies by Chain Shuffling," Bio/Technology 10:779-783.

Mather, J.P. et al. (1980). "Establishment and Characterization of Two Distinct Mouse Testicular Epithelial Cell Lines," Biology of Reproduction 23:243-252.

(56) References Cited

OTHER PUBLICATIONS

Mather, J.P. et al. (1982). "Culture of Testicular Cells in Hormone-Supplemented Serum-Free Medium," Annals New York Academy of Sciences pp. 44-68.
Merlini, G. (2004). "Systemic Amyloidosis: Are We Moving Ahead?," Neth J Med 62(4):104-105, 2 pages.
Merlini, G. et al. (2004). "The Systemic Amyloidoses: Clearer Understanding of the Molecular Mechanisms Offers Hope for More Effective Therapies," Journal of Internal Medicine 255:159-178.
Merlini, G. et al. (Aug. 7, 2003). "Molecular Mechanisms of Amyloidosis," New England Journal of Medicine 349:583-596.
Morrison, S.L. (Apr. 28, 1994). "Success in Specification," Nature 368:812-813.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Mucchiano, G.I. et al. (2001, e-pub. Nov. 16, 2000). "Apolipoprotein A-1-Derived Amyloid in Atherosclerotic Plaques of the Human Aorta," The Journal of Pathology 193(2):270-275.
Needleman, S. B. et al. (Mar. 1970). "A General Method Applicable to the Search for Similarities in the Amino Acid sequence of Two Proteins," J. Mol. Biol. 48:443-453.
Neuberger, M. (Jul. 1996). "Generating High-Avidity Human Mabs in Mice," Nature Biotechnology 14:826.
Pearson, W.R. (1994). "Using the FASTA Program to Search Protein and DNA Sequence Databases," Methods in Molecular Biology 24:307-331.
Pearson, W.R. et al. (Apr. 1988). "Improved Tools for Biological Sequence Comparison," Proc. Natl. Acad. Sci. USA 85(8):2444-2448.
Plückthun, A. (1994). "Antibodies from *Escherichia coli*," in Chapter 11 the Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Riechmann, L. et al. (Mar. 24, 1988). "Reshaping Human Antibodies for Therapy," Nature 332:323-329.
Rocken, C. (2002, e-pub. Jan. 4, 2002). "Pathology, Diagnosis and Pathogenesis of AA Amyloidosis," Virchows Arch 440(2):111-122.
Rocken, C. et al. (2006, e-pub. Oct. 26, 2006). "Cathepsin Protease Activity Modulates Amyloid Load in Extracerebral Amyloidosis," The Journal of Pathology 210(4):478-487.
Rocken, C. et al. (Mar. 2001). "A Putative Role for Cathepsin K in Degradation of AA and AL Amyloidosis," Am. J. Pathol. 158(3):1029-1038.
Sheriff, S. et al. (Sep. 1996). "Redefining the Minimal Antigen-Binding Fragment," Nature Struct. Biol. 3(9):733-736.
Sidhu, S.S. et al. (2004). "Phage-Displayed Antibody Libraries of Synthetic Heavy Chain Complementarity Determining Regions," J. Mol. Biol. 338(2):299-310.
Smith, T.F. et al. (1981). "Comparison of Biosequences," Advances in Appl. Math. 2:482-489.
Snow, A.D. et al. (Jan. 1987). "Sulfated Glycosaminoglycans: A Common Constituent of All Amyloids?," Laboratory Investigation 56(1):120-123.
Solomon, A. et al. (Nov. 2006). "Amyloid Contained in the Knee Joint Meniscus Is Formed From Apolipoprotein A-I," Arthritis & Rheumatism 54(11):3545-3550.
Sunde, M. et al. (1997). "Common Core Structure of Amyloid Fibrils by Synchrotron X-Ray Diffraction," Journal of Molecular Biology 273(3):729-739.
Thornton, J.M. et al. (Nov. 14, 1991). "Prediction of Progress at Last," Nature 354(6349):105-106.
U.S. Appl. No. 18/181,489, filed Mar. 9, 2023, for Jonathan S. Wall, et al. (A U.S. Patent Application is not submitted herewith pursuant to the waiver of 37 C.F.R. § 1.98(a)(2)(iii) issued by the Office on Sep. 21, 2004.).
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Van Dijk, M.A. et al. (Aug. 2001). "Human Antibodies as Next Generation Therapeutics," Curr. Opin. Che. Biology 5(4):368-374.
Vaswani, S.K. et al (Aug. 1998). "Humanized Antibodies as Potential Therapeutic Drugs," Ann. Allergy, Asthma & Immunol. 81:105-119.
Vollmer, E. et al. (1991). "Distribution Patterns of Apolipoproteins A1, A2, and B in the Wall of Atherosclerotic Vessels," Virchows Archiv A 419(2):79-88.
Wall, J.S. et al. (Jun. 4, 2013). "A Binding-Site Barrier Affects Imaging Efficiency of High Affinity Amyloid-Reactive Peptide Radiotracers In Vivo," PloS One 8(6):e66181, 1-10.
Westermark, P. et al. (Nov. 1995). "Apolipoprotein A1-Derived Amyloid in Human Aortic Atherosclerotic Plaques," The American Journal of Pathology 147(5):1186-1192.
Westermark, P. et al. (Sep. 2007). "A Primer of Amyloid Nomenclature," Amyloid 14(3):179-183.
Wlaschin, K.F. et al. (2006, e-pub. Jun. 10, 2006). "Fedbatch Culture and Dynamic Nutrient Feeding," Adv Biochem Engin/Biotechnol. 101:43-74.
Xu, J.L. et al. (Jul. 2000). "Diversity in the CDR3 Region of V(H) Is Sufficient for Most Antibody Specificities," Immunity 13:37-45.
Yazaki, P.J. et al. (2003). "Expression of Recombinant Antibodies in Mammalian Cell Lines," Methods in Molecular Biology 248:255-268.
Attwood, T.K. (Oct. 20, 2000). "The Babel of Bioinformatics," Science 290(5491):471-473, 7 pages.
Edwards, B.M. et al. (Nov. 14, 2003). "The Remarkable Flexibility of the Human Antibody Repertoire; Isolation of Over One Thousand Different Antibodies to a Single Protein, BLyS," J. Mol. Biol. 334(1):103-118.
Foster, J.S. et al. (Oct. 2, 2023). "Development and Characterization of a Prototypic Pan-Amyloid Clearing Agent—A Novel Murine Peptide-Immunoglobulin Fusion," Frontiers in Immunology 14(1275372):1-14.
Foster, J.S. et al. (Sep. 4, 2017). "A Peptide-Fc Opsonin With Pan-Amyloid Reactivity," Frontiers in Immunology 8(1082):1-14.
Goel, M. et al. (2004). "Plasticity within the Antigen-Combining Site May Manifest as Molecular Mimicry in the Humoral Immune Response," J. Immunol. 173(12):7358-7367.
Janeway, C.A. et al. (1997). Immunobiology, 3rd edition Garland Press, pp. 3.1-3.11, 14 pages.
Kanyavuz, A. et al. (Jun. 2019, e-pub. Feb. 4, 2019). "Breaking the Law: Unconventional Strategies for Antibody Diversification," Nat. Rev. Immunol 19(6):355-368.
Lescar, J. et al. (Jul. 30, 1995). "Crystal Structure of a Cross-Reaction Complex Between Fab F9.13.7 and Guinea Fowl Lysozyme," The Journal of Biological Chemistry 276(30):18067-18076.
Lloyd, C. et al. (2009, e-pub. Oct. 29, 2008). "Modelling the Human Immune Response: Performance of a 1011 Human Antibody Repertoire Against a Broad Panel of Therapeutically Relevant Antigens," Protein Engineering, Design & Selection 22(3):159-168.
Rudikoff, S. et al. (Mar. 1982). "Single Amino Acid Substitution Altering Antigen-Binding Specificity," Proc. Natl. Acad. Sci. USA 79:1979-1983.
Skolnick, J. et al. (Jan. 2000). "From Genes to Protein Structure and Function: Novel Applications of Computational Approaches in the Genomic Era," Trends in Biotechnology 18:34-39.
Stryer, L. (1995). Biochemistry, Fourth Edition, W.H. Freeman and Company: New York, 18-23, 8 pages.
Westermark, P. et al. (Jun. 30, 2009). "Fibrils From Designed Non-Amyloid-Related Synthetic Peptides Induce AA-Amyloidosis During Inflammation in an Animal Model," PLoS One 4(6):e6041, 7 pages.
Wikipedia (Oct. 2, 2023). "Amyloid—Proteins Forming Amyloids in Diseases," 18 pages as retrieved on Dec. 1, 2023 from https://en.wikipedia.org/w/index.php?title=Amyloid&oldid=1178199603.
Beierle, S.P. et al. (2016). "A Novel Murine Model of Light Chain Associated (AL) Amyloidosis for Validating Peptide Amyloid Imaging Agents—A SPECT/CT and Microautoradiography Study," 2016

(56) References Cited

OTHER PUBLICATIONS

World Molecular Imaging Congress, New York, NY, Sep. 7-10, 2016, Control ID 2500594:1 page.
Edwards, C.V. et al. (2017, e-pub. Apr. 22, 2017). "Interim Analysis of the Phase 1a/b Study of Chimeric Fibril-Reactive Monoclonal Antibody 11-1F4 in Patients With AL Amyloidosis," Amyloid 24(S1):58-59.
Foster, J.S. et al. (2020). "Collagen Addition to Synthetic Amyloid Fibrils Presents a "Don't Eat Me" Signal That Prevents Macrophage Phagocytosis," International Symposium on Amyloidosis, Tarragona, Spain, Sep. 14-18, 2020 (virtual), PM030:110, 1 page.
Heidel, R.E. et al. (2020). "Validation of a Novel Model for the Comparative Analysis of Amyloid-Reactive Biologicals Using a Single Mouse," International Symposium on Amyloidosis, Tarragona, Spain, Sep. 14-18, 2020 (virtual), PM001:80, 1 page.
Kennel, S.J. et al. (2020). "Amyloid Binding and Opsonization Properties of a Novel Peptope-Antibody Complex," International Symposium on Amyloidosis, Tarragona, Spain, Sep. 14-18, 2020 (virtual), PM031:111, 1 page.
Lee, S. et al. (2013). "Dual Isotope SPECT Imaging of I-123 and I-125," IEEE Medical Imaging Conference, Seoul, South Korea, Oct. 27-Nov. 2, 2013, 4 pages.
Martin, E.B. et al. (2014). "Characterization of a Novel Peptide, P43, Optimized For Pancreatic Amyloid Detection," XIVth International Symposium on Amyloidosis, Indianapolis, IN, Apr. 28-May 1, 2014, OP-28:47, 1 page.
Martin, E.B. et al. (2014). "Characterization of Peptide 125I-p5R+14 as an Optimized Radiotracer for the in Vivo Detection of ApoA2c Amyloidosis," XIVth International Symposium on Amyloidosis, Indianapolis, IN, Apr. 28-May 1, 2014, PA-26:127, 1 page.
Martin, E.B. et al. (2014). "Detection of Cardiac Amyloidosis by SPECT/CT Imaging Using Both 125I-Serum Amyloid P-Component and the Novel 125I-p5R+14 Peptide," XIVth International Symposium on Amyloidosis, Indianapolis, IN, Apr. 28-May 1, 2014, OP-22:40-41.
Martin, E.B. et al. (2017). "Recruitment of Human Light Chain Proteins by Synthetic Fibrils Is Dependent on Disease State and May Be Used to Predict Amyloidogenic Propensity," Amyloid 24(S1):24-25.
Martin, E.B. et al. (Nov. 2020). "Looking for Amyloid in All the Right Places," Journal of Cardiac Failure 26(11):917-918.
Martin, E.B. et al. (Sep. 20, 2013). "Characterization of Peptide 125I-p5R+14 as an Optimized Radiotracer for the In Vivo Detection of ApoA2c Amyloidosis," World Molecular Imaging Congress, Savannah, GA, Sep. 18-21, 2013, Poster Session 3, Presentation No. P333:S839-S840.
Martin, E.B. et al. (Sep. 7, 2012). "Ex Vivo Identification and In Vivo Validation of a Novel Visceral Amyloid Imaging Peptide," World Molecular Imaging Congress, Dublin, Ireland, Sep. 5-8, 2012, Poster Session 3, Presentation No. P481:S1517, 1 page.
Morgan, G.J. et al. (2020). "The Process of Amyloid Formation Due to Monoclonal Immunoglobulins," Hematology/Oncology Clinics of North America 34(6):1041-1054.
Osborne, D. et al. (Sep. 5, 2012). "I-131 Rodent Imaging on the Inveon SPECT Platform Using a Novel Blended Collimator Acquisition Method," World Molecular Imaging Congress, Dublin, Ireland, Sep. 5-8, 2012, Poster Session 1, Presentation No. P154:S1190, 1 page.
Ramirez-Alvarado, M. et al. (Feb. 12, 2017). "82-Symp. From Native to Amyloid in the Test Tube and in Cells: A Journey of Misbehaving Antibodies," Biophys J. 112(3):15a, 1 page.
Stuckey, A. et al. (2020). "Dynamic Biodistribution of 124I-p5+14 in Patients With AL Amyloidosis," International Symposium on Amyloidosis, Tarragona, Spain, Sep. 14-18, 2020 (virtual), PT046:272, 1 page.
Stuckey, A. et al. (May 1, 2017). "Preclinical SPECT/CT Imaging, in a Mouse, of a Novel Bifunctional Pre-Targeting Peptide for Systemic Amyloidosis Immunotherapy," Journal of Nuclear Medicine 58 (Suppl 1):1112, 2 pages.
Stuckey, A. et al. (May 1, 2018). "Preliminary Pharmacokinetic Study of a Bispecific Peptide for Pretargeting Immunotherapy of Amyloidosis Using PreClinical SPECT/CT," Journal of Nuclear Medicine 59(Suppl 1):1834, 2 pages.
Stuckey, A. et al. (May 1, 2019). "Characterization of a Novel Â Sheet-Structured Peptide for Pretargeting Immunotherapy of Amyloidosis," Journal of Nuclear Medicine 60(Suppl 1):3021, 2 pages.
U.S. Appl. No. 18/660,156, filed May 9, 2024, for Jonathan S. Wall, et al. (A U.S. Patent Application is not submitted herewith pursuant to the waiver of 37 C.F.R. § 1.98(a)(2)(iii) issued by the Office on Sep. 21, 2004.).
U.S. Appl. No. 18/660,162, filed May 9, 2024, for Jonathan S. Wall, et al. (A U.S. Patent Application is not submitted herewith pursuant to the waiver of 37 C.F.R. § 1.98(a)(2)(iii) issued by the Office on Sep. 21, 2004.).
Wall, J. et al. (2022). "Preclinical Characterization of AT-02, a Pan-Amyloid-Binding Immunoglobulin-Peptide Fusion Protein Capable of Enhancing Phagocytosis and Facilitating Reduction of Amyloid," International Society of Amyloidosis, Heidelberg, Germany, Sep. 4-8, 2022, OP037:14 pages.
Wall, J. et al. (2024). "Characterization of a Novel Beta-Sheet Peptide-Fc Fusion for Targeting Systemic Amyloid Deposits," International Society of Amyloidosis XIX International Meeting, Rochester, MN, May 2024 254:S102, 1 page.
Wall, J. et al. (2024). "Characterization of the Peptide-Antibody Fusion, AT-02-Studies to Support Its Use as an Immunotherapy in Patients With Amyloidosis," Poster, presented at International Society of Amyloidosis XIX International Meeting, Rochester, MN, May 2024, 1 page.
Wall, J. et al. (Jan. 1, 2024). "The Peptide Fusion Immunoglobulin, AT-02, Exhibits Highly Potent Pan-Amyloid Reactivity and Immunomodulation," Journal of Cardiac Failure 30(1):217, 1 page.
Wall, J. et al. (May 1, 2020). "Characterization and In Vivo Target Engagement Studies of a Novel, Preformed, Amyloid-Reactive Peptope-Antibody Complex," Journal of Nuclear Medicine 61(Suppl 1) 324:2 pages.
Wall, J.S. et al. (2014). "Heparin-Binding Peptides, Basic Fibroblast Growth Factor and p5R, Bind to Different Targets in Amyloid-Laden Mice and Controls," XIVth International Symposium on Amyloidosis, Indianapolis, IN, Apr. 28-May 1, 2014, PA-46:144-145.
Wall, J.S. et al. (2014). "High Affinity Amyloid-Reactive Peptide, p5R, Binds Non-Uniformly to Large Amyloid Deposits Due to a Binding Site Barrier Effect," XIVth International Symposium on Amyloidosis, Indianapolis, IN, Apr. 28-May 1, 2014, OP-23:41-42.
Wall, J.S. et al. (2014). "Soluble, Recombinant, Receptor for Advanced Glycation End-Products (RAGE) Binds AA Amyloid In Vivo," XIVth International Symposium on Amyloidosis, Indianapolis, IN, Apr. 28-May 1, 2014, OP-2:21, 1 page.
Wall, J.S. et al. (2014). "Specific Accumulation of Radiolabeled Peptide p5 in Cerebral Vascular and Parenchymal AB Amyloid in Mice," XIVth International Symposium on Amyloidosis, Indianapolis, IN, Apr. 28-May 1, 2014, PA-45:143-144.
Wall, J.S. et al. (2016). "A Bifunctional Peptide, "Peptope", for Pre-Targeting Immunotherapy of Systemic Amyloidosis Evaluated by Using Microautoradiography and SPECT/CT Imaging in a Mouse Model," 2016 World Molecular Imaging Congress, New York, NY, Sep. 7-10, 2016, Control ID 2500429:1 page.
Wall, J.S. et al. (2017, e-pub. Aug. 21, 2017). "Pretargeting Immunotherapy: A Novel Treatment Approach for Systemic Amyloidosis," Pharmaceutical Patent Analyst 6(5):215-223.
Wall, J.S. et al. (2018, e-pub. Oct. 30, 2018). "Bifunctional Amyloid-Reactive Peptide Promotes Binding of Antibody 11-1F4 to Diverse Amyloid Types and Enhances Therapeutic Efficacy," PNAS 115(46):E10839-E10848.
Wall, J.S. et al. (2020). "Synthesis and Evaluation of a Novel Peptide-Immunoglobulin Fusion for Targeting and Phagocytosis of Amyloid," International Symposium on Amyloidosis, Tarragona, Spain, Sep. 14-18, 2020 (virtual), PM053:133, 1 page.
Wall, J.S. et al. (2023). "Characterization of AT-02, a Pan-Amyloid-Binding Peptide Fusion Immunoglobulin With High Binding Potency,

(56) References Cited

OTHER PUBLICATIONS

Complement Activation, and Immune Cell Stimulation," European Heart Journal 44(Suppl 2):1 page.

Wall, J.S. et al. (Dec. 26, 2012). "AL Amyloid Imaging and Therapy With a Monoclonal Antibody to a Cryptic Epitope on Amyloid Fibrils," PloS One 7(12):e52686, 10 pages.

Wall, J.S. et al. (May 7, 2012). "Amyloid-Reactive Peptides Bind MelA+ Melanocytes and Extracellular Melanin in Human, Canine and Murine Melanoma Tumors," XIIIth International Symposium on Amyloidosis, Groningen, Netherlands, May 6-10, 2012, PA62:123-124.

Wall, J.S. et al. (Sep. 18, 2013). "Evaluation of SPECT Detection of Cardiac Amyloidosis in Mice by Using 125I-p5R+14 Peptide or 125I-SAP," World Molecular Imaging Congress, Savannah, GA, Sep. 18-21, 2013, Poster Session 1, Presentation No. P071:S418-S419.

Wall, J.S. et al. (Sep. 19, 2013). "Preliminary Evaluation of [18F]SFB- and [18F]FBAM-Labeled Amyloidophilic Peptides in Mice With Visceral Amyloidosis," World Molecular Imaging Congress, Savannah, GA, Sep. 18-21, 2013, Poster Session 2, Presentation No. P163:S572-S573.

Wall, J.S. et al. (Sep. 7, 2012). "Arginine-Rich Peptide p5R Provides Enhanced Binding to Visceral Amyloid Deposits In Vitro and In Vivo," World Molecular Imaging Congress, Dublin, Ireland, Sep. 5-8, 2012, Poster Session 3, Presentation No. P493:S1529, 1 page.

Wall, J.S. et al. (Sep. 7, 2012). "Heparin-Binding Peptides bFGF and p5R Bind to Different Targets in Amyloid-Laden Mice and Controls," World Molecular Imaging Congress, Dublin, Ireland, Sep. 5-8, 2012, Poster Session 3, Presentation No. P492:S1528, 1 page.

Wall, J.S. et al. (Sep. 8, 2012). "Heparin-Reactive Peptide p5R Preferentially Binds a Subset of MelA+ Melanocytes and Extracellular Melanin—A Novel Biomarker in Metastatic Melanoma Tumors," World Molecular Imaging Congress, Dublin, Ireland, Sep. 5-8, 2012, Scientific Session 25: Preclinical In Vivo-Oncology, Presentation No. SS176:S1970, 1 page.

Wang, Z. et al. (2021). "Computational Investigation of the Binding of a Designed Peptide to a Light Chain Amyloid Fibril," Physical Chemistry Chemical Physics 23:20634-20644.

Wells, K. et al. (May 2012). "Radioimmunoimaging of Amyloid Deposits in AL Amyloidosis," Journal of Nuclear Medicine 53(Suppl 1):537, 3 pages.

\* cited by examiner

FIG. 7A

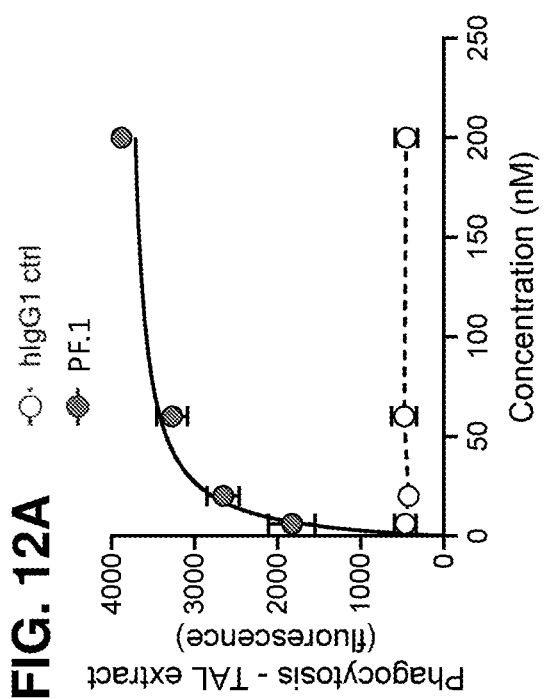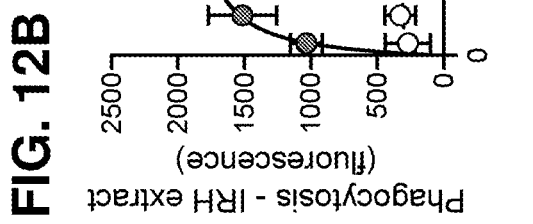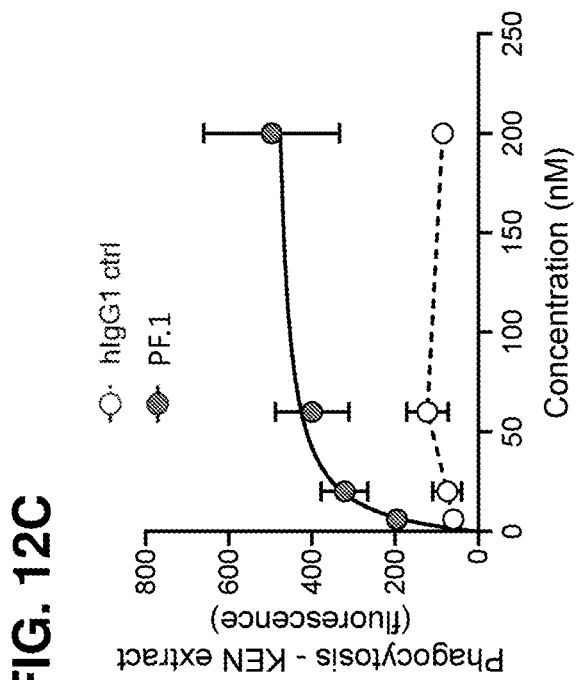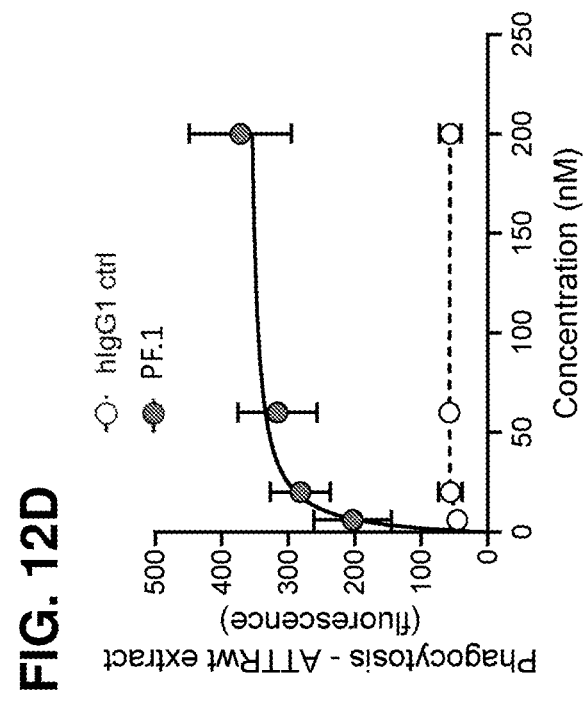
FIG. 12A
FIG. 12B
FIG. 12C
FIG. 12D

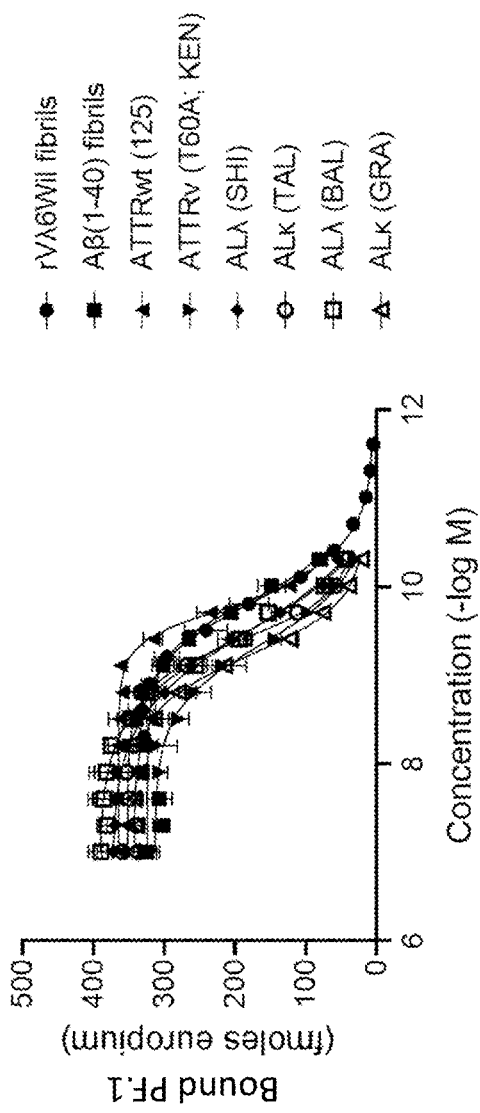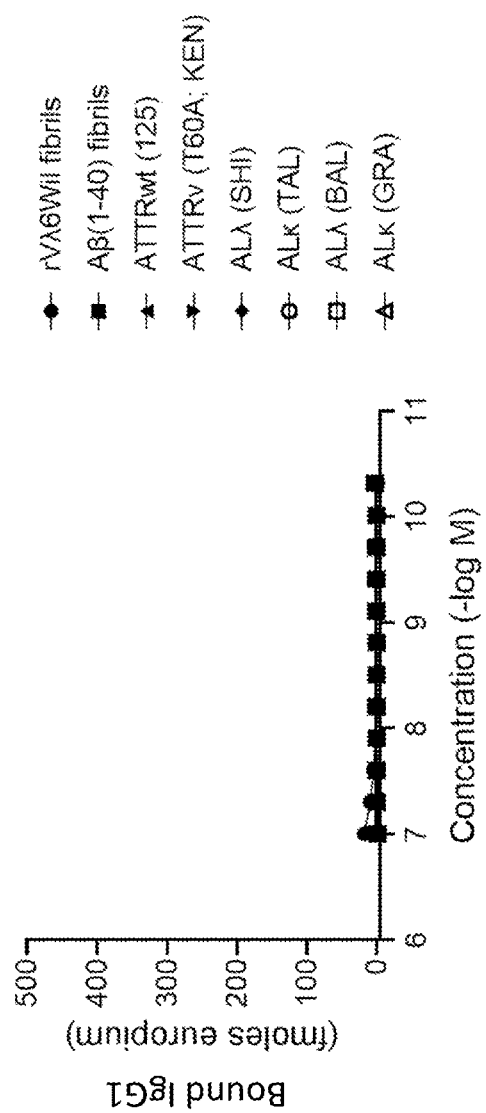
FIG. 13A
FIG. 13B

```
                       SEQUENCE LISTING

Sequence total quantity: 92
SEQ ID NO: 1            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 1
KAQKAQKAQKA KQAQKAQKAQ AKQAKQ                                      26

SEQ ID NO: 2            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 2
RAQRAQARQA RQAQRAQRAQ ARQARQ                                       26

SEQ ID NO: 3            moltype = AA  length = 15
```

```
                        -continued

FEATURE                 Location/Qualifiers
REGION                  1..15
                        note = Synthetic Construct
source                  1..15
                        mol_type = protein
                        organism = synthetic construct
SEQUENCE: 3
KAKAKAKAKA KAKAK                                                      15

SEQ ID NO: 4            moltype = AA  length = 29
FEATURE                 Location/Qualifiers
REGION                  1..29
                        note = Synthetic Construct
source                  1..29
                        mol_type = protein
                        organism = synthetic construct
SEQUENCE: 4
KAQAKAQAKA QAKAQAKAQA KAQAKAQAK                                       29

SEQ ID NO: 5            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 5
KAQQAQAKQA QQAQKAQQAQ AKQAQQ                                          26

SEQ ID NO: 6            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 6
QAQKAQQA KQAQQAQKAQ AQQAKQ                                            26

SEQ ID NO: 7            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 7
KAQKAQAKQA KQAQKAQKAQ AKQAKQ                                          26

SEQ ID NO: 8            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 8
KTVKTVTKVT KVTVKTVKTV TKVTKV                                          26

SEQ ID NO: 9            moltype = AA  length = 18
FEATURE                 Location/Qualifiers
REGION                  1..18
                        note = Synthetic Construct
source                  1..18
                        mol_type = protein
                        organism = synthetic construct
SEQUENCE: 9
VYKVKTKVKT KVKTKVKT                                                   18

SEQ ID NO: 10           moltype = AA  length = 30
FEATURE                 Location/Qualifiers
REGION                  1..30
                        note = Synthetic Construct
source                  1..30
                        mol_type = protein
                        organism = synthetic construct
SEQUENCE: 10
AQAYSKAQKA QAKQAKQAQK AQKAQAKAKQ                                      30
```

```
SEQ ID NO: 11              moltype = AA   length = 31
FEATURE                    Location/Qualifiers
REGION                     1..31
                           note = Synthetic Construct
source                     1..31
                           mol_type = protein
                           organism = synthetic construct
SEQUENCE: 11
AQAYARAQRA QARQARQAQR AQRAQARQAR Q                                    31

SEQ ID NO: 12              moltype = AA   length = 40
FEATURE                    Location/Qualifiers
REGION                     1..40
                           note = Synthetic Construct
source                     1..40
                           mol_type = protein
                           organism = synthetic construct
SEQUENCE: 12
KAQKAQAKQA KQAQKAQKAQ AKQAKQAQKA QKAQAKQAKQ                           40

SEQ ID NO: 13              moltype = AA   length = 40
FEATURE                    Location/Qualifiers
REGION                     1..40
                           note = Synthetic Construct
source                     1..40
                           mol_type = protein
                           organism = synthetic construct
SEQUENCE: 13
RAQRAQARQA RQARQARQAQ ARQARQAQRA QRAQARQARQ                           40

SEQ ID NO: 14              moltype =    length =
SEQUENCE: 14
000

SEQ ID NO: 15              moltype = AA   length = 111
FEATURE                    Location/Qualifiers
REGION                     1..111
                           note = Synthetic Construct
source                     1..111
                           mol_type = protein
                           organism = synthetic construct
SEQUENCE: 15
QVQLKESGPG LVAPSQSLSI TCTVSGFSLS SYGVSWVRQP PGKGLEWLGV IWGDGSTNYH      60
PNLMSRLSIS KDISKSQVLF KLNSLQTDDT ATYYCVTLDY WGQGTSVTVS S              111

SEQ ID NO: 16              moltype = AA   length = 112
FEATURE                    Location/Qualifiers
REGION                     1..112
                           note = Synthetic Construct
source                     1..112
                           mol_type = protein
                           organism = synthetic construct
SEQUENCE: 16
DVVMTQTPLS LPVSLGDQAS ISCRSSQSLV HRNGNTYLHW YLQKPGQSPK LLIYKVSNRF      60
SGVPDRFSGS GSGTDFTLKI SRVEAEDLGL YFCFQTTYVP NTFGGGTKLE IK             112

SEQ ID NO: 17              moltype = AA   length = 10
FEATURE                    Location/Qualifiers
REGION                     1..10
                           note = Synthetic Construct
source                     1..10
                           mol_type = protein
                           organism = synthetic construct
SEQUENCE: 17
GFSLSSYGVS                                                            10

SEQ ID NO: 18              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 18
VIWGDGSTNY HPNLMS                                                     16

SEQ ID NO: 19              moltype =    length =
SEQUENCE: 19
000
```

```
SEQ ID NO: 20              moltype = AA  length = 16
FEATURE                    Location/Qualifiers
REGION                     1..16
                           note = Synthetic Construct
source                     1..16
                           mol_type = protein
                           organism = synthetic construct
SEQUENCE: 20
RSSQSLVHRN GNTYLH                                                          16

SEQ ID NO: 21              moltype = AA  length = 7
FEATURE                    Location/Qualifiers
REGION                     1..7
                           note = Synthetic Construct
source                     1..7
                           mol_type = protein
                           organism = synthetic construct
SEQUENCE: 21
KVSNRFS                                                                    7

SEQ ID NO: 22              moltype = AA  length = 9
FEATURE                    Location/Qualifiers
REGION                     1..9
                           note = Synthetic Construct
source                     1..9
                           mol_type = protein
                           organism = synthetic construct
SEQUENCE: 22
FQTTYVPNT                                                                  9

SEQ ID NO: 23              moltype = AA  length = 15
FEATURE                    Location/Qualifiers
REGION                     1..15
                           note = Synthetic Construct
source                     1..15
                           mol_type = protein
                           organism = synthetic construct
SEQUENCE: 23
AQAGQAGQAQ GGGYS                                                           15

SEQ ID NO: 24              moltype = AA  length = 5
FEATURE                    Location/Qualifiers
REGION                     1..5
                           note = Synthetic Construct
source                     1..5
                           mol_type = protein
                           organism = synthetic construct
SEQUENCE: 24
VTPTV                                                                      5

SEQ ID NO: 25              moltype = AA  length = 158
FEATURE                    Location/Qualifiers
REGION                     1..158
                           note = Synthetic Construct
source                     1..158
                           mol_type = protein
                           organism = synthetic construct
SEQUENCE: 25
AQAGQAGQAQ GGGYSKAQKA QAKQAKQAQK AQKAQAKQAK QVTPTVDVVM TQTPLSLPVS           60
LGDQASISCR SSQSLVHRNG NTYLHWYLQK PGQSPKLLIY KVSNRFSGVP DRFSGSGSGT          120
DFTLKISRVE AEDLGLYFCF QTTYVPNTFG GGTKLEIK                                  158

SEQ ID NO: 26              moltype = AA  length = 143
FEATURE                    Location/Qualifiers
REGION                     1..143
                           note = Synthetic Construct
source                     1..143
                           mol_type = protein
                           organism = synthetic construct
SEQUENCE: 26
KAQKAQAKQA KQAQKAQKAQ AKQAKQVTPT VDVVMTQTPL SLPVSLGDQA SISCRSSQSL           60
VHRNGNTYLH WYLQKPGQSP KLLIYKVSNR FSGVPDRFSG SGSGTDFTLK ISRVEAEDLG          120
LYFCFQTTYV PNTFGGGTKL EIK                                                  143

SEQ ID NO: 27              moltype = AA  length = 5
FEATURE                    Location/Qualifiers
REGION                     1..5
                           note = Synthetic Construct
```

```
source                      1..5
                            mol_type = protein
                            organism = synthetic construct
SEQUENCE: 27
GGGYS                                                                            5

SEQ ID NO: 28               moltype = AA   length = 101
FEATURE                     Location/Qualifiers
source                      1..101
                            mol_type = protein
                            organism = Homo sapiens
SEQUENCE: 28
DVVMTQSPLS LPVTLGQPAS ISCRSSQSLV HSDGNTYLNW FQQRPGQSPR RLIYKVSNRD     60
SGVPDRFSGS GSGTDFTLKI SRVEAEDVGV YYCMQGTHWP P                        101

SEQ ID NO: 29               moltype = AA   length = 112
FEATURE                     Location/Qualifiers
source                      1..112
                            mol_type = protein
                            organism = Homo sapiens
SEQUENCE: 29
DVVMTQSPLS LPVTLGQPAS ISCRSSQSLV HSDGNTYLNW FQQRPGQSPR RLIYKVSNRD     60
SGVPDRFSGS GSGTDFTLKI SRVEAEDVGV YYCFQTTYVP NTFGGGTKLE IK            112

SEQ ID NO: 30               moltype = AA   length = 97
FEATURE                     Location/Qualifiers
source                      1..97
                            mol_type = protein
                            organism = Homo sapiens
SEQUENCE: 30
QVQLQESGPG LVKPSETLSL TCTVSGGSIS SYYWSWIRQP PGKGLEWIGY IYTSGSTNYN     60
PSLKSRVTIS VDTSKNQFSL KLSSVTAADT AVYYCAR                              97

SEQ ID NO: 31               moltype = AA   length = 111
FEATURE                     Location/Qualifiers
source                      1..111
                            mol_type = protein
                            organism = Homo sapiens
SEQUENCE: 31
QVQLQESGPG LVKPSETLSL TCTVSGGSIS SYYWSWIRQP PGKGLEWIGY IYTSGSTNYN     60
PSLKSRVTIS VDTSKNQFSL KLSSVTAADT AVYYCARLDY WGQGTSVTVS S             111

SEQ ID NO: 32               moltype = AA   length = 112
FEATURE                     Location/Qualifiers
REGION                      1..112
                            note = Synthetic Construct
source                      1..112
                            mol_type = protein
                            organism = synthetic construct
SEQUENCE: 32
DVVMTQSPLS LPVTLGQPAS ISCRSSQSLV HRNGNTYLHW FQQRPGQSPR RLIYKVSNRF     60
SGVPDRFSGS GSGTDFTLKI SRVEAEDVGV YYCFQTTYVP NTFGGGTKLE IK            112

SEQ ID NO: 33               moltype = AA   length = 112
FEATURE                     Location/Qualifiers
REGION                      1..112
                            note = Synthetic Construct
source                      1..112
                            mol_type = protein
                            organism = synthetic construct
SEQUENCE: 33
DVVMTQSPLS LPVTLGQPAS ISCRSSQSLV HRNGNTYLHW YLQRPGQSPR RLIYKVSNRF     60
SGVPDRFSGS GSGTDFTLKI SRVEAEDVGV YYCFQTTYVP NTFGGGTKLE IK            112

SEQ ID NO: 34               moltype = AA   length = 112
FEATURE                     Location/Qualifiers
REGION                      1..112
                            note = Synthetic Construct
source                      1..112
                            mol_type = protein
                            organism = synthetic construct
SEQUENCE: 34
DVVMTQSPLS LPVTLGQPAS ISCRSSQSLV HRNGNTYLHW YLQRPGQSPR LLIYKVSNRF     60
SGVPDRFSGS GSGTDFTLKI SRVEAEDVGL YFCFQTTYVP NTFGGGTKLE IK            112

SEQ ID NO: 35               moltype = AA   length = 112
FEATURE                     Location/Qualifiers
REGION                      1..112
                            note = Synthetic Construct
```

```
source                  1..112
                        mol_type = protein
                        organism = synthetic construct
SEQUENCE: 35
DVVMTQSPLS LPVTLGQPAS ISCRSSQSLV HRNGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 36           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 36
DVVMTQSPLS LPVTLGQPAS ISCRSSQSLV HRSGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 37           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 37
DVVMTQSPLS LPVTLGQPAS ISCRSSQSLV HRQGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 38           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 38
DVVMTQSPLS LPVTLGQPAS ISCRSSQSLV HREGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 39           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 39
DVVMTQSPLS LPVTLGQPAS ISCRSSQSLV HRAGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 40           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 40
DVVMTQSPLS LPVTLGQPAS ISCRSSQSLV HRHGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 41           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 41
DVVMTQSPLS LPVTLGQPAS ISCRSSQSLV HRAGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 42           moltype = AA   length = 112
FEATURE                 Location/Qualifiers
REGION                  1..112
                        note = Synthetic Construct
source                  1..112
                        mol_type = protein
```

```
                        organism = synthetic construct
SEQUENCE: 42
DVVMTQSPLS LPVTLGQPAS ISCRSSQSLV HRVGNTYLHW FQQRPGQSPR LLIYKVSNRF    60
SGVPDRFSGS GSGTDFTLKI SRVEAEDVGV YFCFQTTYVP NTFGGGTKLE IK            112

SEQ ID NO: 43           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 43
QVQLQESGPG LVKPSETLSL TCTVSGFSLS SYGVSWIRQP PGKGLEWIGV IWGDGSTNYH    60
PNLMSRVTIS VDTSKNQFSL KLSSVTAADT AVYYCARLDY WGQGTSVTVS S             111

SEQ ID NO: 44           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 44
QVQLQESGPG LVKPSETLSL TCTVSGFSLS SYGVSWVRQP PGKGLEWLGV IWGDGSTNYH    60
PNLMSRVTIS VDTSKNQFSL KLSSVTAADT AVYYCARLDY WGQGTSVTVS S             111

SEQ ID NO: 45           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 45
QVQLQESGPG LVKPSETLSL TCTVSGFSLS SYGVSWIRQP PGKGLEWIGV IWGDGSTNYH    60
PNLMSRLSIS VDTSKNQFSL KLSSVTAADT ATYYCVTLDY WGQGTSVTVS S             111

SEQ ID NO: 46           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 46
QVQLQESGPG LVKPSETLSL TCTVSGFSLS SYGVSWVRQP PGKGLEWLGV IWGDGSTNYH    60
PNLMSRLSIS VDTSKNQFSL KLSSVTAADT AVYYCARLDY WGQGTSVTVS S             111

SEQ ID NO: 47           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 47
QVQLQESGPG LVKPSETLSL TCTVSGFSLS SYGVSWVRQP PGKGLEWLGV IWGDGSTNYH    60
PNLMSRLSIS VDTSKNQFSL KLSSVTAADT AVYYCVTLDY WGQGTSVTVS S             111

SEQ ID NO: 48           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 48
QVQLQESGPG LVKPSETLSL TCTVSGFSLS SYGVSWVRQP PGKGLEWLGV IWGDGSTNYH    60
PNLMSRLSIS KDTSKNQFSL KLSSVTAADT ATYYCVTLDY WGQGTSVTVS S             111

SEQ ID NO: 49           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 49
```

```
QVQLQESGPG LVKPSETLSL TCTVSGFSLS SYGVSWIRQP PGKGLEWIGV IWGDGSTNYH    60
PNLMSRVTIS KDTSKNQVLL KLSSVTAADT AVYYCVTLDY WGQGTSVTVS S             111

SEQ ID NO: 50           moltype = AA  length = 111
FEATURE                 Location/Qualifiers
REGION                  1..111
                        note = Synthetic Construct
source                  1..111
                        mol_type = protein
                        organism = synthetic construct
SEQUENCE: 50
QVQLQESGPG LVKPSETLSL TCTVSGFSLS SYGVSWIRQP PGKGLEWIGV IWGDGSTNYH    60
PNLMSRVTIS KDTSKSQFSL KLSSVTAADT AVYYCVTLDY WGQGTSVTVS S             111

SEQ ID NO: 51           moltype = AA  length = 111
FEATURE                 Location/Qualifiers
REGION                  1..111
                        note = Synthetic Construct
source                  1..111
                        mol_type = protein
                        organism = synthetic construct
SEQUENCE: 51
QVQLQESGPG LVKPSETLSL TCTVSGFSLS SYGVSWIRQP PGKGLEWLGV IWGDGSTNYH    60
PNLMSRVTIS VDTSKSQVLF KLSSVTAADT AVYYCATLDY WGQGTSVTVS S             111

SEQ ID NO: 52           moltype = AA  length = 111
FEATURE                 Location/Qualifiers
REGION                  1..111
                        note = Synthetic Construct
source                  1..111
                        mol_type = protein
                        organism = synthetic construct
SEQUENCE: 52
QVQLQESGPG LVKPSETLSL TCTVSGFSLS SYGVSWIRQP PGKGLEWLGV IWGDGSTNYH    60
PNLMSRLSIS KDTSKSQVLL KLSSVTAADT AVYYCVTLDY WGQGTSVTVS S             111

SEQ ID NO: 53           moltype = AA  length = 111
FEATURE                 Location/Qualifiers
REGION                  1..111
                        note = Synthetic Construct
source                  1..111
                        mol_type = protein
                        organism = synthetic construct
SEQUENCE: 53
QVQLQESGPG LVKPSETLSL TCTVSGFSLS SYGVSWIRQP PGKGLEWLGV IWGSGSTNYH    60
PNLMSRVTIS VDTSKSQVLF KLSSVTAADT AVYYCATLDY WGQGTSVTVS S             111

SEQ ID NO: 54           moltype = AA  length = 111
FEATURE                 Location/Qualifiers
REGION                  1..111
                        note = Synthetic Construct
source                  1..111
                        mol_type = protein
                        organism = synthetic construct
SEQUENCE: 54
QVQLQESGPG LVKPSETLSL TCTVSGFSLS SYGVSWIRQP PGKGLEWLGV IWGQGSTNYH    60
PNLMSRVTIS VDTSKSQVLF KLSSVTAADT AVYYCATLDY WGQGTSVTVS S             111

SEQ ID NO: 55           moltype = AA  length = 111
FEATURE                 Location/Qualifiers
REGION                  1..111
                        note = Synthetic Construct
source                  1..111
                        mol_type = protein
                        organism = synthetic construct
SEQUENCE: 55
QVQLQESGPG LVKPSETLSL TCTVSGFSLS SYGVSWIRQP PGKGLEWLGV IWGEGSTNYH    60
PNLMSRVTIS VDTSKSQVLF KLSSVTAADT AVYYCATLDY WGQGTSVTVS S             111

SEQ ID NO: 56           moltype = AA  length = 111
FEATURE                 Location/Qualifiers
REGION                  1..111
                        note = Synthetic Construct
source                  1..111
                        mol_type = protein
                        organism = synthetic construct
SEQUENCE: 56
QVQLQESGPG LVKPSETLSL TCTVSGFSLS SYGVSWIRQP PGKGLEWLGV IWGAGSTNYH    60
PNLMSRVTIS VDTSKSQVLF KLSSVTAADT AVYYCATLDY WGQGTSVTVS S             111
```

```
SEQ ID NO: 57              moltype = AA  length = 111
FEATURE                    Location/Qualifiers
REGION                     1..111
                           note = Synthetic Construct
source                     1..111
                           mol_type = protein
                           organism = synthetic construct
SEQUENCE: 57
QVQLQESGPG LVKPSETLSL TCTVSGFSLS SYGVSWIRQP PGKGLEWLGV IWGHGSTNYH    60
PNLMSRVTIS VDTSKSQVLF KLSSVTAADT AVYYCATLDY WGQGTSVTVS S             111

SEQ ID NO: 58              moltype = AA  length = 111
FEATURE                    Location/Qualifiers
REGION                     1..111
                           note = Synthetic Construct
source                     1..111
                           mol_type = protein
                           organism = synthetic construct
SEQUENCE: 58
QVQLQESGPG LVKPSETLSL TCTVSGFSLS SYGVSWIRQP PGKGLEWLGV IWGDASTNYH    60
PNLMSRVTIS VDTSKSQVLF KLSSVTAADT AVYYCATLDY WGQGTSVTVS S             111

SEQ ID NO: 59              moltype = AA  length = 111
FEATURE                    Location/Qualifiers
REGION                     1..111
                           note = Synthetic Construct
source                     1..111
                           mol_type = protein
                           organism = synthetic construct
SEQUENCE: 59
QVQLQESGPG LVKPSETLSL TCTVSGFSLS SYGVSWIRQP PGKGLEWLGV IWGDVSTNYH    60
PNLMSRVTIS VDTSKSQVLF KLSSVTAADT AVYYCATLDY WGQGTSVTVS S             111

SEQ ID NO: 60              moltype = AA  length = 111
FEATURE                    Location/Qualifiers
REGION                     1..111
                           note = Synthetic Construct
source                     1..111
                           mol_type = protein
                           organism = synthetic construct
SEQUENCE: 60
QVQLQESGPG LVKPSETLSL TCTVSGFSLS SYGVSWIRQP PGKGLEWLGV IWGDGSTNYH    60
PNLVSRVTIS VDTSKSQVLF KLSSVTAADT AVYYCATLDY WGQGTSVTVS S             111

SEQ ID NO: 61              moltype = AA  length = 111
FEATURE                    Location/Qualifiers
REGION                     1..111
                           note = Synthetic Construct
source                     1..111
                           mol_type = protein
                           organism = synthetic construct
SEQUENCE: 61
QVQLQESGPG LVKPSETLSL TCTVSGFSLS SYGVSWIRQP PGKGLEWLGV IWGDGSTNYH    60
PNLISRVTIS VDTSKSQVLF KLSSVTAADT AVYYCATLDY WGQGTSVTVS S             111

SEQ ID NO: 62              moltype = AA  length = 111
FEATURE                    Location/Qualifiers
REGION                     1..111
                           note = Synthetic Construct
source                     1..111
                           mol_type = protein
                           organism = synthetic construct
SEQUENCE: 62
QVQLQESGPG LVKPSETLSL TCTVSGFSLS SYGVSWIRQP PGKGLEWLGV IWGDGSTNYH    60
PNLLSRVTIS VDTSKSQVLF KLSSVTAADT AVYYCATLDY WGQGTSVTVS S             111

SEQ ID NO: 63              moltype = AA  length = 111
FEATURE                    Location/Qualifiers
REGION                     1..111
                           note = Synthetic Construct
source                     1..111
                           mol_type = protein
                           organism = synthetic construct
SEQUENCE: 63
QVQLQESGPG LVKPSETLSL TCTVSGFSLS SYGVSWIRQP PGKGLEWLGV IWGDGSTNYH    60
PNLASRVTIS VDTSKSQVLF KLSSVTAADT AVYYCATLDY WGQGTSVTVS S             111

SEQ ID NO: 64              moltype = AA  length = 16
```

```
FEATURE                    Location/Qualifiers
REGION                     1..16
                           note = Synthetic Construct
source                     1..16
                           mol_type = protein
                           organism = synthetic construct
SEQUENCE: 64
RSSQSLVHRS GNTYLH                                                              16

SEQ ID NO: 65              moltype = AA  length = 16
FEATURE                    Location/Qualifiers
REGION                     1..16
                           note = Synthetic Construct
source                     1..16
                           mol_type = protein
                           organism = synthetic construct
SEQUENCE: 65
RSSQSLVHRQ GNTYLH                                                              16

SEQ ID NO: 66              moltype = AA  length = 16
FEATURE                    Location/Qualifiers
REGION                     1..16
                           note = Synthetic Construct
source                     1..16
                           mol_type = protein
                           organism = synthetic construct
SEQUENCE: 66
RSSQSLVHRE GNTYLH                                                              16

SEQ ID NO: 67              moltype = AA  length = 16
FEATURE                    Location/Qualifiers
REGION                     1..16
                           note = Synthetic Construct
source                     1..16
                           mol_type = protein
                           organism = synthetic construct
SEQUENCE: 67
RSSQSLVHRA GNTYLH                                                              16

SEQ ID NO: 68              moltype = AA  length = 16
FEATURE                    Location/Qualifiers
REGION                     1..16
                           note = Synthetic Construct
source                     1..16
                           mol_type = protein
                           organism = synthetic construct
SEQUENCE: 68
RSSQSLVHRH GNTYLH                                                              16

SEQ ID NO: 69              moltype = AA  length = 16
FEATURE                    Location/Qualifiers
REGION                     1..16
                           note = Synthetic Construct
source                     1..16
                           mol_type = protein
                           organism = synthetic construct
SEQUENCE: 69
RSSQSLVHRN ANTYLH                                                              16

SEQ ID NO: 70              moltype = AA  length = 16
FEATURE                    Location/Qualifiers
REGION                     1..16
                           note = Synthetic Construct
source                     1..16
                           mol_type = protein
                           organism = synthetic construct
SEQUENCE: 70
RSSQSLVHRN VNTYLH                                                              16

SEQ ID NO: 71              moltype = AA  length = 16
FEATURE                    Location/Qualifiers
REGION                     1..16
                           note = Synthetic Construct
source                     1..16
                           mol_type = protein
                           organism = synthetic construct
SEQUENCE: 71
VIWGSGSTNY HPNLMS                                                              16
```

```
SEQ ID NO: 72              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 72
VIWGQGSTNY HPNLMS                                                          16

SEQ ID NO: 73              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 73
VIWGEGSTNY HPNLMS                                                          16

SEQ ID NO: 74              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 74
VIWGAGSTNY HPNLMS                                                          16

SEQ ID NO: 75              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 75
VIWGHGSTNY HPNLMS                                                          16

SEQ ID NO: 76              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 76
VIWGDASTNY HPNLMS                                                          16

SEQ ID NO: 77              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 77
VIWGDVSTNY HPNLMS                                                          16

SEQ ID NO: 78              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 78
VIWGDGSTNY HPNLVS                                                          16

SEQ ID NO: 79              moltype = AA   length = 16
FEATURE                    Location/Qualifiers
REGION                     1..16
                           note = Synthetic Construct
source                     1..16
                           mol_type = protein
                           organism = synthetic construct
SEQUENCE: 79
VIWGDGSTNY HPNLIS                                                          16
```

```
SEQ ID NO: 80            moltype = AA   length = 16
FEATURE                  Location/Qualifiers
REGION                   1..16
                         note = Synthetic Construct
source                   1..16
                         mol_type = protein
                         organism = synthetic construct
SEQUENCE: 80
VIWGDGSTNY HPNLLS                                                           16

SEQ ID NO: 81            moltype = AA   length = 16
FEATURE                  Location/Qualifiers
REGION                   1..16
                         note = Synthetic Construct
source                   1..16
                         mol_type = protein
                         organism = synthetic construct
SEQUENCE: 81
VIWGDGSTNY HPNLAS                                                           16

SEQ ID NO: 82            moltype = AA   length = 8
FEATURE                  Location/Qualifiers
REGION                   1..8
                         note = Synthetic Construct
source                   1..8
                         mol_type = protein
                         organism = synthetic construct
SEQUENCE: 82
DVVMTQTP                                                                     8

SEQ ID NO: 83            moltype = AA   length = 5
FEATURE                  Location/Qualifiers
REGION                   1..5
                         note = Synthetic Construct
source                   1..5
                         mol_type = protein
                         organism = synthetic construct
SEQUENCE: 83
VSPSV                                                                        5

SEQ ID NO: 84            moltype = AA   length = 10
FEATURE                  Location/Qualifiers
REGION                   1..10
                         note = Synthetic Construct
source                   1..10
                         mol_type = protein
                         organism = synthetic construct
SEQUENCE: 84
VSPSVVSPSV                                                                  10

SEQ ID NO: 85            moltype = AA   length = 5
FEATURE                  Location/Qualifiers
REGION                   1..5
                         note = Synthetic Construct
source                   1..5
                         mol_type = protein
                         organism = synthetic construct
SEQUENCE: 85
GGSGG                                                                        5

SEQ ID NO: 86            moltype = AA   length = 10
FEATURE                  Location/Qualifiers
REGION                   1..10
                         note = Synthetic Construct
source                   1..10
                         mol_type = protein
                         organism = synthetic construct
SEQUENCE: 86
GGGGSGGGGS                                                                  10

SEQ ID NO: 87            moltype = AA   length = 255
FEATURE                  Location/Qualifiers
REGION                   1..255
                         note = Synthetic Construct
source                   1..255
                         mol_type = protein
                         organism = synthetic construct
SEQUENCE: 87
```

```
APGGGRAQRA QARQARQAQR AQRAQARQAR QVSPSVDVVM TQSPLSLPVT LGQPASISCR    60
SSQSLVHRSG NTYLHWFQQR PGQSPRLLIY KVSNRFSGVP DRFSGSGSGT DFTLKISRVE   120
AEDVGVYFCF QTTYVPNTFG GGTKLEIKRT VAAPSVFIFP PSDEQLKSGT ASVVCLLNNF   180
YPREAKVQWK VDNALQSGNS QESVTEQDSK DSTYSLSSTL TLSKADYEKH KVYACEVTHQ   240
GLSSPVTKSF NRGEC                                                   255

SEQ ID NO: 88              moltype = AA   length = 219
FEATURE                    Location/Qualifiers
REGION                     1..219
                           note = Synthetic Construct
source                     1..219
                           mol_type = protein
                           organism = synthetic construct
SEQUENCE: 88
DVVMTQSPLS LPVTLGQPAS ISCRSSQSLV HRSGNTYLHW FQQRPGQSPR LLIYKVSNRF    60
SGVPDRFSGS GSGTDFTLKI SRVEAEDVGV YFCFQTTYVP NTGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 89              moltype = AA   length = 250
FEATURE                    Location/Qualifiers
REGION                     1..250
                           note = Synthetic Construct
source                     1..250
                           mol_type = protein
                           organism = synthetic construct
SEQUENCE: 89
DVVMTQSPLS LPVTLGQPAS ISCRSSQSLV HRSGNTYLHW FQQRPGQSPR LLIYKVSNRF    60
SGVPDRFSGS GSGTDFTLKI SRVEAEDVGV YFCFQTTYVP NTGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGECV SPSVRAQRAQ ARQARQAQRA   240
QRAQARQARQ                                                         250

SEQ ID NO: 90              moltype = AA   length = 255
FEATURE                    Location/Qualifiers
REGION                     1..255
                           note = Synthetic Construct
source                     1..255
                           mol_type = protein
                           organism = synthetic construct
SEQUENCE: 90
DVVMTQSPLS LPVTLGQPAS ISCRSSQSLV HRSGNTYLHW FQQRPGQSPR LLIYKVSNRF    60
SGVPDRFSGS GSGTDFTLKI SRVEAEDVGV YFCFQTTYVP NTGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGECG GGSGGGGSR AQRAQARQAR   240
QAQRAQRAQA RQARQ                                                   255

SEQ ID NO: 91              moltype = AA   length = 441
FEATURE                    Location/Qualifiers
REGION                     1..441
                           note = Synthetic Construct
source                     1..441
                           mol_type = protein
                           organism = synthetic construct
SEQUENCE: 91
QVQLQESGPG LVKPSETLSL TCTVSGFSLS SYGVSWIRQP PGKGLEWLGV IWGEGSTNYH    60
PNLMSRVTIS VDTSKSQVLF KLSSVTAADT AVYYCATLDY WGQGTSVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDKKVE PKSCDKTHTC PPCPAPELLG GPSVFLFPPK   240
PKDTLMISRT PEVTCVVVDV SHEDPEVKFN WYVDGVEVHN AKTKPREEQY NSTYRVVSVL   300
TVLHQDWLNG KEYKCKVSNK ALPAPIEKTI SKAKGQPREP QVYTLPPSRD ELTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                            441

SEQ ID NO: 92              moltype = AA   length = 472
FEATURE                    Location/Qualifiers
REGION                     1..472
                           note = Synthetic Construct
source                     1..472
                           mol_type = protein
                           organism = synthetic construct
SEQUENCE: 92
QVQLQESGPG LVKPSETLSL TCTVSGFSLS SYGVSWIRQP PGKGLEWLGV IWGEGSTNYH    60
PNLMSRVTIS VDTSKSQVLF KLSSVTAADT AVYYCATLDY WGQGTSVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDKKVE PKSCDKTHTC PPCPAPELLG GPSVFLFPPK   240
```

-continued

```
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KVSPSVRAQR AQARQARQAQ RAQRAQARQA RQ          472
```

ANTIBODY-PEPTIDE FUSION PROTEINS FOR TREATING AMYLOID DISORDERS

CROSS-REFERENCE TO RELATED APPLICATIONS

This application is a continuation of International Application No. PCT/US2022/072413, filed on May 18, 2022, which claims priority from U.S. provisional application No. 63/190,191, filed May 18, 2021 the contents of which are incorporated by reference in their entirety.

SUBMISSION OF SEQUENCE LISTING ON ASCII TEXT FILE

The content of the electronic sequence listing (165992000601SEQLIST.xml; Size: 118,359 bytes; and Date of Creation: Mar. 9, 2023) is herein incorporated by reference in its entirety.

FIELD OF THE INVENTION

This application relates to antibody-peptide fusion proteins that bind to human amyloid fibrils, and methods of using the same.

BACKGROUND

Amyloidosis is a fatal protein-folding disorder characterized by the aggregation and deposition of proteinaceous fibrils and heparan sulfate proteoglycan in vital organs and tissues (Merlini, G. et al. (2003) N. Engl. J. Med. 349, 583-596; Merlini, G. et al. (2004) J. Intern. Med. 255, 159-178; De Lorenzi, E. et al. (2004) Curr. Med. Chem. 11, 1065-1084; Merlini, G. (2004) Neth. J. Med. 62, 104-105). The unrelenting accumulation of amyloid invariably leads to organ dysfunction and severe morbidity or death. The deposits can be cerebral, as in patients with Alzheimer's, Huntington's or prion diseases, or peripheral such as seen in patients with light chain-associated (AL) amyloidosis, transthyretin-associated (ATTR) amyloidosis, and type 2 diabetes. Further sub-grouping into localized or systemic indicates whether the precursor protein is produced locally (at the site of deposition) or circulates in the blood stream and deposits at distant anatomic sites, respectively (Westermark, P. et al. (2007) Amyloid. 14, 179-183). Amyloid can affect any organ or tissue but the kidneys, pancreas, liver, spleen, nervous tissue and heart constitute the major sites of deposition in patients with familial or sporadic forms of systemic amyloidosis. Alzheimer's disease currently affects more than 4 million Americans and this figure is estimated to increase to more than 16 million by the year 2050. It is by far the most common form of amyloidosis generally considered orphan disorders but are widely underdiagnosed with estimates of more than 200,000 cases in the US.

Of these, the major peripheral amyloidosis is transthyretin-associated (ATTR) amyloidosis followed by light chain-associated (AL) amyloidosis. The former results from the deposition of wild type (sporadic) or variant transthyretin (hereditary) and clinically manifests predominantly in peripheral nerves and heart; however musculoskeletal involvement is common and may precede organ deposition by decades. The latter is, a sporadic monoclonal plasma cell dyscrasia resulting in the deposition of fibrils composed of immunoglobulin light chain proteins. AL accounts for approximately two thirds of all peripheral amyloid cases and has a calculated incidence of ~1.4 per 100,000 persons per year in the USA, which is comparable to that of acute lymphocytic and chronic myeloid leukemia (Group, U. S. C. S. W. (2007) United States Cancer Statistics: 1999-2003 Incidence and Mortality Web-Based Report, U.S. Department of Health and Human Services Centers for Disease Control and Prevention National Cancer Institute, Atlanta). Although AL is one fifth as common as the related plasma cell dyscrasia multiple myeloma it is arguably more devastating with a median survival of only 13.2 months due partly to the rapidly progressive nature of the organ destruction, the lack of effective anti-amyloid therapeutics and the inability to effectively diagnose the disease before organ failure occurs. Fewer than 5% of all AL patients survive 10 years or more from the time of diagnosis (Comenzo, R. L. et al. (2002) Blood 99, 4276-4282). Moreover, in patients with cardiac AL amyloidosis the median survival is less than 5 months.

ATTR is a form of systemic amyloidosis. 25% of patients with ATTR amyloidosis dies within 24 months of diagnosis. (Gertz and Dispenzieri JAMA 324(1)79-89 (2002).) Current therapies do not prevent organ damage. ATTR amyloidosis is caused by transtheryretin (TTR) fibrils. Transthyretin is a protein made by the liver that helps carry thyroid hormone and vitamin A in the blood. Normally, TTR is a tetramer made up of 4 single-chain monomers. In hereditary ATTR amyloidosis, TTR gene mutations are thought to destabilize the protein and cause tetramer dissociation into monomers, which aggregate into amyloid fibrils. In wild-type ATTR amyloidosis, the normal TTR protein becomes unstable, misfolds, and forms amyloid fibrils.

These amyloid fibrils then accumulate in multiple organs throughout the body For example, the wrist, in a narrow pathway called the carpal tunnel. This can cause carpal tunnel syndrome, which causes your hand and arm to become numb and tingle. The spinal canal, which can cause narrowing of the spinal column (spinal stenosis). The heart, which can cause heart failure and/or an irregular heart rhythm called atrial fibrillation.

Another prevalent form of peripheral amyloidosis in the U.S. is inflammation-associated (AA) amyloidosis, which is associated with chronic inflammatory disorders such as arthritis, tuberculosis and Familial Mediterranean Fever. The incidence of AA is greatest in certain regions of Europe and the frequency varies among ethnic groups (Buck, F. S. et al. (1989) Mod. Pathol. 2, 372-377). In areas where Familial Mediterranean Fever is prevalent and goes untreated, the incidence of AA can be 100%. In Europe the incidence, based on autopsy studies performed in the Denmark, is estimated to be 0.86% (Lofberg, H. et al. (1987) Acta pathologica, microbiologica, et immunologica Scandinavica 95, 297-302); however, in patients with rheumatoid or psoriatic arthritis the occurrence of AA can be as high as 26%. Such a high prevalence may warrant a screening program to detect the disease earlier. Deposition of amyloid is associated with a sustained increase in the plasma concentration of serum amyloid protein A (sAA), the precursor of the amyloid fibrils (Rocken, C. et al. (2002) Virchows Arch. 440, 111-122). AA differs from AL in the type of precursor protein that is deposited but both share common mechanistic features associated with fibril formation and deposition (Rocken, C. et al. (2006) J. Pathol. 210, 478-487; Rocken, C. et al. (2001)Am. J. Pathol. 158, 1029-1038).

In addition to the disorders in which the etiopathology of amyloid is well established, fibrillar deposits with the structural and tinctorial properties of amyloid have been identified in other syndromes although their relevance to the disease state has yet to be established. In type 2 diabetes for example, islet amyloid precursor protein (IAPP) deposits as amyloid in the Islets of Langerhans (Jaikaran, E. T. et al. (2001) *Biochim. Biophys. Acta* 1537, 179-203). The aggregation of IAPP results in oligomeric structures that are toxic to pancreatic cells (Lin, C. Y. et al. (2007) *Diabetes* 56, 1324-1332). Thus, it is suggested that the formation of IAPP amyloid in type 1 diabetic patients contributes to β cell destruction and ushers in the transition to insulin dependence (Jaikaran, E. T. et al. (2001) *Biochim. Biophys. Acta* 1537, 179-203). In another example, plaques containing amyloid fibrils composed of apolipoprotein A-I have been identified in over half of patients with atherosclerotic carotid arteries (Westermark, P. et al. (1995) *Am. J. Pathol.* 147, 1186-1192; Mucchiano, G. I. et al. (2001) *J. Pathol.* 193, 270-275). The deposition of these fibrils was more common in older patients but apoA-I is undoubtedly present early in plaque development (Vollmer, E. et al. (1991) *Virchows Arch. A. Pathol. Anat. Histopathol.* 419, 79-88). As a final example, Apo-A-I amyloid was also recently identified in knee joint menisci obtained from patients having knee replacement surgery and may contribute to the physical deterioration of the joint (Solomon, A. et al. (2006) *Arthritis Rheum.* 54, 3545-3550).

In total, more than 29 proteins have been chemically or serologically identified as constituents of fibrils in amyloid deposits. It is the nature of these proteins that differentiate the diseases, determine the treatment, and establish the prognosis. Although amyloid fibrils are associated with a clinically heterogeneous group of diseases and can form from structurally distinct and functionally diverse precursor proteins, the deposits themselves share a number of remarkably similar characteristics including fibril structure, fibril epitopes and accrual of similar accessory molecules including heparan sulfate proteoglycans (HSPGs). Amyloid is a heterogeneous complex that includes, in addition to fibrils, glycosaminoglycans (GAGs) and in particular the perlecan HSPG (Ancsin, J. B. (2003) *Amyloid* 10, 67-79; Ailles, L. et al. (1993) *Lab. Invest.* 69, 443-448; Kisilevsky, R. (1994) *Mol. Neurobiol.* 9, 23-24; Kisilevsky, R. (1990) *Lab. Invest.* 63, 589-591; Snow, A. D. et al. (1987) *Lab. Invest.* 56, 120-123; Li, J. P. et al. (2005) *Proc. Natl. Acad. Sci. USA* 102, 6473-6477).

To date, the most effective therapeutic intervention for removing amyloid deposits, which may promote recovery of organ function and lead to an improved prognosis, involves the use of amyloid-reactive antibodies as a means of immunotherapy. Several immunotherapies (antibodies) have been developed for amyloid-related diseases, including monoclonal antibody 11-1F4 for the treatment of AL amyloidosis, NEOD001 for patients with AL amyloidosis, GSK2398852 (anti-SAP monoclonal antibody) for amyloidosis, Solanezumab for Alzheimer's disease, intravenous IgG (IVIG) for Alzheimer's disease, and Bapineuzumab for Alzheimer's Alzheimer's disease. And Aducamumab for Alzheimer's disease. Each of these approaches has limitations or did not meet primary outcomes in late stage clinical trials (Phase 2/3).

Accordingly, there is a need for effective treatments for amyloidosis and amyloid related diseases.

SUMMARY OF THE INVENTION

Provided herein are antibody-peptide fusion proteins comprising an amyloid-reactive peptide linked to an antibody, as well as methods of making and using the like.

In one aspect, provided herein is an antibody-peptide fusion protein, comprising: an amyloid-reactive peptide; and an antibody that binds to amyloid fibrils, wherein the antibody comprises a heavy chain comprising a heavy chain variable region (VH) and a light chain comprising a light chain variable region (VL), wherein the amyloid-reactive peptide and the antibody are linked at the N-terminal end or the C-terminal end of the heavy chain or the light chain, wherein the amyloid-reactive peptide is linked to the antibody via a spacer comprising an amino acid sequence selected from the group consisting of SEQ ID NOs: 23-24, 27, 83-86. In some embodiments, the antibody binds to human amyloid fibrils.

In some embodiments, the amyloid-reactive peptide and the antibody are linked at the C-terminal end of the light chain.

In some embodiments, the spacer is selected from the group consisting of SEQ ID NO: 83 and SEQ ID NO: 86.

In some embodiments, the light chain further comprises a light chain constant region, and the heavy chain comprises a heavy chain constant region.

In some embodiments, the amyloid-reactive peptide comprises an amino acid sequence having at least 85%, 90%, 95%, 96%, 97%, 98%, 99%, 99.5%, or 100% sequence identity to any one of the amino acid sequences set forth as SEQ ID NOs: 1-13.

In some embodiments, the antibody-peptide fusion protein comprises two heavy chains and two light chains and wherein each light chain is linked at its C-terminus with an amyloid-reactive peptide.

In some embodiments, the antibody is a chimeric antibody or humanized antibody.

In some embodiments, the VL comprises a CDR-LT comprising the amino acid sequence set forth in SEQ ID NOs: 64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO: 18, and a CDR-H3 comprising the amino acid sequence set forth in SEQ ID NO:19. In some embodiments, the VL comprises a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NOs: 71-81; and a CDR-H3 comprising the amino acid sequence set forth in SEQ ID NO: 19. In some embodiments, the VL comprises a CDR-LT comprising the amino acid sequence set forth in SEQ ID NOs: 64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NOs: 71-81; and a CDR-H3 comprising the amino acid sequence set forth in SEQ ID NO: 19.

In some embodiments, the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO:19.

In some embodiments, the VL comprises an amino acid sequence set forth in SEQ ID NO:34, and the VH comprises an amino acid sequence set forth in SEQ ID NO:48. In some embodiments, the VL comprises an amino acid sequence set forth in SEQ ID NO:35, and the VH comprises an amino acid sequence set forth in SEQ ID NO:51. In some embodiments, the VL comprises an amino acid sequence set forth in SEQ ID NO:36, and the VH comprises an amino acid sequence set forth in SEQ ID NO:55. In some embodiments, the VL comprises an amino acid sequence set forth in SEQ ID NO:35, and the VH comprises an amino acid sequence set forth in SEQ ID NO:52. In some embodiments, the VL comprises an amino acid sequence set forth in SEQ ID NO:35, and the VH comprises an amino acid sequence set forth in SEQ ID NO:50. In some embodiments, the VL comprises an amino acid sequence set forth in SEQ ID NO:35, the VH comprises an amino acid sequence set forth in SEQ ID NO:49.

In some embodiments, the VL comprises an amino acid sequence set forth in SEQ ID NO:36, and the VH comprises an amino acid sequence set forth in SEQ ID NO:55.

In some embodiments, the antibody is a full-length antibody. In some embodiments, the antibody comprises an Fc region. In some embodiments, the Fc region is of an IgG1, IgG2, IgG3, or IgG4 isotype. In some embodiments the antibody is an IgG1 isotype.

In another aspect, provided herein is an antibody-peptide fusion protein, comprising an antibody that binds to amyloid fibrils comprising a first polypeptide and a second polypeptide each comprising a light chain of the antibody, and a third and a fourth polypeptide each comprising a heavy chain of the antibody, and an amyloid-reactive peptide that is linked to the N-terminus or the C-terminus of the light chain or the heavy chain, wherein the first polypeptide and second polypeptide comprise the amino acid set forth in SEQ ID NO:87, and the third and fourth polypeptide comprise the amino acid sequence set forth in SEQ ID NO:91. In some embodiments, the first polypeptide and second polypeptide comprise the amino acid set forth in SEQ ID NO:88, and the third and fourth polypeptide comprise the amino acid sequence set forth in SEQ ID NO:92. In some embodiments, the first polypeptide and second polypeptide comprise the amino acid set forth in SEQ ID NO:89, and the third and fourth polypeptide comprise the amino acid sequence set forth in SEQ ID NO:91. In some embodiments, the first polypeptide and second polypeptide comprise the amino acid set forth in SEQ ID NO:90, and the third and fourth polypeptide comprise the amino acid sequence set forth in SEQ ID NO:91.

In another aspect, provided herein is an antibody-peptide fusion protein, comprising an amyloid-reactive peptide comprising the amino acid sequence set forth in SEQ ID NO:1 or SEQ ID NO:2; and an antibody that binds to a human amyloid fibrils wherein the antibody comprises a variable heavy chain (VH) and a variable light chain (VL) wherein the VH comprises a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO:19, and the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22; wherein the amyloid-reactive peptide and antibody are linked at the C-terminal end of the light chain, wherein the amyloid-reactive peptide is linked to the antibody via a spacer comprising an amino acid sequence selected from the group consisting of SEQ ID NOs: 23-24, 27, 83-86.

In another aspect, provided herein is an antibody-peptide fusion protein, comprising an amyloid-reactive peptide comprising the amino acid sequence set forth in SEQ ID NO:2; and an antibody that binds to a human amyloid fibrils wherein the antibody comprises a variable heavy chain (VH) and a variable light chain (VL) wherein the VH comprises a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO:19, and the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22; wherein the amyloid-reactive peptide and antibody are linked at the C-terminal end of the light chain, wherein the amyloid-reactive peptide is linked to the antibody via a spacer comprising the amino acid sequence set forth in SEQ ID NO:83.

In some embodiments, the antibody-peptide fusion protein exhibits an EC50 less than 1.5 nM for an amyloid substrate.

In some embodiments, the antibody-peptide fusion protein is conjugated to a detectable label wherein the detectable label comprises a fluorescent label or a radiolabel. In some embodiments, the radiolabel is I-123, I-124, F-18, ZR-89, or Tc-99m.

In some embodiments, the antibody-peptide fusion protein exhibits one or more in vivo features selected from among improved biodistribution, pan amyloid reactivity, and enhanced phagocytosis compared to a reference IgG antibody.

In some embodiments, the antibody-peptide fusion protein binds to rVλ6Wil, Aβ, Aβ(1-40), IAAP, ALκ4, Alλ1, ATTR, α-synuclein, or Tau 441 fibrils.

In another aspect, provided herein is a composition comprising an antibody-peptide fusion protein, comprising i) an amyloid-reactive peptide; and ii) an antibody, wherein the antibody comprises a heavy chain comprising a heavy chain variable region (VH) and a light chain comprising a light chain variable region (VL), wherein the amyloid-reactive peptide and antibody are linked at the C-terminal end of the light chain, wherein the amyloid-reactive peptide is linked to the antibody via a spacer, or without a spacer; and wherein at least 90% of the antibody-peptide fusion protein is intact. In some embodiments, the antibody is a full length antibody.

In some embodiments, the composition comprises no more than 10% of a cleavage product, wherein the cleavage product comprises a VH lacking one or more amino acid residues from the N-terminus or C-terminus compared to the amino acid sequence set forth by SEQ ID NO:89 and a VL lacking one or more amino acid residues from the N-terminus or C-terminus compared to the amino acid sequence set forth in SEQ ID NO:91.

In some embodiments, the antibody-peptide fusion protein exhibits an EC50 binding affinity for one or more amyloid substrate, wherein the EC50 binding affinity is less than 1.5 nM.

In some embodiments, the composition further comprises a pharmaceutically acceptable carrier.

In another aspect, provided herein is a polynucleotide encoding the antibody-peptide fusion protein. In another aspect, provided herein is a vector comprising the polynucleotide. In another aspect, provided herein is a host cell comprising the vector of. In some embodiments, the host cell is a mammalian cell, optionally a Chinese hamster ovary (CHO) cell.

In another aspect, provided herein is a method of producing an antibody-peptide fusion protein comprising a) culturing a host cell comprising a vector encoding an antibody-peptide fusion protein under perfusion cell culture conditions suitable for expression of the antibody-peptide fusion protein; and b) recovering the antibody-peptide fusion protein about every 12-36 hours; wherein the antibody-peptide fusion protein comprises i) an amyloid-reactive peptide; and ii) an antibody, wherein the antibody comprises a heavy chain comprising a heavy chain variable region (VH) and a light chain comprising a light chain variable region (VL), wherein the amyloid-reactive peptide and antibody are linked at the C-terminal end of the light chain, wherein the amyloid-reactive peptide is linked to the antibody via a spacer, or without a spacer. In some embodiments, the amyloid-reactive peptide is linked to C terminus of the constant domain of the antibody light chain.

In some embodiments, the method further comprises applying the antibody-peptide fusion recovered in step b) to a cation exchange chromatography column and eluting the antibody-peptide fusion protein from the cation exchange chromatography column.

In some embodiments, the antibody-peptide fusion protein is eluted separately from a truncated antibody-peptide fusion protein.

In some embodiments, the host cell is a CHO cell.

In some embodiments, the method further comprising determining the purity of the antibody-peptide fusion protein, wherein the purity of the antibody-peptide fusion protein is determined using one or more analytical methods comprising sodium dodecyl sulfate capillary electrophoresis (CE-SDS), liquid chromatography (LC), mass spectrometry (MS), or a combination thereof.

In some embodiments, the antibody-peptide fusion protein is purified to at least 90% intact antibody-peptide fusion protein.

In another aspect, provided herein is an antibody-peptide fusion protein produced by the method described herein.

In some aspects, provided herein is a method of treating a subject having an amyloid related disorder comprising an amyloid deposit, comprising administering to the subject a therapeutically effective amount of the antibody-peptide fusion protein. In some embodiments, the amyloid related disorder is systematic or localized amyloidosis. In some embodiments, the amyloid related disorder is selected from the group consisting of AL, AH, A02M, ATTR, transthyretin, AA, AApoAI, AApoAII, AGel, ALys, ALEct2, AFib, ACys, ACal, AMed, AIAPP, APro, AIns, APrP, Parkinson's disease, Alzheimer's disease, or AP amyloidosis.

In some embodiments, the amyloid deposit is opsonized by the antibody-peptide fusion protein. In some embodiments, treating the subject with the antibody-peptide fusion protein causes phagocytosis of the amyloid deposit. In some embodiments, treating the subject with the antibody-peptide fusion protein results in the improvement of one or more clinical features selected from the group comprising swelling of lower extremities, severe fatigue, severe weakness, shortness of breath, difficulty breathing, numbness, pain in your hands, wrists, or feet, diarrhea, constipation, unintentional weight loss, an enlarged tongue, skin changes, an irregular heartbeat, difficulty swallowing.

In another aspect, provided herein is a method of treating a subject having an amyloid-based disease or suspected of having an amyloid-based disease, comprising a) determining whether the subject has an amyloid deposit by i) administering the antibody-peptide fusion protein to the subject, wherein the antibody-peptide fusion protein comprises a detectable label, and ii) determining whether a signal associated with the detectable label can be detected from the subject; and b) if the signal is detected, administering to the subject an amyloidosis treatment.

In some embodiments, if a signal is not detected, monitoring the subject for a later development of an amyloid deposit. In some embodiments, the method further comprises determining the intensity of the signal and comparing the signal to a threshold value, above which the subject is determined to possess an amyloid deposit. In some embodiments, the antibody-peptide fusion protein is detected by SPECT/CT imaging, PET/CT imagining, gamma scintigraphy, or optical imaging.

In some embodiments, the amyloidosis treatment comprises administering the antibody-peptide fusion protein to the subject. In some embodiments, administration of the antibody-peptide fusion protein causes phagocytosis of amyloid deposit in the subject. In some embodiments, administration of the antibody-peptide fusion protein results in clearance of the amyloid deposit in the subject.

In another aspect, provided herein is a method of identifying an amyloid deposit in a subject, comprising administering the antibody-peptide fusion protein to the subject, wherein the antibody-peptide fusion protein comprises a detectable label, and detecting a signal from the antibody peptide fusion protein.

In another aspect, provided herein is a method of monitoring amyloid clearance in a subject comprising contacting the amyloid substrate in the subject with the antibody-peptide fusion protein, wherein the antibody-peptide fusion protein comprises a detectable label, and wherein the peptide of the antibody-peptide fusion protein has binding affinity for an amyloid substrate; and determining a signal from the detectable label, thereby detecting the amyloid clearance.

In some embodiments, the subject is a human.

In another aspect, provided herein is a kit comprising the antibody-peptide fusion protein, for use in a method provided herein.

BRIEF DESCRIPTION OF THE DRAWINGS

FIG. 7A shows pHrodo red-labeled rVλ6Wil fibril uptake by human THP-1 macrophages alone, or in the presence of human (h) IgG control, ch11-1F4, muIgp5 (produced in the expiHEK293 cell line), VH6/VL3-p5, or VH6/VL3-p5R, as indicated from left to right on the x-axis. The y-axis shows the level of rVλ6Wil fibril uptake (measured in fluorescent units), and the error bars represent the standard deviation.

FIGS. 12A-12D show the results of an ex vivo phagocytosis assay performed with PF.1 and human IgG1 (hIgG1) control for ALκ, ALλ, ATTRv, and ATTRwt amyloid extracts. Phagocytosis is detected by labeling with the pH sensitive dye succinimidyl-pHrodo red fluorophore where increasing fluorescence emission is indicative of enhanced phagocytosis. ATTRwt is a wild type transthyretin associated amyloidosis. ATTRv is a variant transthyretin associated amyloidosis.

FIG. 13A shows the results of a binding experiment testing the affinity of PF.1 on rVλWIL Aβ(1-40), ATTRwt, ATTRV, ALλ, and ALκ amyloid extracts. ATTRwt is a wild type transthyretin associated amyloidosis. ATTRv is a variant transthyretin associated amyloidosis. FIG. 13B shows results of a binding experiment testing the affinity of human IgG1 control for the same amyloid extract panel used in FIG. 12A.

DETAILED DESCRIPTION

Figure 1:
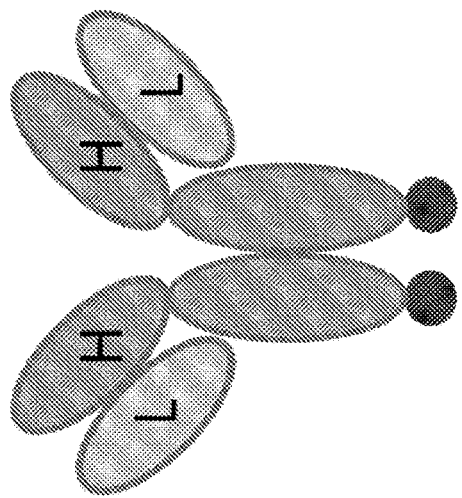
FIG. 1 shows a schematic diagram of an antibody-peptide fusion protein with the peptide fused to the N-terminus of the light chain via a short, rigid spacer

Provided herein are antibody-peptide fusion proteins that bind amyloids.

I. DEFINITIONS

As used herein, the singular forms "a," "an," and "the," refer to both the singular as well as plural, unless the context clearly indicates otherwise. The abbreviation, "e.g." is derived from the Latin exempli gratia, and is used herein to indicate a non-limiting example. Thus, the abbreviation "e.g." is synonymous with the term "for example." As used herein, the term "comprises" means "includes."

Ranges can be expressed herein as from "about" one particular value, and/or to "about" another particular value. When such a range is expressed, another aspect includes from the one particular value of the range and/or to the other particular value of the range. It will be further understood that the endpoints of each of the ranges are significant both in relation to the other endpoint, and independently of the other endpoint. Similarly, when values are expressed as approximations, by use of the antecedent "about," it will be understood that the particular value forms another aspect. In certain example embodiments, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about. Further, terms used herein such as "example," "exemplary," or "exemplified," are not meant to show preference, but rather to explain that the aspect discussed thereafter is merely one example of the aspect presented.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. In case of conflict, the present specification, including explanations of terms, will control. In addition, the materials, methods, and examples are illustrative only and not intended to be limiting.

To facilitate review of the various embodiments of this disclosure, the following explanations of specific terms are provided:

The terms amyloids, amyloid deposits, amyloid fibrils, and amyloid fibers refer to insoluble fibrous protein aggregates sharing specific structural traits. The protein aggregates have a tertiary structure, for example, that is formed by aggregation of any of several different proteins and that consists of an ordered arrangement of 3 sheets stacked perpendicular to a fiber axis. See Sunde et al., J. Mol. Biol. (1997) 273:729-39. Abnormal accumulation of amyloids in organs may lead to amyloidosis. Although they are diverse in their occurrence, all amyloids have common morphologic properties in that they stain with specific dyes such as Congo red and have a characteristic red-green birefringent appearance in polarized light after staining. Amyloids also share common ultrastructural features and common x-ray diffraction and infrared spectra.

Amyloidosis refers to a pathological condition or disease characterized by the presence of amyloids, such as the presence of amyloid deposits. "Amyloid diseases" or "amyloidosis" are diseases associated with the formation, deposition, accumulation or persistence of amyloid fibrils. Such diseases include, but are not limited to, Alzheimer's disease, Down's syndrome, hereditary cerebral hemorrhage with amyloidosis of the Dutch type, and cerebral beta-amyloid angiopathy. Other amyloid diseases such as systemic AA amyloidosis, AL amyloidosis, ATTR amyloidosis, ALect2 amyloidosis, and IAPP amyloidosis of type II diabetes are also amyloid diseases.

Amyloidogenic refers to producing or tending to produce amyloid deposits. For example, certain soluble monomeric proteins can undergo extensive conformational changes leading to their aggregation into well-ordered, unbranching, 8- to 10-nm wide fibrils, which culminate in the formation of amyloid aggregates. More than thirty proteins, for example, have been found to form amyloid deposits (or amyloids) in man. Not all proteins within the class of diverse proteins, such as immunoglobulin light chains, are capable of forming amyloid, i.e., some proteins are non-amyloidogenic, meaning that they do not tend to form amyloids. Other proteins of the class, however, can form amyloid deposits and are thus amyloidogenic. Furthermore, within the class of light chain protein, some may be deemed more "amyloidogenic" than others based upon the ease with which they form amyloid fibrils. Certain light chain proteins are deemed non-amyloidogenic or less amyloidogenic because of their inability to readily form amyloid fibrils in patients or in vitro.

Animal: Living multi-cellular vertebrate organisms, a category that includes, for example, mammals and birds. The term mammal includes both human and non-human mammals. Similarly, the term "subject" includes both human and veterinary subjects. In some examples a subject is a subject, such as a subject suffering from an amyloid disease.

Clearance: The terms "clear" or "clearance" refer to reducing or removing by a measurable degree. For example, the clearance of an amyloid deposit as described herein relates to reducing or removing the deposit to a measurable or discernable degree. Clearance may result in 100% removal, but is not required to. Rather, clearance may result in less than 100% removal, such as about 10%, 20%, 30%, 40%, 50%, 60% or more removal.

Conjugate: As used herein, the term "conjugate" refers to the product of coupling or joining of two or more materials, the resulting product having at least two distinct elements, such as at least two domains. The coupled materials may be the same or may be different. Such a coupling may be via one or more linking groups. A "protein conjugate," for example, results from the coupling of two or more amino acid sequences. A conjugate of two proteins, for example, results in a single protein that has a domain corresponding to each of the individually joined proteins.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain, Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains, The term "constant region" refers to the portion of an immunoglobulin molecule having a more conserved amino acid sequence relative to the other portion of the immunoglobulin, the variable domain, which contains the antigen binding site. The constant region contains the CR1, CR2 and CR3 domains (also termed CH1, CH2, and CH3; collectively, CH) of the heavy chain and the CHL (or CL or CL1) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md, (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains, The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody-fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fe" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association, In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CHI.) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckfhun, in *The Pharmacology of Monoclonal Antibodies*, vol. 113, Rosenburg and Moore eds., (Springer-Verlag, New York, 1994), pp. 269-315.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal." indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different, determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature*, 256:495-97 (1975); Hongo et al, *Hybridoma*, 0.1.4 (3): 253-260 (0.1995), Harlow et al., Antibodies: A Laboratory Manual, (Cold Spring Harbor Laboratory Press, 2nd ed. 1988); Hammerling et al, in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al, *Nature*, 352: 624-628 (1991); Marks et al, *J. Mol. Biol.* 222: 581-597 (1992); Sidhu et al, *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits 11 et al, *Proc. Natl. Acad. Sci. USA* 90: 2551 (1993); Jakobovits et al, *Nature* 362: 255-258 (1993); Bruggemann et al, *Year in Immunol* 7:33 (1993); U.S. Pat. Nos. 5,545,807; 5,545, 806; 5,569,825; 5,625,126; 5,633,425; and 5,661,016; Marks et al, *Bio/Technology* 10: 779-783 (1992); Lonberg et al, *Nature* 368: 856-859 (1994); Morrison, *Nature* 368: 812-813 (1994); Fishwild et al, *Nature Biotechnol.* 14: 845-851 (1996); *Neuberger, Nature Biotechnol* 14: 826 (1996); and Lonberg and Huszar, *Intern. Rev. Immunol* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al, *Proc. Natl Acad. Sci. USA* 81:6851-6855 (1984)). Chimeric antibodies include primatized antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a CDR of the recipient are replaced by residues from a CDR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al, *Nature* 321:522-525 (1986); Riechmann et al, *Nature* 332:323-329 (1988); and Presta, *Curr. Op. Struct. Biol* 2:593-596 (1992), See also, e.g., Vaswani and Hamilton, *Ann. Allergy, Asthma & Immunol.* 1: 105-115 (1998); Harris, *Biochem. Soc. Transactions* 23: 1035-1038 (1995); Hurle and Gross, *Curr. Op. Biotech.* 5:428-433 (1994): and U.S. Pat. Nos. 6,982,321 and 7,087, 409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al, *J. Mol. Biol.,* 222:581 (1991). Also available for the preparation of human monoclonal antibodies are methods described in Cole et al, *Monoclonal Antibodies and Cancer Therapy*, Alan R. Liss, p. 77 (1985); Boerner et al, *J. Immunol.,* 147(1):86-95 (1991). See also van Dijk and van de Winkel, *Curr. Opin. Pharmacol.,* 5: 368-74 (2001), Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al, *Proc. Natl. Acad.*

Sci. USA, 103:3557-3562 (2006) regarding human antibodies generated via a human B-cell hybridoma technology.

The term "complementarity-determining region" or "CDR," when used herein refers to the regions of an antibody-variable domain that bind to an epitope, such as human amyloid fibrils. Generally, antibodies comprise six CDRs; three in the VH (H1, H2, H3), and three in the VL (L1, L2, L3). In native antibodies, H3 and L3 display the most diversity of the six CDRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N J, 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of CDR delineations are in use and are encompassed herein. In some embodiments, the CDRs may be Kabat CDRs, which are based on sequence variability and are the most commonly used (Kabat et al., supra). In some embodiments, the CDRs may be Chothia CDRs. Chothia refers instead to the location of the structural loops (Chothia and Lesk *J. Mol. Biol.* 196:901-917 (1987)). In some embodiments, the CDRs may be AbM CDRs. The AbM CDRs represent a compromise between the Kabat CDRs and Chothia structural loops, and are used by Oxford Molecular's AbM antibody-modeling software. In some embodiments, the CDRs may be "contact" CDRs. The "contact" CDRs are based on an analysis of the available complex crystal structures. The residues from each of these CDRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

CDRs may comprise "extended CDRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (112), and 93-102, 94-102, or 95-102 (H3) in the VH. The variable-domain residues are numbered according to Kabat et al., supra, for each of these extended-CDR definitions.

"Framework" or "FR" residues are those variable domain residues other than the CDR residues as herein defined.

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of <1 M, <100 µM, <10 nM, <1 nM, or <0.1 nM. In certain embodiments, an antibody specifically binds to an epitope on a protein that is conserved among the protein from different species. In another embodiment, specific binding can include, but does not require exclusive binding.

Effective amount or Therapeutically effective amount: The amount of agent that is sufficient to prevent, treat (including prophylaxis), reduce and/or ameliorate the symptoms and/or underlying causes of any of a disorder or disease, for example to prevent, inhibit, and/or amyloidosis. In some embodiments, an "effective amount" is sufficient to reduce or eliminate a symptom of a disease. An effective amount can be administered one or more times. For example, an effective amount of a peptide is an amount that is sufficient to bind an amyloid. A peptide may be effective, for example, when parenterally administered in amounts above about 1 µg per kg of body weight to about 30 mg/kg.

Inhibit: To reduce by a measurable degree. Inhibition does not, for example, require complete loss of function or complete cessation of the aspect being measured. For example, inhibiting plaque formation can mean stopping further growth of the plaque, slowing further growth of the plaque, or reducing the size of the plaque.

Inhibiting or treating a disease: Inhibiting the full development of a disease or condition, for example, inhibiting amyloidosis. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

With regard to amyloid deposit formation, "inhibition" refers to the prevention of reduction in the formation of the amyloid deposit, such as when compared to a control. For example, inhibition may result in a reduction of about 10%, 20%, 30%, 40%, 50%, 60% or more of an amyloid deposit as compared to a control.

Label refers to any detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes. A protein that is "detectably-labeled," for example, means that the presence of the protein can be determined by a label associated with the protein.

Isolated: An "isolated" biological component, such as a peptide (for example one or more of the peptides disclosed herein), cell, nucleic acid, or serum samples has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a cell as well as chemically synthesized peptide and nucleic acids. The term "isolated" or "purified" does not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation, such as at least 50%, at least 60%, at least 70%, at least 80%, at least 90%, at least 95%, or even at least 99% of the peptide or protein concentration.

Join: As used herein, the term "join," "joined," "link," or "linked" refers to any method known in the art for functionally connecting proteins and/or protein domains. For example, one protein domain may be linked to another protein domain via a covalent bond, such as in a recombinant fusion protein, with or without intervening sequences or domains. Joined also includes, for example, the integration of two sequences together, such as placing two nucleic acid sequences together in the same nucleic acid strand so that the sequences are expressed together.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Nucleotide includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

cDNA refers to a DNA that is complementary or identical to an mRNA, in either single stranded or double stranded form.

Encoding refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Pharmaceutically acceptable carriers: The pharmaceutically acceptable carriers of use are conventional. *Remington's Pharmaceutical Sciences*, by E. W. Martin, Mack Publishing Co., Easton, PA, 19$^{th}$ Edition (1995), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced. In some examples, a peptide is one or more of the peptides disclosed herein.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene* 73: 237-244, 1988; Higgins & Sharp *CABIOS* 5: 151-153, 1989; Corpet et al. *Nuc. Acids Res.* 16, 10881-90, 1988; Huang et al. *Computer Appls. In the Biosciences* 8, 155-65, 1992; and Pearson et al. *Meth. Mol. Bio.* 24, 307-31, 1994. Altschul et al. (*J Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, MD) and on the Internet, for use in connection with the sequence analysis programs blastp, blastn, blastx, tblastn and tblastx.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. The term vector includes plasmids, linear nucleic acid molecules, and as described throughout adenovirus vectors and adenoviruses.

A subject or an individual refers to a mammal, for example, a human. The subject may be a human patient. A subject may be a patient suffering from or suspected of suffering from a disease or condition and may be in need of treatment or diagnosis or may be in need of monitoring for the progression of the disease or condition. The patient may also be in on a treatment therapy that needs to be monitored for efficacy. In some example embodiments, a subject includes an individual suffering from amyloidosis, such as Alzheimer's, Huntington's or prion diseases, or peripheral amyloidosis such as seen in patients with light chain (AL) amyloidosis and type 2 diabetes.

Preferably, residue positions which are not identical differ by conservative amino acid substitutions. The term "conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. (Bowie et al. *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); *Introduction to Protein Structure* (C. Branden and J. Tooze, eds., Garland Publishing, New York, N.Y. (1991)); and Thornton et al. *Nature* 354:105 (1991).

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of HI, 50-58 of H2, and 95-102 of H3. (See Almagro and Fransson, *Front. Biosci.* 13: 1619-1633 (2008).)

II. ANTIBODY-PEPTIDE FUSION PROTEINS

Provided herein are antibody-peptide fusion proteins that target amyloids. Such antibody-peptide fusion proteins include, for example, amyloid-reactive peptides that are linked to an antibody, such as through extension of the N-terminus or C-terminus of the light chain protein of the antibody, fragment thereof, antigen binding (Fab) region, or via or the N-terminus or C-terminus of the heavy chain of the antibody, thereby forming a peptide-antibody fusion, wherein the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. The antibody-peptide fusion proteins can be used to treat a subject having amyloidosis or suspected of having amyloidosis, for example, such as by administering the antibody-peptide fusion proteins to the subject.

In some embodiments, provided herein is an antibody-peptide fusion protein, comprising: an amyloid-reactive peptide; and an antibody that induces phagocytosis or acts as an opsonin. In some embodiments, an opsonin is a protein that binds to a target and induces phagocytosis of that target. In some embodiments, the opsonin comprises antibody or an antibody-peptide fusion protein. In some embodiments, the antibody-peptide fusion proteins provided herein act as opsonins by binding to amyloid and promoting phagocytosis of the amyloid. In some embodiments, the antibody comprises a heavy chain comprising a heavy chain variable region (VH) and a light chain comprising a light chain variable region (VL). In some embodiments, the amyloid-reactive peptide and the antibody are linked at the N- and/or C-terminal end of the light chain and/or the N- and/or C-terminal end of the heavy chain. In some embodiments, the antibody-peptide fusion protein comprises more than one amyloid-reactive peptide linked to the antibody. In some embodiments, the amyloid-reactive peptide is linked to the antibody via a spacer. In some embodiments, the amyloid-reactive peptide is linked to the antibody via a peptide spacer. In some embodiments, the amyloid-reactive peptide is linked to the antibody via a spacer comprising the amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide and antibody are linked at the N-terminal end of the light chain. In some embodiments, the amyloid-reactive peptide and antibody are linked at the C-terminal end of the light chain. In some embodiments, the amyloid-reactive peptide and antibody are linked at the N-terminal end of the light chain. In some embodiments, the amyloid-reactive peptide and antibody are linked at the C-terminal end of the heavy chain. In some embodiments, the antibody is a full length antibody. In some embodiment, the amyloid-reactive peptide comprises an amino acid sequence as shown in Table 1, below.

In some embodiments, the amyloid-reactive peptide antibody fusion comprises a heavy chain in N- to C-terminal direction comprising in order an amyloid reactive peptide, a spacer, a VH, a CH1, a CH2, and a CH3. In some embodiments, the amyloid-reactive peptide antibody fusion comprises a heavy chain in N- to C-terminal direction in order a VH, a CH1, a CH2, a CH3, a spacer, and an amyloid reactive peptide. In some embodiments, the amyloid-reactive peptide antibody fusion comprises a light chain in N- to C-terminal direction in order an amyloid reactive peptide, a spacer, a VL, and a CL. In some embodiments, the amyloid-reactive peptide antibody fusion comprises a light chain in N- to C-terminal direction in order a VL, and a CL, a spacer, and an amyloid reactive peptide.

TABLE 1

Exemplary Amyloid-Reactive Peptide Sequences

| Peptide | Primary sequence | SEQ ID NO |
|---------|------------------|-----------|
| P5 | KAQKA QAKQA KQAQK AQKAQ AKQAK Q | SEQ ID NO: 1 |
| P5R | RAQRA QARQA RQAQR AQRAQ ARQAR Q | SEQ ID NO: 2 |
| P8 | KAKAK AKAKA KAKAK | SEQ ID NO: 3 |
| P9 | KAQAK AQAKA QAKAQ AKAQA KQAK AQAK | SEQ ID NO: 4 |

TABLE 1-continued

Exemplary Amyloid-Reactive Peptide Sequences

| Peptide | Primary sequence | SEQ ID NO |
|---|---|---|
| P19 | KAQQA QAKQA QQAQK AQQAQ AKQAQ Q | SEQ ID NO: 5 |
| P20 | QAQKA QAQQA KQAQQ AQKAQ AQQAK Q | SEQ ID NO: 6 |
| P31 | KAQKA QAKQA KQAQK AQKAQ AKQAK Q | SEQ ID NO: 7 |
| P37 | KTVKT VTKVT KVTVK TVKTV TKVTK V | SEQ ID NO: 8 |
| P42 | VYKVK TKVKT KVKTK VKT | SEQ ID NO: 9 |
| P43 | AQAYS KAQKA QAKQA KQAQK AQKAQ AKAK Q | SEQ ID NO: 10 |
| P44 | AQAYA RAQRA QARQA RQAQR AQRAQ ARQAR Q | SEQ ID NO: 11 |
| P5 + 14 | KAQKA QAKQA KQAQK AQKAQ AKQAK QAQKA QKAQA KQAKQ | SEQ ID NO: 12 |
| P5R + 14 | RAQRA QARQA RQAQR AQRAQ ARQAR QAQRA QRAQA RQARQ | SEQ ID NO: 13 |

Without wishing to be bound by any particular theory, it is believed that the amyloid-reactive peptide of the antibody-peptide fusion protein, when administered to a subject, targets the antibody-peptide fusion protein to the amyloid deposits. The Fc domain then triggers an immune response at the site of the amyloid, thereby resulting in removal of the amyloid, such as by opsonization. In addition, the antibody-peptide fusion protein is believed to have a longer half-life than the amyloid-reactive peptides alone. For example, the circulating half-life of an IgG in humans is approximately 21 days whereas the half-life of the amyloid-reactive peptide alone in humans is approximatively, 11 hours. Thus, the Ig enhances the half-life of the antibody-peptide fusion protein in circulation. In some embodiments, the half-life of the antibody-peptide fusion protein is increased by about 10%, 20%, 30%, 40%, 50%, 60%, 70%, 80% or more as compared to the amyloid-reactive peptide alone. As such, the antibody-peptide fusion protein, when administered to a subject, can exert its immunostimulatory effects longer at the site of the amyloid deposit, thereby increasing the immune response at the site of the amyloid deposit.

In some embodiments, the amyloid-reactive peptides of the antibody-peptide fusion proteins described herein comprises an amino acid sequence that is at least 80%, 85%, 90% or more identical to the amino acid sequence set forth as any one of SEQ ID NOS: 1-13, such as at least 95%, at least 96%, at least 97%, at least 98%, at least 99%, or 100% identical to the amino acid sequence set forth as any one of SEQ ID NOS: 1-13. In some embodiments, the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptides linked to the antibody or functional fragments thereof may comprise or consist of from about 10 to about 55 amino acids. The amyloid-reactive peptides of the present invention may, for example, comprise or consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. Such peptides are described, for example, in international patent application WO2016032949 and Wall et al. (*PLoS One*. 2013 Jun. 4; 8(6):e66181), which are hereby incorporated herein in their entirety. In some embodiments, the amyloid-reactive peptide comprises an amino acid sequence having at least 80%, 85%, 90%, 95% or more sequence identity to any one of the amino acid sequences set forth as SEQ ID NOs: 1-13. In some embodiments, the amyloid-reactive peptide comprises an amino acid sequence having at least 80%, 85%, 90%, 95% or more sequence identity to any one of the amino acid sequences set forth as SEQ ID NOs: 1-13. In some embodiments, the amyloid-reactive peptide comprises the amino acid sequences set forth as SEQ ID NOs: 1-13 comprising one or more amino acid substitutions. In some embodiments, the amyloid-reactive peptide comprises an amino acid sequence set forth in SEQ ID NO: 1. In some embodiments, the amyloid-reactive peptide comprises an amino acid sequence set forth in SEQ ID NO: 2. In some embodiments, the amyloid-reactive peptide comprises an amino acid sequence set forth in SEQ ID NO:12. In some embodiments, the amyloid-reactive peptide comprises an amino acid sequence set forth in SEQ ID NO: 13. In some embodiments, the amyloid-reactive peptide comprises the amino acid sequence set forth in any one or SEQ ID NOs:1-13.

The amino acids forming all or a part of the amyloid-reactive peptides bound to the antibody or fragment thereof may be stereoisomers and modifications of naturally occurring amino acids, non-naturally occurring amino acids, post-translationally modified amino acids, enzymatically synthesized amino acids, derivatized amino acids, constructs or structures designed to mimic amino acids, and the like. The amino acids forming the peptides of the present invention may be one or more of the 20 common amino acids found in naturally occurring proteins, or one or more of the modified and unusual amino acids. The antibody-peptide fusion protein may be made by any technique known to those of skill in the art, including chemical synthesis or recombinant means using standard molecular biological techniques.

In some embodiments, the antibody-peptide fusion protein comprises an antibody linked to an amyloid-reactive peptide. In some embodiments, the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the antibody that comprises one, two, three, four, five, or six CDRs of an antibody as shown in Table 2.

TABLE 2

Amino acid sequences of m11-1F4 CDRs

| 11-1F4 CDR | Amino Acid Sequence | SEQ ID NO |
|---|---|---|
| CDR-H1 | GFSLSSYGVS | 17 |
| CDR-H2 | VIWGDGSTNYHPNLMS | 18 |
| CDR-H3 | LDY | 19 |
| CDR-L1 | RSSQSLVHRNGNTYLH | 20 |
| CDR-L2 | KVSNRES | 21 |
| CDR-L3 | FQTTYVPNT | 22 |

In a particular embodiment, the antibody-peptide fusion protein comprises an antibody, wherein the antibody comprises a VH that comprises (a) a CDR-H1 comprising the amino acid sequence of SEQ ID NO:17, (b) a CDR-H2 comprising the amino acid sequence of SEQ ID NO:18, and (c) a CDR-H3 comprising the amino acid sequence of SEQ ID NO: 19, wherein the antibody is linked to a amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In a particular embodiment, the antibody-peptide fusion protein comprises an antibody, wherein the antibody comprises a VL that comprises (a) a CDR-L1 comprising the amino acid sequence of SEQ ID NO:20; (b) a CDR-L2 comprising the amino acid sequence of SEQ ID NO:21; and (c) a CDR-L3 comprising the amino acid sequence of SEQ ID NO:22, wherein the antibody is linked to a amyloid-reactive peptide via a spacer comprising an amino acid sequence selected from the group consisting of SEQ ID NOs: 23-24, 27, 83-86.

In one embodiment, the antibody-peptide fusion protein comprises an antibody that comprises a VL comprising the amino acid sequence of SEQ ID NO: 16 and a VH comprising the amino acid sequence of SEQ ID NO:15, wherein the antibody is linked to a amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. The amino acid sequences of SEQ ID NO:15 and SEQ ID NO:16 are provided below.

m11-1F4 VH

SEQ ID NO: 15
QVQLKESGPGLVAPSQSLSITCTVSGFSLSSYGVSWVRQPPGKGLEWLG

VIWGDGSTNYHPNLMSRLSISKDISKSQVLFKLNSLQTDDTATYYCVTL
DYWGQGTSVTVSS m11-1F4 VL

SEQ ID NO: 16
DVVMTQTPLSLPVSLGDQASISCRSSQSLVHRNGNTYLHWYLQKPGQSP

KLLIYKVSNRESGVPDRESGSGSGTDFTLKISRVEAEDLGLYFCFQTTY

VPNTFGGGTKLEIK

In another aspect, the antibody-peptide fusion protein comprises an antibody, wherein the antibody comprises a VH comprising a CDR-H1 comprising the amino acid sequence of SEQ ID NO: 17, a CDR-H2 comprising the amino acid sequence of SEQ ID NO: 18, and a CDR-H3 comprising the amino acid sequence of SEQ ID NO:19; and a VL comprising a CDR-L1 comprising the amino acid sequence of SEQ ID NO:20, a CDR-L2 comprising the amino acid sequence of SEQ ID NO:21, and a CDR-L3 comprising the amino acid sequence of SEQ ID NO:22, and wherein the antibody is linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the antibody-peptide fusion protein comprises an antibody linked to an amyloid-reactive peptide comprising any of the amino acid sequences listed in Table 1. In some embodiments, the antibody-peptide fusion protein comprises an antibody linked to an amyloid-reactive peptide comprising the amino acid sequence of SEQ ID NO: 1. In some embodiments, the antibody-peptide fusion protein comprises an antibody linked to an amyloid-reactive peptide comprising the amino acid sequence of SEQ ID NO:2. In some embodiments, the antibody-peptide fusion protein comprises an antibody linked to an amyloid-reactive peptide comprising the amino acid sequence of any one or SEQ ID NOs: 1-13.

In another aspect, the antibody-peptide fusion protein comprises an antibody, wherein the antibody comprises a VH CDR1, a VH CDR2, and a VH CDR3 of a VH having the sequence set forth in SEQ ID NO:15 and a VL CDR1, a VL CDR2, and a VL of a VL having the sequence set forth in SEQ ID NO:16; and wherein the antibody is linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the antibody-peptide fusion protein comprises an antibody linked to an amyloid-reactive peptide comprising any of the amino acid sequences listed in Table 1. In some embodiments, the antibody-peptide fusion protein comprises an antibody linked to an amyloid-reactive peptide comprising the amino acid sequence of SEQ ID NO:1. In some embodiments, the antibody-peptide fusion protein comprises an antibody linked to an amyloid-reactive peptide comprising the amino acid sequence of SEQ ID NO:2. In some embodiments, the antibody-peptide fusion protein comprises an antibody linked to an amyloid-reactive peptide comprising the amino acid sequence of any of SEQ ID NOs: 1-13.

In some embodiments, the antibody-peptide fusion protein comprises an antibody that comprises a heavy chain comprising a VH comprising the amino acid sequence of SEQ ID NO:15 and a light chain comprising a VL comprising the amino acid sequence of SEQ ID NO: 16, wherein the light chain is linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the antibody-peptide fusion protein comprises a heavy chain comprising a VH comprising the amino acid sequence of SEQ ID NO: 15 without the C-terminal lysine residue, and a VL comprising the amino acid sequence of SEQ ID NO:16, wherein the antibody is linked to an amyloid-reactive peptide.

In another aspect, the antibody-peptide fusion protein comprises an antibody linked to an amyloid-reactive peptide. In some embodiments, the antibody-peptide fusion protein comprises an antibody linked to an amyloid-reactive peptide comprising any of the amino acid sequences listed in Table 1. In some embodiments, the antibody-peptide fusion protein comprises an antibody linked to an amyloid-reactive peptide comprising the amino acid sequence of SEQ ID NO:1. In some embodiments, the antibody-peptide fusion protein comprises an antibody linked to an amyloid-reactive peptide comprising the amino acid sequence of SEQ ID NO:2. In some embodiments, the antibody-peptide fusion protein comprises an antibody linked to an amyloid-reactive peptide comprising the amino acid sequence of any of SEQ ID NOs: 1-13. In some embodiments, the amyloid-reactive peptide is linked to the N-terminus or C-terminus of the antibody light chain or the N- or C-terminus of the heavy chain. In some embodiments, the antibody also comprises a spacer amino acid sequence between the amyloid-reactive peptide and the N-terminus or C-terminus of the antibody light chain or the N- or C-terminus of the heavy chain. In some embodiments, the spacer is a peptide spacer. In some embodiments, the spacer is flexible or rigid. In some embodiments, the spacer comprises the amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the spacer comprises an amino acid sequence selected from the group consisting of SEQ ID NO:83 and SEQ ID NO:86. In some embodiments, the spacer comprises an amino acid sequence set forth in SEQ ID NO:83. In some embodiments, the amyloid-reactive peptide is linked to the C-terminus of the light chain. In some embodiments, the amyloid-reactive peptide set forth in SEQ ID NO:2 is linked to the C-terminus of the light chain via the spacer comprising an amino acid sequence set forth in SEQ ID NO:83.

In some embodiments, the antibody-peptide fusion protein comprises an antibody that comprises a heavy chain comprising a VH comprising the amino acid sequence of SEQ ID NO:15, wherein the heavy chain is linked to a amyloid-reactive peptide comprising any of the amino acid sequences of Table 1. In some embodiments, the antibody-peptide fusion protein comprise an antibody comprising a heavy chain comprising a VH comprising the amino acid sequence of SEQ ID NO: 15, wherein the heavy chain is linked to a amyloid-reactive peptide comprising the amino acid sequence of SEQ ID NO: 1. In some embodiments, the antibody-peptide fusion protein comprises an antibody comprising a heavy chain comprising a VH comprising the amino acid sequence of SEQ ID NO:15, wherein the heavy chain is linked to a amyloid-reactive peptide comprising the amino acid sequence of SEQ ID NO:2. In some embodiments, the antibody-peptide fusion protein comprises an antibody comprising a heavy chain comprising a VH comprising the amino acid sequence of SEQ ID NO: 15, wherein the heavy chain is linked to a amyloid-reactive peptide comprising the amino acid sequence of any of SEQ ID NOs: 1-13. In some embodiments, the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, the antibody-peptide fusion protein comprises an antibody that comprises a light chain comprising a VL comprising the amino acid sequence of SEQ ID NO:16, wherein the light chain is linked to a amyloid-reactive peptide comprising any of the amino acid sequences of Table 1. In some embodiments, the antibody-peptide fusion protein comprises an antibody comprising a light chain comprising a VL comprising the amino acid sequence of SEQ ID NO: 16, wherein the light chain is linked to a amyloid-reactive peptide comprising the amino acid sequence of SEQ ID NO:1. In some embodiments, the antibody-peptide fusion protein comprises an antibody a light chain comprising a VL comprising the amino acid sequence of SEQ ID NO:16, wherein the light chain is linked to a amyloid-reactive peptide comprising the amino acid sequence of SEQ ID NO:2. In some embodiments, the antibody-peptide fusion protein comprises an antibody a light chain comprising a VL comprising the amino acid sequence of SEQ ID NO: 16, wherein the light chain is linked to a amyloid-reactive peptide comprising the amino acid sequence of any of SEQ ID NOs: 1-13. In some embodiments, the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, the antibody-peptide fusion protein comprises an antibody comprising a heavy chain comprising a VH comprising the amino acid sequence of SEQ ID NO: 15 and a light chain comprising a VL comprising the amino acid sequence of SEQ ID NO: 16, wherein the light chain is linked to a amyloid-reactive peptide comprising any of the amino acid sequences of Table 1. In some embodiments, the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, the antibody-peptide fusion protein comprises an antibody comprising heavy chain comprising a VH comprising the amino acid sequence of SEQ ID NO: 15 and a light chain comprising a VL comprising the amino acid sequence of SEQ ID NO: 16, wherein the light chain is linked to an amyloid-reactive peptide comprising the amino acid sequence of SEQ ID NO:1. In some embodiments, the amyloid-reactive peptide is linked to the light chain at the N-terminus. In some embodiments, the amyloid-reactive peptide is linked to the light chain at the C-terminus. In some embodiments, the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, the antibody-peptide fusion protein comprises an antibody a heavy chain comprising a VH comprising the amino acid sequence of SEQ ID NO:15 and a light chain comprising a VL comprising the amino acid sequence of SEQ ID NO:16, wherein the light chain is linked to an amyloid-reactive peptide comprising the amino acid sequence of SEQ ID NO:2. In some embodiments, the amyloid-reactive peptide is linked to the light chain at the N-terminus. In some embodiments, the amyloid-reactive peptide is linked to the light chain at the C-terminus. In some embodiments, the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, the antibody-peptide fusion protein comprises an antibody a heavy chain comprising a VH comprising the amino acid sequence of SEQ ID NO:15 and a light chain comprising a VL comprising the amino acid sequence of SEQ ID NO:16, wherein the light chain is linked to an amyloid-reactive peptide comprising the amino acid sequence of any of SEQ ID NOs: 1-13. In some embodiments, the amyloid-reactive peptide is linked to the light chain at the N-terminus. In some embodiments, the amyloid-reactive peptide is linked to the light chain at the C-terminus. In some embodiments, the amyloid-reactive peptide is linked to the antibody via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

Also provided herein are antibody-peptide fusion proteins comprising a humanized antibody that binds to human amyloid fibrils fused to an amyloid-reactive peptide. In some embodiments, the antibody-peptide fusion protein comprises a humanized antibody as described herein. In some embodiments, the humanized antibody comprises a humanized VH and/or VL sequence derived from m11-1F4. In some embodiments, the antibody-peptide fusion protein comprises a humanized antibody as described in International Application No. PCT/US2020/060596, which is hereby incorporated by reference in its entirety. Exemplary amino acid sequences of humanized VH and VL regions are provided below in Tables 3-4. In Tables 3-4, CDR sequences are underlined, and back mutated residues and further mutations that were introduced into the humanized variants VL4 and VH9 are bolded, and italicized. Further mutations that were introduced into VL4 and VH9 are listed in the IgG column of Tables 3-4; these mutations are numbered relative to the N-terminus of the VL or VH. CDR amino acid sequences for variants of VL4 and VH9 with modified CDRs are presented in Table 5 and Table 6, as compared to VL4 and VH9, below.

TABLE 3

Amino acid sequences of humanized light chain variable region sequences

| IgG | VL Amino Acid Sequence | SEQ ID NO |
|---|---|---|
| VL1 | DVVMTQSPLSLPVTLGQPASISCRSSQSLVHRNGNTYLHWFQQRPGQSPRRLIYKVSNRFSGVPDRESGSGSGTDFTLKISRVEAEDVGVYYCFQTTYVPNTFGGGTKLEIK | 32 |
| VL2 | DVVMTQSPLSLPVTLGQPASISCRSSQSLVHRNGNTYLHW*YL*QRPGQSPRRLIYKVSNRFSGVPDRESGSGSGTDFTLKISRVEAEDVGVYYCFQTTYVPNTFGGGTKLEIK | 33 |
| VL3 | DVVMTQSPLSLPVTLGQPASISCRSSQSLVHRNGNTYLHW*YL*QRPGQSPR*L*LIYKVSNRFSGVPDRESGSGSGTDFTLKISRVEAEDVG*LYF*CFQTTYVPNTFGGGTKLEIK | 34 |
| VL4 | DVVMTQSPLSLPVTLGQPASISCRSSQSLVHRNGNTYLHWFQQRPGQSPR*L*LIYKVSNRFSGVPDRESGSGSGTDFTLKISRVEAEDVGVYF*C*FQTTYVPNTFGGGTKLEIK | 35 |
| VL4-N33S | DVVMTQSPLSLPVTLGQPASISCRSSQSLVHRSGNTYLHWFQQRPGQSPR*L*LIYKVSNRFSGVPDRFSGSGSGTDFTLKISRVEAEDVGVYFCFQTTYVPNTFGGGTKLEIK | 36 |
| VL4-N33Q | DVVMTQSPLSLPVTLGQPASISCRSSQSLVHRQGNTYLHWFQQRPGQSPR*L*LIYKVSNRFSGVPDRESGSGSGTDFTLKISRVEAEDVGVYFCFQTTYVPNTFGGGTKLEIK | 37 |
| VL4-N33E | DVVMTQSPLSLPVTLGQPASISCRSSQSLVHREGNTYLHWFQQRPGQSPR*L*LIYKVSNRFSGVPDRESGSGSGTDFTLKISRVEAEDVGVYFCFQTTYVPNTFGGGTKLEIK | 38 |
| VL4-N33A | DVVMTQSPLSLPVTLGQPASISCRSSQSLVHRAGNTYLHWFQQRPGQSPR*L*LIYKVSNRFSGVPDRESGSGSGTDFTLKISRVEAEDVGVYFCFQTTYVPNTFGGGTKLEIK | 39 |
| VL4-N33H | DVVMTQSPLSLPVTLGQPASISCRSSQSLVHRHGNTYLHWFQQRPGQSPR*L*LIYKVSNRFSGVPDRESGSGSGTDFTLKISRVEAEDVGVYFCFQTTYVPNTFGGGTKLEIK | 40 |

TABLE 3-continued

Amino acid sequences of humanized light chain variable region sequences

| IgG | VL Amino Acid Sequence | SEQ ID NO |
|---|---|---|
| VL4-G34A | DVVMTQSPLSLPVTLGQPASISCRSSQSLVHRAGNTYLHWFQQRPGQSPR*L*LIYKVSNRFSGVPDRESGSGSGTDFTLKISRVEAEDVGVYFCFQTTYVPNTFGGGTKLEIK | 41 |
| VL4-G34V | DVVMTQSPLSLPVTLGQPASISCRSSQSLVHRVGNTYLHWFQQRPGQSPR*L*LIYKVSNRFSGVPDRESGSGSGTDFTLKISRVEAEDVGVYFCFQTTYVPNTFGGGTKLEIK | 42 |

TABLE 4

Amino acid sequences of humanized heavy chain variable region sequences

| IgG | VH Amino Acid Sequence | SEQ ID NO |
|---|---|---|
| VH1 | QVQLQESGPGLVKPSETLSLTCTVSGFSLSSYGVSWIRQPPGKGLEWIGVIWGDGSTNYHPNLMSRVTISVDTSKNQFSLKLSSVTAADTAVYYCARLDYWGQGTSVTVSS | 43 |
| VH2 | QVQLQESGPGLVKPSETLSLTCTVSGFSLSSYGVSWVRQPPGKGLEW*L*GVIWGDGSTNYHPNLMSRVTISVDTSKNQFSLKLSSVTAADTAVYYCARLDYWGQGTSVTVSS | 44 |
| VH3 | QVQLQESGPGLVKPSETLSLTCTVSGFSLSSYGVSWIRQPPGKGLEWIGVIWGDGSTNYHPNLMSR*LS*ISVDTSKNQFSLKLSSVTAADT*A*YYC*VT*LDYWGQGTSVTVSS | 45 |
| VH4 | QVQLQESGPGLVKPSETLSLTCTVSGFSLSSYGVSWVRQPPGKGLEW*L*GVIWGDGSTNYHPNLMSR*LS*ISVDTSKNQFSLKLSSVTAADTAVYYCARLDYWGQGTSVTVSS | 46 |
| VH5 | QVQLQESGPGLVKPSETLSLTCTVSGFSLSSYGVSWVRQPPGKGLEW*L*GVIWGDGSTNYHPNLMSR*LS*ISVDTSKNQFSLKLSSVTAADTAVYYC*VT*LDYWGQGTSVTVSS | 47 |
| VH6 | QVQLQESGPGLVKPSETLSLTCTVSGFSLSSYGVSWVRQPPGKGLEW*L*GVIWGDGSTNYHPNLMSR*LS*IS*K*DTSKNQFSLKLSSVTAADT*A*YYC*VT*LDYWGQGTSVTVSS | 48 |
| VH7 | QVQLQESGPGLVKPSETLSLTCTVSGFSLSSYGVSWIRQPPGKGLEWIGVIWGDGSTNYHPNLMSRVTIS*K*DTSKNQ*VL*LKLSSVTAADTAVYYC*VT*LDYWGQGTSVTVSS | 49 |
| VH8 | QVQLQESGPGLVKPSETLSLTCTVSGFSLSSYGVSWIRQPPGKGLEWIGVIWGDGSTNYHPNLMSRVTIS*K*DTSK*S*QFSLKLSSVTAADTAVYYC*VT*LDYWGQGTSVTVSS | 50 |
| VH9 | QVQLQESGPGLVKPSETLSLTCTVSGFSLSSYGVSWIRQPPGKGLEW*L*GVIWGDGSTNYHPNLMSRVTISVDTSK*SQ**VLF*KLSSVTAADTAVYYC*A*TLDYWGQGTSVTVSS | 51 |
| VH10 | QVQLQESGPGLVKPSETLSLTCTVSGFSLSSYGVSWIRQPPGKGLEW*L*GVIWGDGSTNYHPNLMSR*LS*IS*K*DTSK*SQ**VL*LKLSSVTAADTAVYYC*VT*LDYWGQGTSVTVSS | 52 |
| VH9-D54S | QVQLQESGPGLVKPSETLSLTCTVSGFSLSSYGVSWIRQPPGKGLEW*L*GVIWGSGSTNYHPNLMSRVTISVDTSK*SQ**VLF*KLSSVTAADTAVYYC*A*TLDYWGQGTSVTVSS | 53 |
| VH9-D54Q | QVQLQESGPGLVKPSETLSLTCTVSGFSLSSYGVSWIRQPPGKGLEW*L*GVIWGQGSTNYHPNLMSRVTISVDTSK*SQ**VLF*KLSSVTAADTAVYYC*A*TLDYWGQGTSVTVSS | 54 |
| VH9-D54E | QVQLQESGPGLVKPSETLSLTCTVSGFSLSSYGVSWIRQPPGKGLEW*L*GVIWGEGSTNYHPNLMSRVTISVDTSK*SQ**VLF*KLSSVTAADTAVYYC*A*TLDYWGQGTSVTVSS | 55 |
| VH9-D54A | QVQLQESGPGLVKPSETLSLTCTVSGFSLSSYGVSWIRQPPGKGLEW*L*GVIWGAGSTNYHPNLMSRVTISVDTSK*SQ**VLF*KLSSVTAADTAVYYC*A*TLDYWGQGTSVTVSS | 56 |

TABLE 4-continued

Amino acid sequences of humanized heavy chain variable region sequences

| IgG | VH Amino Acid Sequence | SEQ ID NO |
|---|---|---|
| VH9-D54H | QVQLQESGPGLVKPSETLSLTCTVSGFSLSSYGVSWIRQPPGKGLEW*L*GVIWGHGSTNYHPNLMSRVTISVDTSK*SQYLF*KLSSVTAADTAVYYCA*T*LDYWGQGTSVTVSS | 57 |
| VH9-G55A | QVQLQESGPGLVKPSETLSLTCTVSGFSLSSYGVSWIRQPPGKGLEW*L*GVIWGDASTNYHPNLMSRVTISVDTSK*SQYLF*KLSSVTAADTAVYYCA*T*LDYWGQGTSVTVSS | 58 |
| VH9-G55V | QVQLQESGPGLVKPSETLSLTCTVSGFSLSSYGVSWIRQPPGKGLEW*L*GVIWGDVSTNYHPNLMSRVTISVDTSK*SQYLF*KLSSVTAADTAVYYCA*T*LDYWGQGTSVTVSS | 59 |
| VH9-M64V | QVQLQESGPGLVKPSETLSLTCTVSGFSLSSYGVSWIRQPPGKGLEW*L*GVIWGDGSTNYHPNLVSRVTISVDTSK*SQYLF*KLSSVTAADTAVYYCA*T*LDYWGQGTSVTVSS | 60 |
| VH9-M64I | QVQLQESGPGLVKPSETLSLTCTVSGFSLSSYGVSWIRQPPGKGLEW*L*GVIWGDGSTNYHPNLISRVTISVDTSK*SQYLF*KLSSVTAADTAVYYCA*T*LDYWGQGTSVTVSS | 61 |
| VH9-M64L | QVQLQESGPGLVKPSETLSLTCTVSGFSLSSYGVSWIRQPPGKGLEW*L*GVIWGDGSTNYHPNLLSRVTISVDTSK*SQYLF*KLSSVTAADTAVYYCA*T*LDYWGQGTSVTVSS | 62 |
| VH9-M64A | QVQLQESGPGLVKPSETLSLTCTVSGFSLSSYGVSWIRQPPGKGLEW*L*GVIWGDGSTNYHPNLASRVTISVDTSK*SQYLF*KLSSVTAADTAVYYCA*T*LDYWGQGTSVTVSS | 63 |

TABLE 5

Amino acid sequences of VL4 CDRs

| | CDR-L1 | | CDR-L2 | | CDR-L3 | |
|---|---|---|---|---|---|---|
| IgG | Amino Acid Sequence | SEQ ID NO | Amino Acid Sequence | SEQ ID NO | Amino Acid Sequence | SEQ ID NO |
| VL4 | RSSQSLVHRNGNTYLH | 20 | KVSNRES | 21 | FQTTYVPNT | 22 |
| VL4-N33S | RSSQSLVHRSGNTYLH | 64 | KVSNRES | 21 | FQTTYVPNT | 22 |
| VL4-N33Q | RSSQSLVHRQGNTYLH | 65 | KVSNRES | 21 | FQTTYVPNT | 22 |
| VL4-N33E | RSSQSLVHREGNTYLH | 66 | KVSNRES | 21 | FQTTYVPNT | 22 |
| VL4-N33A | RSSQSLVHRAGNTYLH | 67 | KVSNRES | 21 | FQTTYVPNT | 22 |
| VL4-N33H | RSSQSLVHRHGNTYLH | 68 | KVSNRES | 21 | FQTTYVPNT | 22 |
| VL4-G34A | RSSQSLVHRNANTYLH | 69 | KVSNRES | 21 | FQTTYVPNT | 22 |
| VL4-G34V | RSSQSLVHRNVNTYLH | 70 | KVSNRES | 21 | FQTTYVPNT | 22 |

TABLE 6

Amino acid sequences of VH9 CDRs

| IgG | CDR-H1 Amino Acid Sequence | SEQ ID NO | CDR-H2 Amino Acid Sequence | SEQ ID NO | CDR-H3 Amino Acid Sequence | SEQ ID NO |
|---|---|---|---|---|---|---|
| VH9 | GFSLSSYGVS | 17 | VIWGDGSTNYHPNLMS | 18 | LDY | 19 |
| VH9-D54S | GFSLSSYGVS | 17 | VIWGSGSTNYHPNLMS | 71 | LDY | 19 |
| VH9-D54Q | GFSLSSYGVS | 17 | VIWGQGSTNYHPNLMS | 72 | LDY | 19 |
| VH9-D54E | GESLSSYGVS | 17 | VIWGEGSTNYHPNLMS | 73 | LDY | 19 |
| VH9-D54A | GFSLSSYGVS | 17 | VIWGAGSTNYHPNLMS | 74 | LDY | 19 |
| VH9-D54H | GFSLSSYGVS | 17 | VIWGHGSTNYHPNLMS | 75 | LDY | 19 |
| VH9-G55A | GFSLSSYGVS | 17 | VIWGDASTNYHPNLMS | 76 | LDY | 19 |
| VH9-G55V | GFSLSSYGVS | 17 | VIWGDVSTNYHPNLMS | 77 | LDY | 19 |
| VH9-M64V | GFSLSSYGVS | 17 | VIWGDGSTNYHPNLVS | 78 | LDY | 19 |
| VH9-M64I | GFSLSSYGVS | 17 | VIWGDGSTNYHPNLIS | 79 | LDY | 19 |
| VH9-M64L | GFSLSSYGVS | 17 | VIWGDGSTNYHPNLLS | 80 | LDY | 19 |
| VH9-M64A | GFSLSSYGVS | 17 | VIWGDGSTNYHPNLAS | 81 | LDY | 19 |

In some embodiments, the antibody-peptide fusion protein comprises a humanized antibody comprising a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO: 18, and a CDR-H3 comprising the amino acid sequence set forth in SEQ ID NO: 19. In some embodiments, the humanized antibody comprises one, two, three, four, five, or six CDRs of an antibody as shown in Table 2. In some embodiments, the humanized antibody comprises a CDR-H1, a CDR-H2, and a CDR-H3, respectively comprising the amino acid sequences of a CDR-H1, a CDR-H2, and a CDR-H3 of a VH having the sequence set forth in SEQ ID NO:15; and a CDR-L1, a CDR-L2, and a CDR-L3, respectively comprising the amino acid sequences of a CDR-L1, a CDR-L2, and a CDR-L3 of a VL having the sequence set forth in SEQ ID NO:16. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, the antibody-peptide fusion protein comprises a humanized antibody comprising a light chain variable region (VL) and a heavy chain variable region (VH), wherein the VL comprises a CDR-L1 comprising the amino acid sequence set forth in SEQ ID NO:20 with one or more conservative amino acid substitutions, a CDR-L2 comprising the amino acid sequence set forth in SEQ ID NO:21 with one or more conservative amino acid substitutions, and a CDR-L3 comprising the amino acid sequence set forth in SEQ ID NO:22 with one or more conservative amino acid substitutions, and the VH comprises a CDR-H1 comprising the amino acid sequence set forth in SEQ ID NO: 17 with one or more conservative amino acid substitutions, a CDR-H2 comprising the amino acid sequence set forth in SEQ ID NO:18 with one or more conservative amino acid substitutions, and a CDR-H3 comprising the amino acid sequence set forth in SEQ ID NO:19 with one or more conservative amino acid substitutions. In some embodiments, the humanized antibody comprises one, two, three, four, five, or six CDRs of an antibody as shown in Table 2, with one or more conservative amino acid substitutions. In some embodiments, the humanized antibody comprises a CDR-H1, a CDR-H2, and a CDR-H3, respectively comprising the amino acid sequences of a CDR-H1, a CDR-H2, and a CDR-H3 of a VH having the sequence set forth in SEQ ID NO: 15 with one or more conservative amino acid substitutions; and a CDR-L1, a CDR-L2, and a CDR-L3, respectively comprising the amino acid sequences of a CDR-L1, a CDR-L2, and a CDR-L3 of a VL having the sequence set forth in SEQ ID NO:16 with one or more conservative amino acid substitutions. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NOs:64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO:18, and a CDR-H3 comprising the amino acid sequence set forth in SEQ ID NO: 19. In some embodiments, the antibody-peptide fusion protein comprises a humanized antibody, wherein the humanized antibody comprises a VL comprising a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NOs: 71-81; and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:71, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:72, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of in SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO:74, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:75, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO:76, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:77, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:78, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:79, and a CDR-H3 comprising the amino acid sequence set forth in SEQ ID NO: 19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:80, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence selected from the group consisting of SEQ ID NOs: 64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence set forth in SEQ ID NO:81, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO: 17, a CDR-H2 comprising the amino acid sequence selected from the group consisting of SEQ ID NOs: 71-81, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NO:65, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence selected from the group consisting of SEQ ID NOs: 71-81, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NO:66, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence selected from the group consisting of SEQ ID NOs: 71-81, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NO:67, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence selected from the group consisting of SEQ ID NOs: 71-81, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NO:68, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence selected from the group consisting of SEQ ID NOs: 71-81, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NO:69, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence selected from the group consisting of SEQ ID NOs: 71-81, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NO:70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence selected from the group consisting of SEQ ID NOs: 71-81, and a CDR-H3 comprising the amino acid sequence set forth in SEQ ID NO:19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In some embodiments, antibody-peptide fusion protein comprises a humanized antibody comprising a VL comprising a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO:73, and a CDR-H3 comprising the amino acid sequence set forth in SEQ ID NO: 19. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide is linked to the antibody via a spacer comprising an amino acid sequence selected from the group consisting of SEQ ID NO:83 and SEQ ID NO:86. In some embodiments, the amyloid-reactive peptide is linked to the antibody via a spacer comprising an amino acid sequence set forth in SEQ ID NO:83. In some embodiments, the amyloid-reactive peptide comprises the amino acid sequence set forth in SEQ ID NO:1 or SEQ ID NO:2. In some embodiments, the amyloid-reactive peptide comprises the amino acid sequence set forth in SEQ ID NO:2. In some embodiments, the antibody-peptide fusion protein comprises an antibody linked to an amyloid-reactive peptide set forth in SEQ ID NO:2 via a spacer comprising an amino acid sequence set forth in SEQ ID NO:83. In some embodiments, the antibody-peptide fusion protein is a full length antibody. In some embodiments, the antibody-peptide fusion protein has an IgG1 isotype. In some embodiments, the antibody peptide fusion protein comprises a light chain comprising from N- to C-terminus in order a VL, a CL, a spacer, and an amyloid reactive peptide. In some embodiments, the amyloid-reactive peptide is fused to the C-terminus of the light chain via a spacer.

In some embodiments, the antibody-peptide fusion protein comprises a humanized antibody comprising the amino acid sequence of a VL as shown in Table 3. In some embodiments, the antibody-peptide fusion protein comprises a humanized antibody, wherein the humanized antibody comprises a VL selected from the group consisting of VL2, VL3, VL4, VL4-N33S, VL4-N33Q, VL4-N33E, VL4-N33A, VL4-N33H, VL4-G34A, or VL4-G34V, as shown in Table 3. In some embodiments, the VL comprises an amino acid sequence set forth in the group consisting of SEQ ID NOs: 32-42. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising the amino acid sequence of a VH as shown in Table 4. In some embodiments, the antibody-peptide fusion protein comprises a humanized antibody, wherein the humanized antibody comprises a VH selected from the group consisting of VH2, VH3, VH4, VH5, VH6, VH7, VH8, VH9, VH10, VH9-D54S, VH9-D54Q, VH9-D54E, VH9-D54A, VH9-D54H, VH9-G55A, VH9-G55V, VH9-M64V, VH9-M64I, VH9-M64L, or VH9-M64A, as shown in Table 4. In some embodiments, the VH comprises an amino acid sequence set forth in the group consisting of SEQ ID NOs: 43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:32, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:33, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:34, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:35, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:36, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:37, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:38, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:39, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:40, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:41, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:42, and a VH comprising an amino acid sequence selected from the group consisting of SEQ ID NOs:43-63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:43. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:44. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:45. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:46. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:47. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:48. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:49. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:50. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:51. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:52. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:53. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:54. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:55. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:56. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VII comprising an amino acid sequence set forth in SEQ ID NO:57. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:58. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VII comprising an amino acid sequence set forth in SEQ ID NO:59. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:60. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:61. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:62. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence selected from the group consisting of SEQ ID NOs:32-42, and a VH comprising an amino acid sequence set forth in SEQ ID NO:63. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:34, and a VH comprising an amino acid sequence set forth in SEQ ID NO:48. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:51. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:52. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:50. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:49. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising a VL comprising an amino acid sequence set forth in SEQ ID NO:36, and a VH comprising an amino acid sequence set forth in SEQ ID NO:55. In some embodiments, the antibody-peptide fusion protein comprises an antibody linked to an amyloid-reactive peptide via a spacer. In some embodiments, the amyloid-reactive peptide is fused to the C-terminus of the light chain via a spacer. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide is linked to the antibody via a spacer comprising an amino acid sequence selected from the group consisting of SEQ ID NO:83 and SEQ ID NO:86. In some embodiments, the amyloid-reactive peptide is linked to the antibody via a spacer comprising an amino acid sequence set forth in SEQ ID NO:83. In some embodiments, the amyloid-reactive peptide comprises the amino acid sequence selected from the group consisting of SEQ ID NOs: 1-13. In some embodiments, the amyloid-reactive peptide comprises the amino acid sequence set forth in SEQ ID NO:1 or SEQ ID NO:2. In some embodiments, the amyloid-reactive peptide comprises the amino acid sequence set forth in SEQ ID NO:2. In some embodiments, the antibody-peptide fusion protein comprises an antibody linked to an amyloid-reactive peptide set forth in SEQ ID NO:2 via a spacer comprising an amino acid sequence set forth in SEQ ID NO:83.

In some embodiments, the antibody-peptide fusion protein comprises a humanized antibody comprising the VL of VL4 as shown in Table 3, and the VH of VH9 as shown in Table 4. In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:51. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising the VL of VL4-N33S as shown in Table 3, and the VH of VH9-D54E as shown in Table 4. In some embodiments, the antibody-peptide fusion protein comprises a humanized antibody comprising a VL comprising an amino acid sequence set forth in SEQ ID NO:36, and a VH comprising an amino acid sequence set forth in SEQ ID NO:55. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising the VL of VL3 as shown in Table 3, and the VH of VH6 as shown in Table 4. In some embodiments, the antibody-peptide fusion protein comprises a humanized antibody comprising a VL comprising an amino acid sequence set forth in SEQ ID NO:34, and a VH comprising an amino acid sequence set forth in SEQ ID NO:48. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprises a humanized antibody comprising the VL of VL4 as shown in Table 3, and the VH of VH10 as shown in Table 4. In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:52. In some embodiments, the antibody-peptide fusion protein comprises a humanized antibody comprising the VL of VL4 as shown in Table 3, and the VH of VH8 as shown in Table 4. In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:50. In some embodiments, the antibody-peptide fusion protein comprises a humanized antibody comprising the VL of VL4 as shown in Table 3, and the VH of VH7 as shown in Table 4. In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:69. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13.

In some embodiments, the antibody-peptide fusion protein comprising a humanized antibody comprises an amyloid-reactive peptide. In some embodiments, the amyloid-reactive peptide comprises one or more of the peptides shown in Table 1. In certain some embodiments, the amyloid-reactive peptide comprises an amino acid sequence selected from the group consisting of SEQ ID NOs: 1-13. In some embodiments, the amyloid-reactive peptide comprises the amino acid sequence set forth in SEQ ID NO:1. In some embodiments, the amyloid-reactive peptide comprises the amino acid sequence set forth in SEQ ID NO:2.

In some embodiments, the antibody-peptide fusion protein comprises a humanized antibody, wherein the humanized antibody comprises a light chain. In some embodiments, the amyloid-reactive peptide is fused to the N-terminus of the light chain. In some embodiments, the amyloid-reactive peptide is fused to the C-terminus of the light chain. In some embodiments, the antibody-peptide fusion protein comprises a humanized antibody, wherein the humanized antibody comprises a light chain, wherein the amyloid-reactive peptide is fused to the N-terminus of the light chain by a spacer. In some embodiments, the antibody-peptide fusion protein comprises a humanized antibody, wherein the humanized antibody comprises a light chain, wherein the amyloid-reactive peptide is fused to the C-terminus of the light chain by a spacer. In some embodiments, the spacer is a peptide spacer. In some embodiments, the spacer is a flexible spacer. In some embodiments, the space comprises glycine and serine residues. In some embodiments, the spacer comprises the amino acid sequence GGGYS. In some embodiments, the spacer comprises the amino acid sequence set forth in SEQ ID NO:27. In some embodiments, the spacer is a rigid spacer. In some embodiments, the spacer is uncharged. In some embodiments, the spacer comprises an amino acid sequence set forth in SEQ ID NOs: 83-86.

In some embodiments, the antibody-peptide fusion protein comprises a humanized antibody, wherein the humanized antibody comprises a light chain. In some embodiments, the amyloid-reactive peptide is fused to the N-terminus of the heavy chain. In some embodiments, the amyloid-reactive peptide is fused to the C-terminus of the heavy chain. In some embodiments, the antibody-peptide fusion protein comprises a humanized antibody, wherein the humanized antibody comprises a heavy chain, wherein the amyloid-reactive peptide is fused to the N-terminus of the heavy chain by a spacer. In some embodiments, the antibody-peptide fusion protein comprises a humanized antibody, wherein the humanized antibody comprises a heavy chain, wherein the amyloid-reactive peptide is fused to the C-terminus of the heavy chain by a spacer. In some embodiments, the spacer is a peptide spacer. In some embodiments, the spacer is a flexible spacer. In some embodiments, the spacer is a rigid spacer. In some embodiments, the spacer is uncharged. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86.

In certain embodiments, the antibody-peptide fusion protein may include spacer sequences of amino acids between the C- or N-terminus of the light chain or C- or N-terminus of the heavy and the amyloid-reactive peptide. In certain embodiments, the peptide-Ig conjugates may include spacer sequences of amino acids between the N-terminal of the peptide and a leader sequence required for secretion of the Ig-peptide from cells expressing the reagent. In some embodiments, the spacer is a flexible spacer. In some embodiments, the spacer is a rigid spacer peptide. In some embodiments, the spacer is uncharged. In some embodiments a spacer peptide may comprise or consist of from about 3 to about 55 amino acids. The spacer peptides of the present invention may comprise or consist of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. As used herein, a nucleic acid sequence or amino acid sequence is "adjacent" to another nucleic acid sequence or amino acid sequence if such nucleic acid sequences or amino acid sequences are close to each other in sequence. For example, two nucleic acid sequences can be adjacent to each other as described herein but still include an intervening spacer sequence. In some embodiments, the spacer peptide comprises an amino acid sequence as set forth in Table 9, below. In some embodiments, the spacer comprises an amino acid sequence set forth in SEQ ID NOs: 83-86.

TABLE 7

Exemplary Spacer Sequences

| Description | Amino Acid Sequence | SEQ ID NO |
|---|---|---|
| Short, rigid spacer | VSPSV | SEQ ID NO: 83 |
| Long, rigid spacer | VSPSVVSPSV | SEQ ID NO: 84 |
| Flexible, short spacer | GGSGG | SEQ ID NO: 85 |
| Flexible, long spacer | GGGGSGGGGS | SEQ ID NO: 86 |

In some embodiments, one or more of the peptides shown in Table 1 can be linked to a humanized antibody or functional fragment thereof through the C- or N-terminus of the light chain protein or the C- or N-terminus of the heavy chain, thereby forming an antibody-peptide fusion protein comprising a humanized antibody. That is, any of the sequences identified below in Table 1 can be linked to the heavy or light chain of the humanized antibody or functional fragment thereof independently or simultaneously to form an antibody-peptide fusion protein. For example, two of the amyloid-reactive peptides can be linked with a single antibody, such by linking the amyloid-reactive peptide amino acid sequences to the N-terminus of a humanized antibody light chain, or joining the amyloid-reactive peptide amino acid sequences to the C-terminus of a humanized antibody light chain.

In some embodiments, the antibody-peptide fusion protein comprises a light chain further comprising a light chain constant region (e.g., comprising a CL1), and a heavy chain comprising a heavy chain constant region (e.g., comprising a CH1, a CH2, and a CH3). In some embodiments, the antibody-peptide fusion protein comprises two light chains and two heavy chains.

In some embodiments, the antibody-peptide fusion protein comprises a light chain comprising, from N- to C-terminus, an amyloid-reactive peptide and a light chain. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3. In some embodiments, the VH is any one of the VHs described herein. In some embodiments, the antibody-peptide fusion protein comprises a first and second light chain comprising, from N-terminal to C-terminal direction an amyloid reactive peptide, a spacer, a variable light chain region, and a constant light chain region, and a first and second heavy chain comprising, from N- to C-terminus, a VH, a CH1, a CH2, and a CH3, wherein the CH2 and the CH3 of the first and second heavy chain form a dimer.

In some embodiments, the antibody-peptide fusion protein comprises a light chain comprising, from N- to C-terminus, a light chain and an amyloid-reactive peptide. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3. In some embodiments, the VH is any one of the VHs described herein. In some embodiments, the antibody-peptide fusion protein comprises a first and second light chain comprising, from the N-terminal to C-terminal direction a variable light chain region, a constant light chain region, a spacer, and an amyloid reactive peptide and a first and second heavy chain comprising, from N- to C-terminus, a VH, a CH1, a CH2, and a CH3, wherein the CH2 and the CH3 of the first and second heavy chain form a dimer.

In some embodiments, the antibody-peptide fusion protein comprises a light chain comprising, from N- to C-terminus, an amyloid-reactive peptide, a spacer peptide, and a light chain. In some embodiments, the spacer peptide comprises the amino acid sequence of SEQ ID NO:23. In some embodiments, the spacer peptide comprises the amino acid sequence of SEQ ID NO:27. In some embodiments, the spacer peptide comprises an amino acid sequence of SEQ ID NOs: 83-86. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3. In some embodiments, the VH is any one of the VHs described herein. In some embodiments, the antibody-peptide fusion protein comprises a first and second light chain comprising, from N- to C-terminus, an amyloid-reactive peptide, a spacer, a VL, and a CL1, and a first and second heavy chain comprising, from N- to C-terminus, a VH, a CH1, a CH2, and a CH3, wherein the CH2 and the CH3 of the first and second heavy chain form a dimer.

In some embodiments, the antibody-peptide fusion protein comprises a light chain comprising, from N- to C-terminus, a light chain, a spacer peptide, and an amyloid-reactive peptide. In some embodiments, the spacer peptide comprises the amino acid sequence of SEQ ID NO:23. In some embodiments, the spacer peptide comprises the amino acid sequence of SEQ ID NO:27. In some embodiments, the spacer peptide comprises an amino acid sequence of SEQ ID NOs: 83-86. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3. In some embodiments, the VH is any one of the VHs described herein. In some embodiments, the antibody-peptide fusion protein comprises a first and second light chain comprising, from N- to C-terminus, a VL, a CL1, a spacer, and an amyloid-reactive peptide, and a first and second heavy chain comprising, from N- to C-terminus, a VH, a CH1, a CH2, and a CH3, wherein the CH2 and the CH3 of the first and second heavy chain form a dimer.

In some embodiments, the antibody-peptide fusion protein comprises, from N- to C-terminus, a secretory leader peptide, a first spacer peptide, an amyloid-reactive peptide, a second spacer peptide, and a light chain. In some embodiments, the first spacer peptide comprises the amino acid sequence of SEQ ID NO:23. In some embodiments, the first spacer peptide comprises the amino acid sequence of SEQ ID NO:27. In some embodiments, the second spacer peptide comprises the amino acid sequence of SEQ ID NO:24. In some embodiments, the first and/or second spacer peptide comprises an amino acid sequence of SEQ ID NOs: 83-86. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3. In some embodiments, the VH is any one of the VHs described herein. In some embodiments, the VH is any one of the VHs described herein.

In some embodiments, the antibody-peptide fusion protein comprises, from N- to C-terminus, a secretory leader peptide, a first spacer peptide, a light chain, a second spacer peptide, and an amyloid-reactive peptide. In some embodiments, the first spacer peptide comprises the amino acid sequence of SEQ ID NO:23. In some embodiments, the first spacer peptide comprises the amino acid sequence of SEQ ID NO:27. In some embodiments, the second spacer peptide comprises the amino acid sequence of SEQ ID NO:24. In some embodiments, the first and/or second spacer peptide comprises an amino acid sequence of SEQ ID NOs: 83-86. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3. In some embodiments, the VH is any one of the VHs described herein. In some embodiments, the VH is any one of the VHs described herein.

In some embodiments, the antibody-peptide fusion protein comprises a light chain comprising, from N- to C-terminus, a VL and a CL1. In some embodiments, the VL is any one of the VLs described herein. In some embodiments, the antibody-peptide fusion protein comprises a heavy chain comprising, from N- to C-terminus, an amyloid-reactive peptide, VH, a CH1, a CH2, and a CH3. In some embodiments, the VH is any one of the VHs described herein. In some embodiments, the antibody-peptide fusion protein comprises a first and second light chain comprising, from N- to C-terminus, a VL, and a CL1, and a first and second heavy chain comprising, from N- to C-terminus, an amyloid-reactive peptide, a VH, a CH1, a CH2, and a CH3, wherein the CH2 and the CH3 of the first and second heavy chain form a dimer.

In some embodiments, the antibody-peptide fusion protein comprises a light chain comprising, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, a CH3, and an amyloid-reactive peptide. In some embodiments, the VH is any one of the VHs described herein. In some embodiments, the antibody-peptide fusion protein comprises a first and second light chain comprising, from N- to C-terminus, a VL, and a CL1, and a first and second heavy chain comprising, from N- to C-terminus, a VH, a CH1, a CH2, a CH3, and an amyloid-reactive peptide, wherein the CH2 and the CH3 of the first and second heavy chain form a dimer.

In some embodiments, the antibody-peptide fusion protein comprises a light chain comprising, from N- to C-terminus, a VL and a CL1. In some embodiments, the VL is any one of the VLs described herein. In some embodiments, the antibody-peptide fusion protein comprises a heavy chain comprising, from N- to C-terminus, an amyloid-reactive peptide, a spacer peptide, a VH, a CH1, a CH2, and a CH3. In some embodiments, the spacer peptide comprises the amino acid sequence of SEQ ID NO:23. In some embodiments, the spacer peptide comprises the amino acid sequence of SEQ ID NO:27. In some embodiments, the spacer peptide comprises an amino acid sequence of SEQ ID NOs: 83-86. In some embodiments, the VH is any one of the VHs described herein. In some embodiments, the antibody-peptide fusion protein comprises a first and second light chain comprising, from N- to C-terminus, a VL, and a CL1, and a first and second heavy chain comprising, from N- to C-terminus, an amyloid-reactive peptide, a spacer, a VH, a CH1, a CR2, and a CH3, wherein the CH2 and the CH3 of the first and second heavy chain form a dimer.

In some embodiments, the antibody-peptide fusion protein comprises a light chain comprising, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, a CH3, a spacer peptide, and an amyloid-reactive peptide. In some embodiments, the spacer peptide comprises the amino acid sequence of SEQ ID NO:23. In some embodiments, the spacer peptide comprises the amino acid sequence of SEQ ID NO:27. In some embodiments, the spacer peptide comprises an amino acid sequence of SEQ ID NOs: 83-86. In some embodiments, the VH is any one of the VHs described herein. In some embodiments, the antibody-peptide fusion protein comprises a first and second light chain comprising, from N- to C-terminus, a VL, and a CL1, and a first and second heavy chain comprising, from N- to C-terminus, a VH, a CH1, a CH2, a CH3, a spacer, and an amyloid-reactive peptide, wherein the CH2 and the CH3 of the first and second heavy chain form a dimer.

In some embodiments, the antibody-peptide fusion protein comprises a light chain comprising, from N- to C-terminus, an amyloid-reactive peptide, a spacer peptide, and a light chain. In some embodiments, the amyloid-reactive peptide comprises the amino acid sequence of SEQ ID NO:2. In some embodiments, the spacer comprises the amino acid sequences of SEQ ID NO:83. In some embodiments, the light chain comprises a VL comprising the amino acid sequence of SEQ ID NO:36. In some embodiments, the antibody-peptide fusion protein comprises a heavy chain comprising, from N- to C-terminus, a VH, a CH1, a CH2, and a CH3. In some embodiments, the heavy chain comprises a VH comprising the amino acid sequence of SEQ ID NO:55. In some embodiments, the antibody-peptide fusion protein comprises a light chain comprises an amino acid set forth in SEQ ID NO:87, and a heavy chain comprises an amino acid sequence set forth in SEQ ID NO:91. In some embodiments, the antibody-peptide fusion protein comprises a first polypeptide and a second polypeptide comprising an amyloid-reactive peptide linked to the N-terminus of a light chain of an antibody that binds to a human amyloid fibrils, and a third and a fourth polypeptide comprising a heavy chain of an antibody that binds to a human amyloid fibrils, wherein the first polypeptide and second polypeptide comprise the amino acid set forth in SEQ ID NO:87, and the third and fourth polypeptide comprise the amino acid sequence set forth in SEQ ID NO:91. In some embodiments, the antibody-peptide fusion protein comprises a structure as shown in FIG. 1.

Figure 2:
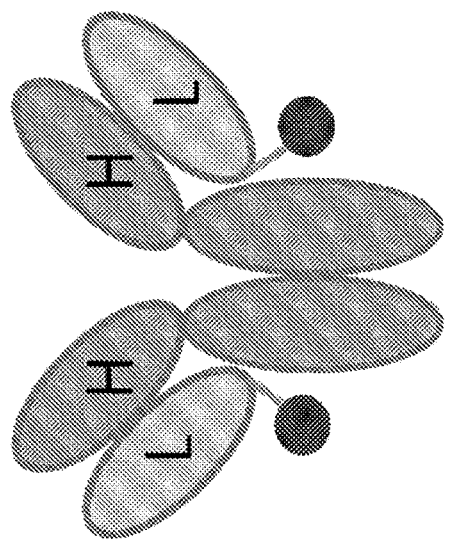
FIG. 2 shows a schematic diagram of an antibody-peptide fusion protein with the peptide fused to the C-terminus of the heavy chain via a short, rigid spacer.

In some embodiments, the antibody-peptide fusion protein comprises a heavy chain comprising, from N- to C-terminus, a heavy chain, a spacer peptide, and an amyloid-reactive peptide. In some embodiments, the amyloid-reactive peptide comprises the amino acid sequence of SEQ ID NO:2. In some embodiments, the spacer comprises the amino acid sequences of SEQ ID NO:83. In some embodiments, the light chain comprises a VL comprising the amino acid sequence of SEQ ID NO:36. In some embodiments, the heavy chain comprises a VH comprising the amino acid sequence of SEQ ID NO:55. In some embodiments, the antibody-peptide fusion protein comprises a light chain comprises an amino acid set forth in SEQ ID NO:88, and a heavy chain comprises an amino acid sequence set forth in SEQ ID NO:92. In some embodiments, the antibody-peptide fusion protein comprises a first polypeptide and a second polypeptide comprising a light chain of an antibody that binds to a human amyloid fibrils, and a third and a fourth polypeptide comprising an amyloid-reactive peptide linked to the C-terminus of a heavy chain of an antibody that binds to a human amyloid fibrils, wherein the first polypeptide and second polypeptide comprise the amino acid set forth in SEQ ID NO:88, and the third and fourth polypeptide comprise the amino acid sequence set forth in SEQ ID NO:92. In some embodiments, the antibody-peptide fusion protein comprises a structure as shown in FIG. 2.

Figure 3:
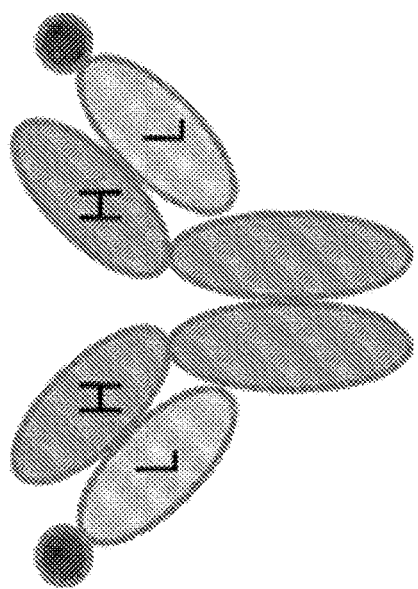
FIG. 3 shows a schematic diagram of an antibody-peptide fusion protein with the peptide fused to the C-terminus of the light chain via a short, rigid spacer.

In some embodiments the antibody peptide fusion comprises a light chain comprising in N-terminal to C-terminal direction a variable light chain region, a constant light chain region, a spacer, and an amyloid reactive peptide. In some embodiments, the amyloid-reactive peptide comprises the amino acid sequence of SEQ ID NO:2. In some embodiments, the spacer comprises the amino acid sequences of SEQ ID NO:83. In some embodiments, the light chain comprises a VL comprising the amino acid sequence of SEQ ID NO:36. In some embodiments, the heavy chain comprises a VH comprising the amino acid sequence of SEQ ID NO: 55. In some embodiments, the antibody-peptide fusion protein comprises a light chain comprises an amino acid set forth in SEQ ID NO:89, and a heavy chain comprises an amino acid sequence set forth in SEQ ID NO:91. In some embodiments, the antibody-peptide fusion protein comprises a first polypeptide and a second polypeptide comprising an amyloid-reactive peptide linked to the C-terminus of a light chain of an antibody that binds to a human amyloid fibrils, and a third and a fourth polypeptide comprising a heavy chain of an antibody that binds to a human amyloid fibrils, wherein the first polypeptide and second polypeptide comprise the amino acid set forth in SEQ ID NO:89, and the third and fourth polypeptide comprise the amino acid sequence set forth in SEQ ID NO:91. In some embodiments, the antibody-peptide fusion protein comprises a structure as shown in FIG. 3.

Figure 4:
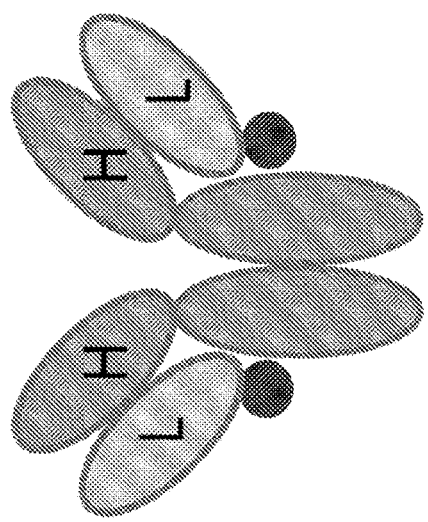
FIG. 4 shows a schematic diagram of an antibody-peptide fusion protein with the peptide fused to the C-terminus of the light chain via a long, flexible spacer.

In some embodiments, the antibody-peptide fusion protein comprises a light chain comprising, from N- to C-terminus, a light chain, a spacer peptide, and an amyloid-reactive peptide. In some embodiments, the amyloid-reactive peptide comprises the amino acid sequence of SEQ ID NO:2. In some embodiments, the spacer comprises the amino acid sequences of SEQ ID NO:86. In some embodiments, the light chain comprises a VL comprising the amino acid sequence of SEQ ID NO:36. In some embodiments, the heavy chain comprises a VH comprising the amino acid sequence of SEQ ID NO:55. In some embodiments, the antibody-peptide fusion protein comprises a light chain comprises an amino acid set forth in SEQ ID NO:90, and a heavy chain comprises an amino acid sequence set forth in SEQ ID NO:91. In some embodiments, the antibody-peptide fusion protein comprises a first polypeptide and a second polypeptide comprising an amyloid-reactive peptide linked to the C-terminus of a light chain of an antibody that binds to human amyloid fibrils, and a third and a fourth polypeptide comprising a heavy chain of an antibody that binds to human amyloid fibrils, wherein the first polypeptide and second polypeptide comprise the amino acid set forth in SEQ ID NO:90, and the third and fourth polypeptide comprise the amino acid sequence set forth in SEQ ID NO:91. In some embodiments, the antibody-peptide fusion protein comprises a structure as shown in FIG. 4.

In some embodiments, the antibody-peptide fusion protein comprises an antibody that binds to amyloid fibrils comprising a first polypeptide and a second polypeptide each comprising a light chain of the antibody, and a third and a forth polypeptide each comprising a heavy chain of the antibody. In some embodiments, the antibody-peptide fusion protein comprises an amyloid-reactive peptide that is linked to the N-terminus or the C-terminus of the light chain or the heavy chain. In some embodiments, the first polypeptide and second polypeptide comprise the amino acid set forth in SEQ ID NO:87, and the third and fourth polypeptide comprise the amino acid sequence set forth in SEQ ID NO:91. In some embodiments, the first polypeptide and second polypeptide comprise the amino acid set forth in SEQ ID NO:88, and the third and fourth polypeptide comprise the amino acid sequence set forth in SEQ ID NO:92. In some embodiments, the first polypeptide and second polypeptide comprise the amino acid set forth in SEQ ID NO:89, and the third and fourth polypeptide comprise the amino acid sequence set forth in SEQ ID NO:91. In some embodiments, the first polypeptide and second polypeptide comprise the amino acid set forth in SEQ ID NO:90, and the third and fourth polypeptide comprise the amino acid sequence set forth in SEQ ID NO:91. In some embodiments, the antibody-peptide fusion protein comprises an antibody linked to an amyloid-reactive peptide via a spacer comprising an amino acid sequence selected from the group consisting of SEQ ID NOs: 23-24, 27, 83-86. In some embodiments, the amyloid-reactive peptide is linked to the antibody via a spacer comprising an amino acid sequence selected from the group consisting of SEQ ID NOs: 83-86. In some embodiments, the amyloid-reactive peptide comprises the amino acid sequence selected from the group consisting of SEQ ID NOs: 1-13. In some embodiments, the amyloid-reactive peptide comprises the amino acid sequence set forth in SEQ ID NO:1 or SEQ ID NO:2. In some embodiments, the amyloid-reactive peptide comprises the amino acid sequence set forth in SEQ ID NO:2. In some embodiments, the antibody-peptide fusion protein comprises an antibody linked to an amyloid-reactive peptide set forth in SEQ ID NO:2 via a spacer comprising an amino acid sequence set forth in SEQ ID NO:83.

In some embodiments, the antibody-peptide fusion protein comprises an amyloid-reactive peptide comprising the amino acid sequence set forth in SEQ ID NO:1 or SEQ ID NO:2. In some embodiments, the antibody-peptide fusion protein comprises an antibody that binds to human amyloid fibrils. In some embodiments, the antibody comprises a variable heavy chain (VH) and a variable light chain (VL) wherein the VH comprises a CDR-H1 comprising the amino acid sequence set forth in SEQ ID NO:17, a CDR-H2 comprising the amino acid sequence set forth in SEQ ID NO:73, and a CDR-H3 comprising the amino acid sequence set forth in SEQ ID NO: 19, and the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22. In some embodiments, the amyloid-reactive peptide and antibody are linked at the C-terminal end of the light chain. In some embodiments, the amyloid-reactive peptide is linked to the antibody via a spacer. In some embodiments the antibody peptide fusion comprises a light chain comprising in N-terminal to C-terminal direction a variable light chain region, a constant light chain region, a spacer, and an amyloid reactive peptide. In some embodiments, the spacer comprises an amino acid sequence selected from the group consisting of SEQ ID NOs: 23-24, 27, 83-86. In some embodiments, the spacer comprises an amino acid sequence selected from the group consisting of SEQ ID NOs: 83-86. In some embodiments, the spacer comprises an amino acid sequence set forth in SEQ ID NO:83.

In some embodiments, the antibody-peptide fusion proteins described herein bind to amyloid deposits or fibrils. In some embodiments, the antibody-peptide fusion protein binds to one or more amyloidogenic peptides in amyloids. In some embodiments, amyloids bound by the antibody-peptide fusion proteins comprise an amyloidogenic λ6 variable domain protein (Vλ6Wil) or an amyloidogenic immunoglobulin light chain (AL), Aβ(1-40) amyloid-like fibril or an amyloidogenic A3 precursor protein, or serum amyloid protein A (AA). In other embodiments, the amyloids bound by the antibody-peptide fusion protein comprise amyloidogenic forms of immunoglobulin heavy chain (AH), P$_2$-microglobulin (Aβ$_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin (ACal), lactadherin (AMed), islet amyloid polypeptide (AIAPP), prolactin (APro), insulin (AIns), prior protein (APrP); α-synuclein (AαSyn), tau (ATau), atrial natriuretic factor (AANF), or IAAP, ALκ4, ALλ1 other amyloidogenic peptides. The amyloidogenic peptides bound by the antibody-peptide fusion proteins can be a protein, a protein fragment, or a protein domain. In some embodiments, the amyloid deposits or amyloid fibrils comprise recombinant amyloidogenic proteins. In some embodiments, the amyloids are part of the pathology of a disease.

In some embodiments, the antibodies provided herein bind specifically to amyloid light chain fibrils. In some embodiments, the amyloid-reactive peptide binds to various amyloid fibrils such as amyloidogenic λ6 variable domain protein (Vλ6Wil) or an amyloidogenic immunoglobulin light chain (AL), Aβ(1-40) amyloid-like fibril or an amyloidogenic Aβ precursor protein, or serum amyloid protein A (AA). In other embodiments, the amyloids bound by the antibody-peptide fusion protein comprise amyloidogenic forms of immunoglobulin heavy chain (AH), β$_2$-microglobulin (Aβ$_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin (ACal), lactadherin (AMed), islet amyloid polypeptide (AIAPP), prolactin (APro), insulin (AIns), prior protein (APrP); α-synuclein (AαSyn), tau (ATau), atrial natriuretic factor (AANF), or IAAP, ALκ4, ALλ1 other amyloidogenic peptides. In some embodiments, the amyloid-reactive peptide binds to heparan sulfate glycosaminoglycans.

In some embodiments, the antibody-peptide fusion proteins described herein bind to amyloid deposits or fibrils. In some embodiments, the amyloid deposits or fibrils are located in one or more organ. In some embodiments, the amyloid deposits are located in one or more tissue type. In some embodiments, the amyloid deposits or fibrils are located in one or more of the liver, spleen, heart, kidney, brain, muscle, pancreas, stomach, upper intestine, lower intestine, and blood. In some embodiments, the antibody-peptide fusion proteins bind to amyloid deposits or fibrils located in at least 1, 2, 3, 4, 5, 6, 7, 8, 9, or 10 organs or tissue types. In some embodiments, the antibody-peptide fusion proteins exhibit pan amyloid reactivity. In some embodiments, the antibody-peptide fusion proteins exhibit reactivity toward amyloid deposits or fibrils located in the liver, spleen, heart, kidney, brain, muscle, pancreas, stomach, upper intestine, lower intestine, and/or blood.

In some embodiments, the antibody-peptide fusion protein comprises an amyloid-reactive peptide comprising the amino acid sequence set forth in SEQ ID NO:1 or SEQ ID NO:2. In some embodiments the antibody peptide fusion comprises a light chain comprising in N-terminal to C-terminal direction a variable light chain region, a constant light chain region, a spacer, and an amyloid reactive peptide. In some embodiments, the antibody-peptide fusion protein comprises an antibody that binds to human amyloid fibrils. In some embodiments, the antibody comprises a variable heavy chain (VH) and a variable light chain (VL) wherein the VH comprises a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO:19, and the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22. In some embodiments, the amyloid-reactive peptide and antibody are linked at the C-terminal end of the light chain. In some embodiments, the amyloid-reactive peptide is linked to the antibody via a spacer. In some embodiments, the spacer comprises an amino acid sequence selected from the group consisting of SEQ ID NOs: 23-24, 27, 83-86. In some embodiments, the spacer comprises an amino acid sequence selected from the group consisting of SEQ ID NOs: 83-86. In some embodiments, the spacer comprises an amino acid sequence set forth in SEQ ID NO:83. In some embodiments, the antibody-peptide fusion protein exhibits pan amyloid reactivity. In some embodiments, the antibody-peptide fusion protein exhibits reactivity toward amyloid deposits or fibrils located in the liver, spleen, heart, kidney, brain, muscle, pancreas, stomach, upper intestine, lower intestine, and/or blood.

In some embodiments, the antibody-peptide fusion proteins described herein bind to amyloid deposits or fibrils with a high binding affinity. In some embodiments, the antibody-peptide fusion proteins described herein bind to amyloid substrates with a high binding affinity. In some embodiments, the binding affinity is less than 500 nM, 400 nM, 300 nM, 200 nM, 100 nM, 50 nM, 40, nM, 30 nM, 20 nM, 10 nM, 5 nM, 4 nM, 3 nM, 2 nM, or 1.5 nM. In some embodiments, the binding affinity is less than 500 nM. In some embodiments, the binding affinity is less than 100 nM. In some embodiments, the binding affinity is less than 10 nM. In some embodiments, the binding affinity is less than 1.5 nM. In some embodiments, the binding affinity is between 0.05 nM and 100 nM, between 0.1 nM and 50 nM, between 0.2 nM and 25 nM, between 0.3 nM and 10 nM, between 0.4 nM and 5 nM, between 0.5 nM and 2 nM, between 0.6 nM and 1 nM, or between 0.2 nM and 1.5 nM. In some embodiments, the binding affinity is the same or different for different amyloid substrates. In some embodiments, the binding affinity is the same or different for human amyloid substrates. In some embodiments, the binding affinity is the same or different for synthetic amyloid substrates.

In some embodiments, the antibody-peptide fusion protein comprises an amyloid-reactive peptide comprising the amino acid sequence set forth in SEQ ID NO:1 or SEQ ID NO:2. In some embodiments, the antibody-peptide fusion protein comprises an antibody that binds to human amyloid fibrils. In some embodiments, the antibody comprises a variable heavy chain (VH) and a variable light chain (VL) wherein the VH comprises a CDR-H1 comprising the amino acid sequence set forth in SEQ ID NO:17, a CDR-H2 comprising the amino acid sequence set forth in SEQ ID NO:73, and a CDR-H3 comprising the amino acid sequence set forth in SEQ ID NO:19, and the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22. In some embodiments, the amyloid-reactive peptide and antibody are linked at the C-terminal end of the light chain. In some embodiments, the amyloid-reactive peptide is linked to the antibody via a spacer. In some embodiments, the spacer comprises an amino acid sequence selected from the group consisting of SEQ ID NOs: 23-24, 27, 83-86. In some embodiments, the spacer comprises an amino acid sequence selected from the group consisting of SEQ ID NOs: 83-86. In some embodiments, the spacer comprises an amino acid sequence set forth in SEQ ID NO:83. In some embodiments, the antibody-peptide fusion proteins described herein bind to amyloid deposits or fibrils with a binding affinity described by an EC50 binding affinity. In some embodiments, the antibody-peptide fusion proteins described herein bind to amyloid substrates with a binding affinity described by an EC50 binding affinity. In some embodiments, the EC50 binding affinity is less than 500 nM, 400 nM, 300 nM, 200 nM, 100 nM, 50 nM, 40, nM, 30 nM, 20 nM, 10 nM, 5 nM, 4 nM, 3 nM, 2 nM, or 1.5 nM. In some embodiments, the EC50 binding affinity is less than 10 nM. In some embodiments, the EC50 binding affinity is less than 1.5 nM. In some embodiments, the EC50 binding affinity is the same or different for different amyloid substrates. In some embodiments, the EC50 binding affinity is the same or different for human amyloid substrates. In some embodiments, the EC50 binding affinity is the same or different for synthetic amyloid substrates.

As those skilled in the art will appreciate, the fragment antigen binding (or Fab region) is the head of an antibody that naturally interacts with target antigen. Components of the Fab region, for example, allow antibodies to bind to specific ligands and, through that interaction, to further activate the immune system. For IgG, IgA, IgD, IgE, and IgM antibody isotypes, the Ig is composed of two proteins, the heavy chain and light chain that interact in pairs to form an intact Ig comprising 2 heavy chains and 2 light chains. Both the heavy and light chains are further divided into variable domains and constant domains—the light and heavy variable domains comprising the Fab functional region and the heavy chains forming the fragment crystallizable (Fc) domains that interact with cell receptors and complement. The Fc regions of Ig bears a highly conserved N-glycosylation site.

In certain example embodiments, one or more of the peptides shown in Table 1 below can be linked to an antibody or functional fragment thereof through the C- or N-terminus of the light chain protein or the C- or N-terminus of the heavy chain, thereby forming an antibody-peptide fusion protein. That is, any of the sequences identified below in Table 1 can be linked to the heavy or light chain of the antibody or functional fragment thereof independently or simultaneously to form a peptide-antibody conjugate. For example, two of the amyloid-reactive peptides can be linked with a single antibody, such by joining the amyloid-reactive peptide amino acid sequences to the N-terminal of the Ig light chain proteins.

In certain example embodiments, recombinant DNA technology may be employed wherein a nucleotide sequence that encodes a peptide of the invention is cloned, fused to an Ig light chain, into an expression vector, transformed or transfected into an appropriate host cell, and cultivated under conditions suitable or expression. The peptide-Ig light chain fusion is then isolated. Advantageously, and as those skilled in the art will appreciate in view of this disclosure, the methods described herein can be used to join any peptide sequence to the antibody. That is, while amyloid-reactive peptides are used as an example of a peptide linked to the antibody, the method of linking a peptide to an antibody—such as to the N and/or C-terminal end of the light chain protein and/or the N and/or C-terminal end of the Ig heavy chain protein—can be used for a variety of different peptides to join the peptide to the antibodies.

In certain example embodiments, multiple of the same or different peptides can be linked to a single antibody or functional fragment thereof. For example, a first expression vector can include a light chain nucleic acid sequence that is integrated with a nucleic acid sequence encoding Peptide A, with the nucleic acid sequence for Peptide A positioned in the vector such that the Peptide A is expressed as linked to the N-terminal of the light chain protein. Further, a second expression vector can include a heavy chain nucleic acid sequence that is integrated with a nucleic acid sequence encoding Peptide B, with the nucleic acid sequence for Peptide B positioned in the vector such that Peptide B is expressed as linked to the N-terminal of the light chain protein.

In such example embodiments, when both expression vectors are expressed within the same cell, the resulting Ig protein can have one Peptide A sequence on the N-terminal of each light chain (for a total of two Peptide As) and a Peptide B on the N-terminal of the heavy chain. In certain example embodiments, the vector may include a Peptide C on the C-terminal end, thereby resulting in an antibody having two Peptide A sequences (one on each light chain), a Peptide B sequence on the N-terminal end of the heavy chain, and a Peptide C sequence linked to the C-terminal end of the heavy chain. As such, and as one skilled in the art will appreciate based on this disclosure, the expression vectors can be tailored to modify the immunoglobulin to have the same or different combinations of proteins. As a specific example using an amyloid-reactive peptide, an antibody-peptide fusion protein may include two p5 proteins sequences (SEQ ID NO: 1), i.e., one on each light chain N-terminal end. In other example embodiments, the peptides linked to the immunoglobulin may have an affinity to a ligand, and hence can be used to detect the ligand.

In some embodiments, the antibody-peptide fusion protein comprising a humanized antibody of the present disclosure comprises an Fe region. In some embodiments, the Fe is of an IgG1, IgG2, IgG3, or IgG4 isotype. In some embodiments, the antibody-peptide fusion protein comprising a humanized antibody promotes an Fc-mediated antibody effector function. In some embodiments, the antibody-peptide fusion protein comprising a humanized antibody promotes antibody-dependent cellular phagocytosis.

In some embodiments, the antibody-peptide fusion protein binds to human amyloid fibrils with a dissociation constant (Kd) that is less than about 100, 10, 1, 0.1, 0.01 µM. In some embodiments, the antibody-peptide fusion protein binds to human amyloid fibrils with a Kd that is about 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 50, 75, or 100 µM including any value or range between these values. In some embodiments, the antibody-peptide fusion protein binds to human amyloid fibrils with a Kd that is less than 500, 100, 10, or 1 nM. In some embodiments, the antibody-peptide fusion protein binds to human amyloid fibrils with a Kd that is less than about 5, 10, 20, 30, 40, 50, 60, 70, 80, 90, 100, 250, 500, 750, 1000, 2000, or 2200 nM. In some embodiments, the antibody-peptide fusion protein binds to human amyloid fibrils with a Kd that is about 5, 10, 20, 30, 40, 50, 60, 70, 80, 90, 100, 250, 500, 750, 1000, 2000, or 2200 nM, including any value or range between these values. In some embodiments, the antibody-peptide fusion protein binds to human amyloid fibrils with a Kd that is about 40-50 nM. In some embodiments, the antibody-peptide fusion protein binds to human amyloid fibrils with a Kd that is 40-50 nM. In some embodiments, the antibody-peptide fusion protein binds to human amyloid fibrils with a Kd that is less than 50 nM. In some embodiments, the antibody-peptide fusion protein binds to human amyloid fibrils with a Kd that is less than the Kd of c11-1F4 binding to human amyloid fibrils.

In some embodiments, the antibody-peptide fusion protein binds to human amyloid fibrils with half-maximal binding at a concentration of antibody ($EC_{50}$) that is less than about 0.01, 0.1, or 1 µM. In some embodiments, the antibody-peptide fusion protein binds to human amyloid fibrils with half-maximal binding at a concentration of antibody ($EC_{50}$) that is about 0.001, 0.01, 0.05, 0.1, 0.2, 0.3, 0.4, 0.5, 0.6, 0.7, 0.8, 0.9, 1, 2, 3, 4, 5, 6, 7, 8, 9, or 10 µM, including any value or range between these values. In some embodiments, the antibody-peptide fusion protein binds to human amyloid fibrils with half-maximal binding at a concentration of antibody ($EC_{50}$) that is less than about 1, 10, 100, or 1000 nM. In some embodiments, the antibody-peptide fusion protein binds to human amyloid fibrils with half-maximal binding at a concentration of antibody ($EC_{50}$) that is about 1, 5, 10, 15, 20, 25, 30, 35, 40, 45, 50, 55, 60, 65, 70, 75, 80, 85, 90, 95, 100, 100, 250, 500, 750, or 1000 nM, including any value or range between these values. In some embodiments, the antibody-peptide fusion protein binds to human amyloid fibrils with half-maximal binding at a concentration of antibody ($EC_{50}$) that is about 17 nM, 7 nM, 16 nM, 75 nM, or 95 nM. In some embodiments, the antibody-peptide fusion protein binds to human amyloid fibrils with half-maximal binding at a concentration of antibody ($EC_{50}$) that is less than about 10 nM, 20 nM, 80 nM, or 100 nM. In some embodiments, the antibody-peptide fusion protein binds to human amyloid fibrils with half-maximal binding at a concentration of antibody ($EC_{50}$) that is less than the $EC_{50}$ of c11-1F4 binding to human amyloid fibrils.

Methods for calculating dissociation constants and $EC_{50}$s are known in the art, and include, for example, surface plasmon resonance and europium-linked immunosorbant assays (EuLISAs). In some embodiments, the dissociation constant is determined by measuring binding to a Len(1-22) monomer peptide, for example, using surface plasmon resonance. In some embodiments, the $EC_{50}$ is determined using a EuLISA. In some embodiments, the $EC_{50}$ is determined using a EuLISA to measure the level of binding to rVλ6Wil fibrils, Per125 wtATTR extract, Ken ATTR extract, SHI ALλ liver extract, or TAL ALκ liver extract.

In some embodiments, the antibody-peptide fusion protein is conjugated to a detectable label. In some embodiments, the detectable label is selected from the group consisting of radionuclides (e.g., $I^{-125}$, $I^{-123}$, $I^{-124}$, $I^{-131}$, $Zr^{-89}$, $Tc^{-99m}$, $Cu^{-64}$, $Br^{-76}$, $F^{-18}$); enzymes (horse radish peroxidase); biotin; and fluorophores, etc. Any means known in the art for detectably labeling a protein can be used and/or adapted for use with the methods described herein. For example, the antibody-peptide fusion proteins, can be radiolabeled with a radioisotope, or labeled with a fluorescent tag or a chemiluminescent tag. Example radioisotopes include, for example, $^{18}F$, $^{111}In$, $^{99m}Tc$, and $^{123}I$, and $^{125}I$ These and other radioisotopes can be attached to the antibody-peptide fusion protein using well known chemistry that may or not involve the use of a chelating agent, such as DTPA or DOTA covalently linked to the light chain protein of the antibody-peptide fusion protein, for example. Example fluorescent or chemiluminescent tags include fluorescein, Texas red, rhodamine, Alexa dyes, and luciferase that can be conjugated to the antibody-peptide fusion protein by reaction with lysine, cysteine, glutamic acid, and aspartic acid side chains. In one example embodiment, the label is detected using a fluorescent microplate reader, or fluorimeter, using the excitation and emission wavelengths appropriate for the tag that is used. Radioactive labels can be detected, for example, using a gamma or scintillation counter depending on the type of radioactive emission and by using energy windows suitable for the accurate detection of the specific radionuclide. However, any other suitable technique for detection of radioisotopes can also be used to detect the label. In some embodiments, the detectable label is $^{125}I$.

In some embodiments, the antibody-peptide fusion protein binds to rVλ6Wil fibrils, Per125 wtATTR extract, KEN hATTR extract, SHI ALλ liver extract, and/or TAL ALκ liver extract. In some embodiments, the antibody-peptide fusion proteins described herein bind to amyloid deposits or fibrils. In some embodiments, the antibody-peptide fusion protein binds to one or more amyloidogenic peptides in amyloids. In some embodiments, amyloids bound by the antibody-peptide fusion protein comprise an amyloidogenic λ6 variable domain protein (Vλ6Wil) or an amyloidogenic immunoglobulin light chain (AL), Aβ(1-40) amyloid-like fibril or an amyloidogenic A3 precursor protein, or serum amyloid protein A (AA). In other embodiments, the amyloids bound by the antibody-peptide fusion protein comprise amyloidogenic forms of immunoglobulin heavy chain (AH), $P_2$-microglobulin (Aβ$_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin ((ACal), lactadherin (AMed), islet amyloid polypeptide (AIAPP), prolactin (APro), insulin (AIns), prior protein (APrP); α-synuclein (AαSyn), tau (ATau), atrial natriuretic factor (AANF), or IAAP, ALκ4, Alλ1 other amyloidogenic peptides. The amyloidogenic peptides bound by the antibody-peptide fusion protein can be a protein, a protein fragment, or a protein domain. In some embodiments, the amyloid deposits or amyloid fibrils comprise recombinant amyloidogenic proteins. In some embodiments, the amyloids are part of the pathology of a disease.

In some embodiments, binding of the antibody-peptide fusion protein to human amyloid promotes the phagocytosis of human amyloid fibrils. In some embodiments, the antibody-peptide fusion protein opsonizes human amyloid fibrils. In some embodiments, the antibody-peptide fusion protein opsonizes rVλ6Wil fibrils. In some embodiments, contacting human amyloid fibrils with an antibody-peptide fusion protein of the present disclosure in the presence of macrophages promotes the uptake of the human amyloid fibrils by the macrophages. In some embodiments, contacting human amyloid fibrils with an antibody-peptide fusion protein of the present disclosure in the presence of macrophages promotes the opsonization of the human amyloid fibrils. In some embodiments, binding of the antibody-peptide fusion protein to human amyloid promotes the phagocytosis of human amyloid fibrils to an equal or greater extent than a control antibody (e.g., hIgG and/or c11-1F4). In some embodiments, the antibody-peptide fusion protein promotes antibody-dependent cellular phagocytosis.

In some embodiments, the antibody-peptide fusion protein exhibits one or more in vivo features selected from among improved biodistribution, pan amyloid reactivity, and enhanced phagocytosis compared to a reference antibody. In some embodiments, the antibody-peptide fusion protein exhibits improved biodistribution compared to reference antibody, wherein the antibody-peptide fusion protein is detectable in organs across the body. In some embodiments, the antibody-peptide fusion protein exhibits improved biodistribution, wherein the antibody-peptide fusion protein is detectable in one or more of the liver, spleen, heart, kidney, brain, muscle, pancreas, stomach, upper intestine, lower intestine, and blood. In some embodiments, the antibody-peptide fusion protein exhibits pan amyloid reactivity compared to reference antibody, wherein the antibody-peptide fusion protein is reactive towards one or more distinct amyloid substrates in vivo. In some embodiments, the antibody-peptide fusion protein is reactive towards amyloid substrates in the liver, spleen, heart, kidney, brain, muscle, pancreas, stomach, upper intestine, lower intestine, and blood, In some embodiments, the antibody-peptide fusion protein exhibits enhanced phagocytosis compared to reference antibody, wherein contacting an amyloid substrate in vivo with the antibody-peptide fusion protein results in increased levels of phagocytosis. In some embodiments, contacting an amyloid substrate in vivo with the antibody-peptide fusion protein results in clearance of the amyloid substrate. In some embodiments, contacting an amyloid substrate in vivo with the antibody-peptide fusion protein results in enhanced phagocytosis and clearance of the amyloid substrate. In some embodiments, contacting an amyloid substrate in vivo with the antibody-peptide fusion protein provides therapeutic benefit for an individual having an amyloid related disorder. In some embodiments, the reference antibody is not engineered to bind amyloid substrates. In some embodiments, the reference antibody does not comprise an amyloid-reactive peptide. In some embodiments, the reference antibody is not fused to an amyloid-reactive peptide. In some embodiments, the reference antibody serves as a negative control. In some embodiments, the reference antibody is an IgG antibody. In some embodiments, the reference antibody is an IgG1, IgG2, IgG3, or IgG4 isotype. In some embodiments, the reference antibody is an IgG1 isotype.

Also provided herein are compositions comprising an antibody-peptide fusion protein comprising an amyloid reactive-peptide and an antibody that binds to human amyloid fibrils. In some embodiments, the antibody comprises a heavy chain comprising a heavy chain variable region (VH) and a light chain comprising a light chain variable region (VL). In some embodiments, the amyloid-reactive peptide and antibody are linked at the N-terminal end of the heavy chain. In some embodiments, the amyloid-reactive peptide and antibody are linked at the C-terminal end of the heavy chain. In some embodiments, the amyloid-reactive peptide and antibody are linked at the N-terminal end of the light chain. In some embodiments, the amyloid-reactive peptide and antibody are linked at the C-terminal end of the light chain. In some embodiments, the amyloid-reactive peptide is linked to the antibody via a spacer, or without a spacer. In some embodiments, the composition comprises the antibody-peptide fusion protein, wherein at least 80% of the antibody-peptide fusion protein is intact. In some embodiments, the composition comprises the antibody-peptide fusion protein, wherein at least 80%, 85%, 90%, 91%, 92%, 93%, 94%, 95%, 96%, 97%, 98%, 99%, or 99.5% of the antibody-peptide fusion protein is intact. In some embodiments, an intact antibody-peptide fusion protein is one that has not been subject to proteolytic degradation. In some embodiments, the intact antibody-peptide fusion protein consists of the full length antibody-peptide fusion protein. In some embodiments, the intact antibody-peptide fusion protein comprises the full length amino acid sequence selected from the group consisting of SEQ ID NOs:87-92. In some embodiments, the antibody is a full length antibody.

In some embodiments, the composition has a purity that is defined by the amount of intact antibody-peptide fusion protein present in the composition. In some embodiments, an intact antibody-peptide fusion protein is one that has not been subject to proteolytic degradation. In some embodiments, the intact antibody-peptide fusion protein consists of the full length antibody-peptide fusion protein. In some embodiments, the intact antibody-peptide fusion protein comprises the full length amino acid sequence selected from the group consisting of SEQ ID NOs:87-92. In some embodiments, the composition has a purity of at least 80%. For example, the composition having a purity of 80% comprises 80% intact antibody-peptide fusion protein. In some embodiments, the composition has a purity of at least 80%, 85%, 90%, 91%, 92%, 93%, 94%, 95%, 96%, 97%, 98%, 99%, or 99.5%. In some embodiments, the intact antibody-peptide fusion protein consists of the full length antibody-peptide fusion protein. In some embodiments, the intact antibody-peptide fusion protein comprises an amino acid sequence selected from the group consisting of SEQ ID NOs:87-92.

In some embodiments, the composition comprises an antibody-peptide fusion protein comprising an amyloid reactive-peptide and an antibody that binds to human amyloid fibrils. In some embodiments, the antibody comprises a heavy chain comprising a heavy chain variable region (VH) and a light chain comprising a light chain variable region (VL). In some embodiments, the amyloid-reactive peptide and antibody are linked at the N-terminal end of the heavy chain. In some embodiments, the amyloid-reactive peptide and antibody are linked at the C-terminal end of the heavy chain. In some embodiments, the amyloid-reactive peptide and antibody are linked at the N-terminal end of the light chain. In some embodiments, the amyloid-reactive peptide and antibody are linked at the C-terminal end of the light chain. In some embodiments, the amyloid-reactive peptide is linked to the antibody via a spacer, or without a spacer.

In some embodiments, the composition described herein comprises no more than 20% of a cleavage product. In some embodiments, the cleavage product comprises a light chain lacking one or more amino acid residues from the N-terminus or C-terminus. In some embodiments the cleavage produce comprises a light chain comprising in N-terminal to C-terminal direction a variable light chain region, a constant light chain region, a spacer, and an amyloid reactive peptide. In some embodiments, the cleavage product comprises an amyloid-reactive peptide lacking one or more amino acid residues from the C-terminus. In some embodiments, the cleavage product comprises an antibody linked to an amyloid-reactive peptide, wherein the antibody or the amyloid-reactive peptide lacks one or more residues at the N or C terminus. In some embodiments the cleavage produce comprises a light chain comprising in N-terminal to C-terminal direction an amyloid-reactive peptide, a spacer, a variable light chain region, and a constant light chain region. In some embodiments, the cleavage product comprises an amyloid-reactive peptide lacking one or more amino acid residues from the N-terminus. In some embodiments, the cleavage product comprises a heavy chain lacking one or more amino acid residues from the N-terminus or C-terminus. In some embodiments, the composition described herein comprises no more than 20%, 15%, 12%, 10%, 9%, 8%, 7%, 6%, 5%, 4%, 3%, 2%, 1%, or 0.5% of the cleavage product.

In some embodiments, the composition described herein comprises no more than 20% of a cleavage product. In some embodiments, the cleavage product comprises a light chain lacking one or more amino acid residues from the N-terminus compared to the amino acid sequence set forth by SEQ ID NOs: 87-90. In some embodiments, the cleavage product comprises a light chain comprising an amyloid-reactive peptide lacking one or more amino acid residues from the N-terminus compared to the amino acid sequence set forth by SEQ ID NO:87. In some embodiments, the cleavage product comprises a light chain lacking one or more amino acid residues from the C-terminus compared to the amino acid sequence set forth by SEQ ID NO: 87-90. In some embodiments, the cleavage product comprises a light chain comprising an amyloid-reactive peptide lacking one or more amino acid residues from the C-terminus compared to the amino acid sequence set forth by SEQ ID NOs: 89-90. In some embodiments, the cleavage product comprises a heavy chain lacking one or more amino acid residues from the N-terminus compared to the amino acid sequence set forth by SEQ ID NOs: 91-92. In some embodiments, the cleavage product comprises a heavy chain lacking one or more amino acid residues from the C-terminus compared to the amino acid sequence set forth by SEQ ID NO: 91-92. In some embodiments, the cleavage product comprises a heavy chain comprising an amyloid-reactive peptide lacking one or more amino acid residues from the C-terminus compared to the amino acid sequence set forth by SEQ ID NO:92. In some embodiments, the cleavage product comprises a light chain or a heavy chain comprising an amyloid-reactive peptide lacking one or more amino acid residues from the N-terminus or C-terminus. In some embodiments, the composition described herein comprises no more than 20%, 15%, 12%, 10%, 9%, 8%, 7%, 6%, 5%, 4% 3%, 2%, 1%, or 0.5% of the cleavage product.

In some embodiments, the composition described herein comprises no more than 20% of a cleavage product. In some embodiments, the cleavage product comprises a light chain lacking one or more amino acid residues from the N-terminus compared to the amino acid sequence set forth by SEQ ID NO:89. In some embodiments, the cleavage product comprises a light chain lacking one or more amino acid residues from the C-terminus compared to the amino acid sequence set forth by SEQ ID NO:89. In some embodiments, the cleavage product comprises an amyloid-reactive peptide lacking one or more amino acid residues from the C-terminus. In some embodiments, the cleavage product comprises an antibody fused to an amyloid reactive peptide, wherein the amyloid reactive peptide is truncated by 1, 2, 3, 4, 5, 6, 7, 8, 9, 10, or 15 amino acids. In some embodiments, the cleavage product comprises a heavy chain lacking one or more amino acid residues from the N-terminus compared to the amino acid sequence set forth in SEQ ID NO:91. In some embodiments, the cleavage product lacks at least 1, 2, 3, 4, 5, 6, 7, 8, 9, 10, or 15 amino acids at the N or C terminus compared to the intact fusion protein. In some embodiments, the cleavage product comprises a heavy chain lacking one or more amino acid residues from the C-terminus compared to the amino acid sequence set forth in SEQ ID NO:91. In some embodiments, the composition described herein comprises no more than 20%, 15%, 12%, 10%, 9%, 8%, 7%, 6%, 5%, 4%, 3%, 2%, 1%, or 0.5% of the cleavage product.

In some embodiments, the composition described herein comprises no more than 20% of a cleavage product. In some embodiments, the cleavage product comprises a light chain lacking one or more amino acid residues from the N-terminus compared to the amino acid sequence set forth by SEQ ID NO:87. In some embodiments, the cleavage product comprises an amyloid-reactive peptide lacking one or more amino acid residues from the N-terminus. In some embodiments, the cleavage product comprises a light chain lacking one or more amino acid residues from the C-terminus compared to the amino acid sequence set forth by SEQ ID NO:87. In some embodiments, the cleavage product comprises a heavy chain lacking one or more amino acid residues from the N-terminus compared to the amino acid sequence set forth in SEQ ID NO:91. In some embodiments, the cleavage product comprises a heavy chain lacking one or more amino acid residues from the C-terminus compared to the amino acid sequence set forth in SEQ ID NO:91. In some embodiments, the composition described herein comprises no more than 20%, 15%, 12%, 10%, 9%, 8%, 7%, 6%, 5%, 4%, 3%, 2%, 1%, or 0.5% of the cleavage product.

In some embodiments, the composition described herein comprises no more than 20% of a cleavage product. In some embodiments, the cleavage product comprises a light chain lacking one or more amino acid residues from the N-terminus compared to the amino acid sequence set forth by SEQ ID NO:88. In some embodiments, the cleavage product comprises a light chain lacking one or more amino acid residues from the C-terminus compared to the amino acid sequence set forth by SEQ ID NO:88. In some embodiments, the cleavage product comprises a heavy chain lacking one or more amino acid residues from the N-terminus compared to the amino acid sequence set forth in SEQ ID NO:92. In some embodiments, the cleavage product comprises a heavy chain lacking one or more amino acid residues from the C-terminus compared to the amino acid sequence set forth in SEQ ID NO:92. In some embodiments, the cleavage product comprises an amyloid-reactive peptide lacking one or more amino acid residues from the C-terminus. In some embodiments, the composition described herein comprises no more than 20%, 15%, 12%, 10%, 9%, 8%, 7%, 6%, 5%, 4%, 3%, 2%, 1%, or 0.5% of the cleavage product.

In some embodiments, the composition described herein comprises no more than 20% of a cleavage product. In some embodiments, the cleavage product comprises a light chain lacking one or more amino acid residues from the N-terminus compared to the amino acid sequence set forth by SEQ ID NO:90. In some embodiments, the cleavage product comprises a light chain lacking one or more amino acid residues from the C-terminus compared to the amino acid sequence set forth by SEQ ID NO:90. In some embodiments, the cleavage product comprises an amyloid-reactive peptide lacking one or more amino acid residues from the C-terminus. In some embodiments, the cleavage product comprises a heavy chain lacking one or more amino acid residues from the N-terminus compared to the amino acid sequence set forth in SEQ ID NO:91. In some embodiments, the cleavage product comprises a heavy chain lacking one or more amino acid residues from the C-terminus compared to the amino acid sequence set forth in SEQ ID NO:91. In some embodiments, the composition described herein comprises no more than 20%, 15%, 12%, 10%, 9%, 8%, 7%, 6%, 5%, 4%, 3%, 2%, 1%, or 0.5% of the cleavage product.

In some embodiments, the composition comprises an antibody-peptide fusion protein, wherein the antibody-peptide fusion protein exhibits an EC50 binding affinity for one or more amyloid substrate. In some embodiments, the EC50 binding affinity is less than 500 nM, 400 nM, 300 nM, 200 nM, 100 nM, 50 nM, 40, nM, 30 nM, 20 nM, 10 nM, 5 nM, 4 nM, 3 nM, 2 nM, or 1.5 nM. In some embodiments, the EC50 binding affinity is about or less than 100 nM. In some embodiments, the EC50 binding affinity is about or less than 10 nM. In some embodiments, the EC50 binding affinity is about or less than 1.5 nM. In some embodiments, the EC50 binding affinity is the same or different for different amyloid substrates. In some embodiments, the EC50 binding affinity is the same or different for human amyloid substrates. In some embodiments, the EC50 binding affinity is the same or different for synthetic amyloid substrates.

In some embodiments, the composition comprises an antibody-peptide fusion protein, wherein the antibody-peptide fusion protein exhibits one or more in vivo features selected from among improved biodistribution, pan amyloid reactivity, and enhanced phagocytosis compared to reference antibody. In some embodiments, the antibody-peptide fusion protein exhibits improved biodistribution compared to reference antibody, wherein the antibody-peptide fusion protein is detectable in organs across the body. In some embodiments, the antibody-peptide fusion protein exhibits improved biodistribution, wherein the antibody-peptide fusion protein is detectable in one or more of the liver, spleen, heart, kidney, brain, muscle, pancreas, stomach, upper intestine, lower intestine, and blood. In some embodiments, the antibody-peptide fusion protein exhibits pan amyloid reactivity compared to reference antibody, wherein the antibody-peptide fusion protein is reactive towards one or more distinct amyloid substrates in vivo. In some embodiments, the antibody-peptide fusion protein is reactive towards amyloid substrates in the liver, spleen, heart, kidney, brain, muscle, pancreas, stomach, upper intestine, lower intestine, and blood, In some embodiments, the antibody-peptide fusion protein exhibits enhanced phagocytosis compared to reference antibody, wherein contacting an amyloid substrate in vivo with the antibody-peptide fusion protein results in increased levels of phagocytosis. In some embodiments, contacting an amyloid substrate in vivo with the antibody-peptide fusion protein results in clearance of the amyloid substrate. In some embodiments, contacting an amyloid substrate in vivo with the antibody-peptide fusion protein results in enhanced phagocytosis and clearance of the amyloid substrate. In some embodiments, contacting an amyloid substrate in vivo with the antibody-peptide fusion protein provides therapeutic benefit for an individual having an amyloid related disorder. In some embodiments, the reference antibody does not bind amyloid substrates. In some embodiments, the reference antibody does not comprise an amyloid-reactive peptide. In some embodiments, the reference antibody is an IgG antibody. In some embodiments, the reference antibody is an IgG1, IgG2, IgG3, or IgG4 isotype. In some embodiments, the reference antibody is an IgG1 isotype.

In some embodiments, the composition further comprises a pharmaceutically acceptable carrier. In some embodiments, the pharmaceutically acceptable carrier may be a liquid or solid filler, diluent, excipient, solvent, or encapsulating material, or a combination thereof.

In various embodiments, the compositions according to the disclosure may be formulated for delivery via any route of administration. This may include e.g., aerosol, nasal, oral, transmucosal, transdermal, parenteral or enteral. In some embodiments, administration is intravenous or subcutaneous.

Provided are pharmaceutical formulations including the antibody-peptide fusion protein antibody. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used.

The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Also provided herein are pharmaceutical compositions comprising any of the antibody-peptide fusion proteins described herein. In some embodiments, the pharmaceutical composition further comprises a pharmaceutically acceptable carrier.

In certain example embodiments, the antibody-peptide fusion protein may be obtained by isolation or purification. Protein purification techniques involve, at one level, the homogenization and crude fractionation of cells, tissue, or organ to peptide and non-peptide fractions. Other protein purification techniques include, for example, precipitation with ammonium sulfate, polyethylene glycol (PEG), antibodies and the like, or by heat denaturation, followed by: centrifugation; chromatography steps such as ion exchange, gel filtration, reverse phase, hydroxylapatite and affinity chromatography; isoelectric focusing; gel electrophoresis, for example polyacrylamide gel electrophoresis; and combinations of these and other techniques.

Various chromatographic techniques include but are not limited to ion-exchange chromatography, gel exclusion chromatography, affinity chromatography, immuno-affinity chromatography, and reverse phase chromatography. A particularly efficient method of purifying peptides is fast performance liquid chromatography (FPLC) or even high-performance liquid chromatography (HPLC). In certain example embodiments, the Fc domain may be linked to the amyloid-reactive peptide via a GGGYS linker sequence (SEQ ID NO:27).

III. DIAGNOSTIC AND DETECTION METHODS

Also provided herein are methods of identifying an amyloid deposit in a subject.

In some embodiments, provided herein is a method of identifying an amyloid deposit in a subject, comprising administering any one of the antibody-peptide fusion proteins described herein to the subject, wherein the antibody-peptide fusion protein comprises a detectable label, and detecting a signal from the antibody peptide fusion protein. Any one of the detectably-labeled antibody-peptide fusion proteins described herein may be used. In some embodiments, the subject is determined to be amyloid free or suffering from monoclonal gammopathy of unknown significance (MGUS), multiple myeloma (MM), or one or more related plasma cell diseases. In some embodiments, the antibody-peptide fusion protein comprises an amyloid-reactive peptide comprising the amino acid sequence set forth in SEQ ID NO:1 or SEQ ID NO:2. In some embodiments, the antibody-peptide fusion protein comprises an antibody that binds to human amyloid fibrils. In some embodiments, the antibody comprises a variable heavy chain (VH) and a variable light chain (VL) wherein the VH comprises a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO:19, and the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22. In some embodiments, the amyloid-reactive peptide and antibody are linked at the N-terminal end or the C-terminal end of the light chain. In some embodiments, the amyloid-reactive peptide and antibody are linked at the N-terminal end or the C-terminal end of the heavy chain. In some embodiments, the amyloid-reactive peptide is linked to the antibody via a spacer. In some embodiments, the spacer comprises an amino acid sequence selected from the group consisting of SEQ ID NOs: 23-24, 27, 83-86. In some embodiments, the spacer comprises an amino acid sequence selected from the group consisting of SEQ ID NOs: 83-86. In some embodiments, the spacer comprises an amino acid sequence set forth in SEQ ID NO:83. In some embodiments, the antibody is a full length antibody.

In some embodiments, provided herein is a method of detecting a ligand, comprising: contacting the ligand with any one of the antibody-peptide fusion proteins described herein, wherein the antibody-peptide fusion protein comprises a detectable label, wherein the peptide of the antibody-peptide fusion protein has binding affinity to the ligand and, determining a signal from the detectable label, thereby detecting the ligand. Any one of the detectably-labeled antibody-peptide fusion proteins described herein may be used.

In some embodiments, the antibody-peptide fusion proteins can be labeled with various agents to allow their detection in vivo and in in vitro assays, such as after the fusion peptides are purified. Without being limited this may include radionuclides (e.g., I-$^{125}$, I-$^{123}$, I-$^{131}$, Zr-$^{89}$, Tc-$^{99m}$, Cu-$^{64}$, Br-$^{76}$, F-$^{18}$); enzymes (horse radish peroxidase); biotin; fluorophores, etc. Any means known in the art for detectably labeling a protein can be used and/or adapted for use with the methods described herein. For example, the antibodies or fragments thereof, and/or the amyloid-reactive peptides, can be radiolabeled with a radioisotope, or labeled with a fluorescent tag or a chemiluminescent tag. Example radioisotopes include, for example, $^{18}$F, $^{111}$In, $^{99m}$Tc, and $^{123}$I, and $^{125}$I. These and other radioisotopes can be attached to the isolated immunoglobulin light chain using well known chemistry that may or not involve the use of a chelating agent, such as DTPA or DOTA covalently linked to the light chain protein of the antibody, for example. Example fluorescent or chemiluminescent tags include fluorescein, Texas red, rhodamine, Alexa dyes, and luciferase that can be conjugated to the protein by reaction with lysine, cysteine, glutamic acid, and aspartic acid side chains. In one example embodiment, the label is detected using a fluorescent microplate reader, or fluorimeter, using the excitation and emission wavelengths appropriate for the tag that is used. Radioactive labels can be detected, for example, using a gamma or scintillation counter depending on the type of radioactive emission and by using energy windows suitable for the accurate detection of the specific radionuclide. However, any other suitable technique for detection of radioisotopes can also be used to detect the label.

With regard to amyloidosis, such labeling, for example, can be used to diagnose the presence of amyloid, to determine the amyloid protein load, to monitor the ability of the antibody-peptide fusion proteins to bind amyloid in a particular subject, to monitor the progression of amyloidosis, and/or to monitor a subject's response to an amyloid treatment (including treatments associated with the administration of the antibody-peptide fusion proteins to the subject). For example, antibody-peptide fusion proteins are labeled with a detectable label as described herein and thereafter administered to a subject that is suffering from, or suspected to be suffering from, an amyloid-based disease (e.g., amyloidosis, monoclonal gammopathy of unknown significance (MGUS), multiple myeloma (MM), or related plasma cell diseases). Thereafter, the subject can be imaged, for example, to detect the presence of the antibody-peptide fusion proteins.

In certain example embodiments, the signals from the detectably-labeled antibody-peptide fusion proteins can be quantified, thereby providing an indication of the level of amyloid deposit in the subject. For example, the signal intensity may be compared to a standard signal threshold, above which amyloidosis is present but below which amyloidosis is absent or at a low level. The subject can be diagnosed as having amyloid, in which case a treatment can be administered, such as such as chemotherapy, corticosteroid medicines (lenalidomide or thalidomide) and/or bortezomib (Velcade). Additionally or alternatively, the antibody-peptide fusion proteins described herein can be administered to the subject in an effort to treat the subject as described herein. In certain example embodiments, the subject may be stratified into one or more groups, such as a low amyloid load, medium amyloid load, or high amyloid load, and then treated accordingly. To monitor treatment progress, the subject may be re-administered the antibody-peptide fusion proteins, and hence reassessed for their amyloid load.

IV. METHODS OF TREATMENT

Also provided herein are methods of treating a subject having an amyloid related disorder, comprising administering to the subject an effective amount of an antibody-peptide fusion protein of the present disclosure.

In some embodiments, provided a method of treating an amyloid disease (e.g., an amyloidosis) comprising administering a therapeutically effective amount of any one of the antibody-peptide fusion proteins described herein to a subject in need thereof.

In other embodiments, the amyloidosis is a systemic amyloidosis. In some embodiments, the amyloidosis is a familial amyloidosis. In other embodiments, the amyloidosis is a sporadic amyloidosis. In some embodiments, the amyloidosis or amyloid-related disease is AA amyloidosis, AL amyloidosis, AH amyloidosis, Aβ amyloidosis, ATTR amyloidosis, hATTR amyloidosis, ALect2 amyloidosis, and IAPP amyloidosis of type II diabetes, Alzheimer's disease, Down's syndrome, hereditary cerebral hemorrhage with amyloidosis of the Dutch type, cerebral beta-amyloid angiopathy, spongiform encelohalopathy, thyroid tumors, Parkinson's disease, dementia with Lewis bodies, a tauopathy, Huntington's disease, senile systemic amyloidosis, familial hemodialysis, senile systemic aging, aging pituitary disorder, iatrogenic syndrome, spongiform encephalopathies, reactive chronic inflammation, thyroid tumors, myeloma or other forms of cancer. In some embodiments, the amyloid related disease is selected from the group consisting of AL, AH, A$2M, ATTR, transthyretin, AA, AApoAI, AApoAII, AApoAIV, AApoCII, AApoCII, AGel, ALys, ALEct2, AFib, ACys, ACal, AMed, AIAPP, APro, AIns, APrP, ASPC, AGal7, ACor, Aker, ALac, AOAPP, ASem1, AEnf, or Aβ amyloidosis. In some embodiments, treatment with the antibody-peptide fusion protein results in the clearance of amyloid. In some embodiments, the antibody-peptide fusion protein binds to amyloids associated with normal aging. In other embodiments, the antibody-peptide fusion protein is used in the diagnosis, treatment, or prognosis of an amyloidosis or amyloid-related disease in a subject.

In some embodiments, the amyloid related disease is localized amyloidosis.

In some embodiments, the antibody-peptide fusion protein is administered via an intradermal, subcutaneous, intramuscular, intracardiac, intravascular, intravenous, intra-ocular, intra-arterial, epidural, intraspinal, extracorporeal, intrathecal, intraperitoneal, intrapleural, intraluminal, intravitreal, intracavernous, intraventricular, intra-bone, intraarticular, intracellular, or pulmonary route.

In some embodiments, the antibody-peptide fusion protein is administered in sufficient amounts to induce phagocytosis of the amyloid by cells of the immune system (e.g., macrophages).

In some embodiments, the subject is a mammal such as primate, bovine, rodent, or pig. In some embodiments, the subject is a human.

Also provided herein are methods of targeting an amyloid deposit for clearance. In some embodiments, the method comprises contacting an amyloid deposit with an antibody-peptide fusion protein of the present disclosure.

In some embodiments, the amyloid deposits may contribute to the pathology of a disease. In other embodiments, the amyloid deposits may be indicative of amyloidosis or an amyloid-related disease in a subject. In some embodiments, the antibody-peptide fusion protein binds to amyloids in a subject with an amyloidosis. In some embodiments, the amyloidosis is localized to a specific tissue or organ system, such as the liver, the heart, or the central nervous system.

In some embodiments, the amyloid deposit is removed. In some embodiments, the amyloid deposit is cleared. In some embodiments, the amyloid deposit is opsonized by the antibody-peptide fusion protein. In some embodiments, binding of the antibody-peptide fusion protein to human amyloid fibrils promotes the phagocytosis of the human amyloid fibrils and the removal of the amyloid deposit. In some embodiments, the antibody-peptide fusion protein opsonizes human amyloid fibrils, thereby removing of the amyloid deposit. In some embodiments, the antibody-peptide fusion protein opsonizes rVX6Wil fibrils. In some embodiments, binding of the antibody-peptide fusion protein to human amyloid fibrils promotes the phagocytosis and/or opsonization of human amyloid fibrils to an equal or greater extent than a control antibody (e.g., mIgp5 and/or c11-1F4).

In some embodiments, provided herein is a method of treating an amyloid-related disorder comprising a administering an antibody-peptide fusion protein conjugated to a detectable label, detecting the label, and administering to the subject an amyloidosis treatment if the signal is detected. In some embodiments, the detectable label is a radio label. In some embodiments the detectable label is an $I^{125}$, $Tc^{99}$ label. In some embodiments, the detectable label is a fluorescent label. In some embodiments the detectable label is an enzymatic label. In some embodiments, the label is horseradish peroxidase or alkaline phosphatase. Labels further include chemical moieties such as biotin, which may be detected via binding to a specific cognate detectable moiety, e.g., labeled avidin. In some embodiments, the amyloid deposit is identified in the liver, spleen, or blood of the subject. In some embodiments, the amyloidosis treatment comprises an antibody-peptide fusion protein provided herein.

Also provided herein is a method of identifying an amyloid deposit in a subject comprising administering an antibody-peptide fusion protein, wherein the antibody-peptide fusion protein is conjugated to a detectable label. In some embodiments, the method comprises detecting a signal from the antibody-peptide fusion protein. In some embodiments, the detectable label is a radio label. In some embodiments the detectable label is an $I^{125}$, $Tc^{99}$ label. In some embodiments, the detectable label is a fluorescent label. In some embodiments the detectable label is an enzymatic label. In some embodiments, the label is horseradish peroxidase or alkaline phosphatase. Labels further include chemical moieties such as biotin, which may be detected via binding to a specific cognate detectable moiety, e.g., labeled avidin. In some embodiments, the amyloid deposit is identified in the liver, spleen, or blood of the subject.

In some embodiments, provided herein is a method of detecting a ligand comprising contacting the ligand with an antibody-peptide fusion conjugated to a detectable label, and determining a signal from the detectable label. In some embodiments, the detectable label is a radio label. In some embodiments the detectable label is an $I^{125}$, $Tc^{99}$ label. In some embodiments, the detectable label is a fluorescent label. In some embodiments the detectable label is an enzymatic label. In some embodiments, the label is horseradish peroxidase or alkaline phosphatase. Labels further include chemical moieties such as biotin, which may be detected via binding to a specific cognate detectable moiety, e.g., labeled avidin. In some embodiments, the detection is in vitro. In some embodiments, the detection is in vivo.

V. NUCLEIC ACIDS, VECTORS, HOST CELLS, AND METHODS OF MAKING PEPTIDE-ANTIBODY FUSION PROTEINS

Also provided herein are nucleic acid(s) encoding an antibody-peptide fusion protein of the present disclosure. The antibody-peptide fusion protein may be any of the antibody-peptide fusion proteins described herein.

In some embodiments, the nucleic acid provided herein are in one or more vectors. For example, in some embodiments, provided herein is a vector comprising a heavy chain and light chain of an antibody, wherein the light chain is linked to a peptide. In some embodiments, the heavy chain and the light chain linked to a peptide are in different vectors.

In some embodiments, the vector comprises the nucleic acid(s) encoding an antibody-peptide fusion protein of the present disclosure.

For antibody production, the heavy chain and light chain linked to a peptide expression vectors may be introduced into appropriate production cell lines know in the art. Introduction of the expression vectors may be accomplished by co-transfection via electroporation or any other suitable transformation technology available in the art. Antibody producing cell lines can then be selected and expanded and antibodies purified. The purified antibodies can then be analyzed by standard techniques such as SDS-PAGE.

Also provided is a host cell comprising a nucleic acid encoding any of the antibody-peptide fusion proteins described herein. Suitable host cells for cloning or expression of antibody-encoding vectors include prokaryotic or eukaryotic cells described herein. For example, the antibody-peptide fusion protein may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N J, 2003), pp. 245-254, describing expression of antibody fragments in *E. coli*.) After expression, the antibody linked to a peptide may be isolated from the bacterial cell paste in a soluble fraction and can be further purified.

In some embodiments, the host cell comprising a vector comprising a nucleic acid(s) encoding an antibody-peptide fusion protein of the present disclosure.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse Sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

VI. PURIFICATION METHODS

Also provided herein are methods of producing an antibody-peptide fusion protein of the present disclosure. In some embodiments, the method comprises culturing a host cell of the present disclosure under conditions suitable for expression of the vector encoding the antibody-peptide fusion protein and recovering the antibody-peptide fusion protein.

In some embodiments, the method of producing an antibody-peptide fusion protein comprises i) culturing a host cell comprising a vector encoding an antibody-peptide fusion protein under perfusion cell culture conditions suitable for expression of the antibody-peptide fusion protein; and ii) recovering the antibody-peptide fusion protein about every 12-36 hours. In some embodiments, the antibody-peptide fusion protein comprises an amyloid-reactive peptide and an antibody that binds to human amyloid fibrils, wherein the antibody comprises a heavy chain comprising a heavy chain variable region (VH) and a light chain comprising a light chain variable region (VL). In some embodiments, the amyloid-reactive peptide and antibody are linked at the N-terminal end or the C-terminal end of the light chain, wherein the amyloid-reactive peptide is linked to the antibody via a spacer, or without a spacer. In some embodiments, the amyloid-reactive peptide and antibody are linked at the N-terminal end or the C-terminal end of the heavy chain, wherein the amyloid-reactive peptide is linked to the antibody via a spacer, or without a spacer. In some embodiments, the amyloid-reactive peptide and antibody are linked at the C-terminal end of the light chain, wherein the amyloid-reactive peptide is linked to the antibody via a spacer, or without a spacer. In some embodiments, the antibody is a full length antibody.

In some embodiments, the method comprises culturing a host cell using a fed-batch culture method. Fed batch culture refers to a method of culturing cells, wherein the cell culture is supplemented with fresh medium, i.e., the cells are "fed" with new medium while spent medium is not removed. Typically, a "fed-batch" culture process is performed in a bioreactor and additional components (e.g., nutritional supplements) are added to the culture at some time after initiation of the culture process. The controlled addition of nutrients directly affects the growth rate of the culture and allows for avoidance of the buildup of overflow metabolites (see, for example, Wlaschin, K. F. et al., "Fedbatch culture and dynamic nutrient feeding," Cell Culture Engineering, 101:43-74 (2006) and Lee, J. et al., "Control of fed-batch fermentations," Biotechnol. Adv., 17:29-48 (1999)). A fed-batch culture is typically terminated at some point and the cells and/or components in the medium are harvested and optionally purified.

In some embodiments, the method comprises culturing a host cell using a perfusion culture method. Perfusion refers to a method of culturing cells, wherein additional fresh medium is provided to the culture and spent medium is removed from the culture. Perfusion is initiated after the culture is seeded and can occur either continuously or intermittently, as desired, over a period of time. The fresh medium added during perfusion typically provides nutritional supplements for the cells that have been depleted during the culturing process. Perfusion also allows for removal of cellular waste products and toxic byproducts from the cell culture. Perfusion is performed during the growth phase of the cells, but can also be continued after the cells have been transferred to a fed-batch cell culture.

In some embodiments, the method of producing an antibody-peptide fusion protein comprises culturing a host cell comprising a vector encoding an antibody-peptide fusion protein under perfusion cell culture conditions suitable for expression of the antibody-peptide fusion protein. In some embodiments, the method comprises using a fed-batch culture method for the production of the antibody-peptide fusion protein. In some embodiments, the method comprises using a perfusion culture method for the production of the antibody-peptide fusion protein. In some embodiments, the antibody-peptide fusion protein comprises an amyloid-reactive peptide and an antibody that binds to a human amyloid fibrils, wherein the antibody comprises a heavy chain comprising a heavy chain variable region (VH) and a light chain comprising a light chain variable region (VL). In some embodiments, the amyloid-reactive peptide and antibody are linked at the N-terminal end or the C-terminal end of the light chain, wherein the amyloid-reactive peptide is linked to the antibody via a spacer, or without a spacer. In some embodiments, the amyloid-reactive peptide and antibody are linked at the N-terminal end or the C-terminal end of the heavy chain, wherein the amyloid-reactive peptide is linked to the antibody via a spacer, or without a spacer. In some embodiments, the amyloid-reactive peptide and antibody are linked at the C-terminal end of the light chain, wherein the amyloid-reactive peptide is linked to the antibody via a spacer, or without a spacer. In some embodiments, the antibody is a full length antibody.

In some embodiments, the method of producing an antibody-peptide fusion protein further comprises a continuous cell culture method. In some embodiments, the method comprises culturing cells under perfusion conditions. In some embodiments, the method comprises recovering the antibody-peptide fusion protein about every 12-36 hours. In some embodiments, the antibody-peptide fusion protein is recovered about every 12-24 hours, wherein the antibody-peptide fusion protein is recovered about every 12, 13, 14, 15, 16, 17, 18, 19, 20, 21, 22, 23, or 24 hours. In some embodiments, the antibody-peptide fusion protein is recovered about every 24-36 hours, wherein the antibody-peptide fusion protein is recovered about every 24, 25, 26, 27, 28, 29, 30, 31, 32, 33, 34, 35, or 36 hours. In some embodiments, the antibody-peptide fusion protein is recovered about every 12 to 16 hours, 14 to 18 hours, 16 to 20 hours, 16 to 24 hours, 20 to 32 hours, 18 to 36 hours, 24 to 32 hours, or 16 to 28 hours. In some embodiments, the antibody-peptide fusion protein is recovered after no more than 12, 16, 20, 24, 28, 32, or 36 hours. In some embodiments, the antibody-peptide fusion protein is recovered about every day. In some embodiments, the antibody-peptide fusion protein is recovered about every 1, 2, 3, 4, 5, 6, or 7 days. In some embodiments, the antibody-peptide fusion protein is recovered about every 1-4 days, 2-5 days, 3-6 days, 1-5 days, 3-7 days, or 1-7 days. In some embodiments, the antibody-peptide fusion protein is recovered after no more than 1, 2, 3, 4, 5, 6, or 7 days. In some embodiments, the antibody-peptide fusion protein comprises an amyloid-reactive peptide and an antibody that binds to human amyloid fibrils, wherein the antibody comprises a heavy chain comprising a heavy chain variable region (VH) and a light chain comprising a light chain variable region (VL). In some embodiments, the amyloid-reactive peptide and antibody are linked at the N-terminal end or the C-terminal end of the light chain, wherein the amyloid-reactive peptide is linked to the antibody via a spacer, or without a spacer. In some embodiments, the amyloid-reactive peptide and antibody are linked at the N-terminal end or the C-terminal end of the heavy chain, wherein the amyloid-reactive peptide is linked to the antibody via a spacer, or without a spacer. In some embodiments, the amyloid-reactive peptide and antibody are linked at the C-terminal end of the light chain, wherein the amyloid-reactive peptide is linked to the antibody via a spacer, or without a spacer. In some embodiments, the antibody is a full length antibody.

In some embodiments, the method of producing an antibody-peptide fusion protein further comprises applying the antibody-peptide fusion recovered in the recovering step to a cation exchange chromatography column. In some embodiments, the cation exchange chromatography column is used to isolate intact antibody-peptide fusion protein. In some embodiments, the cation exchange chromatography column is used to separate truncated antibody-peptide fusion protein away from the intact antibody-peptide fusion protein. In some embodiments, the recovered antibody-peptide fusion is applied to the cation exchange chromatography column. In some embodiments, the cation exchange chromatography column is washed with one or more buffers comprising a dissolved salt. In some embodiments, the cation exchange chromatography column is washed with a low-salt buffer. In some embodiments, the cation exchange chromatography column is washed with a high-salt buffer. In some embodiments, the cation exchange chromatography column is first washed with a low-salt buffer, followed by application of a high-salt buffer elution buffer. In some embodiments, the low-salt buffer elutes the truncated antibody-peptide fusion protein from the cation exchange chromatography column. In some embodiments, the high-salt buffer elutes the intact antibody-peptide fusion protein from the cation exchange chromatography column. In some embodiments, the method comprises applying the antibody-peptide fusion protein to the cation exchange chromatography column, then washing the column with a first buffer containing low-salt concentrations, then eluting the intact antibody-peptide fusion protein with a second buffer containing high-salt concentrations. In some embodiments, the intact antibody-peptide fusion protein is eluted separately from a truncated antibody-peptide fusion protein. In some embodiments, the method results in enrichment of the intact antibody-peptide fusion protein. In some embodiments, the method results in removal of the truncated antibody-peptide fusion protein from the isolated intact antibody-peptide fusion protein. In some embodiments, the method comprises applying the antibody-peptide fusion protein to the cation exchange chromatography column, then washing the column with a first buffer containing low-salt concentrations, then applying a second buffer containing high-salt concentrations results in the isolation of an intact antibody-peptide fusion protein.

In some embodiments, the method comprises applying the antibody-peptide fusion protein to the cation exchange chromatography column, then washing the column with a first buffer containing low-salt concentrations, then washing with a second buffer containing high-salt concentrations results in the isolation of an intact antibody-peptide fusion protein. In some embodiments, washing the column with a first buffer containing low-salt concentrations elutes the truncated antibody-peptide fusion protein from the cation exchange chromatography column. In some embodiments, the first buffer comprising a low-salt concentration comprises a concentration of salt no higher than 200 mM, 210 mM, 220 mM, 230 mM, 240 mM, 250 mM, 260 mM, 270 mM, 280 mM, 290 mM, or 300 mM. In some embodiments, the first buffer comprising a low-salt concentration comprises a concentration of salt between 200 mM and 300 mM, 210 mM and 280 mM, 220 mM and 260 mM, 210 mM and 290 mM, 240 mM and 270 mM, or 230 mM and 260 mM. In some embodiments, the first buffer comprising a low-salt concentration comprises a concentration of salt that is about 220 mM, 240 mM, 260 mM, or 280 mM or any range between these values. In some embodiments, the first buffer comprises a concentration of salt from about 200 mM to about 300 mM, or about 220 mM to about 280 mM. In some embodiments, the first buffer comprising a low-salt concentration comprises a concentration of salt that is about 260 mM. In some embodiments, washing the column with a second buffer containing high-salt concentrations after washing the column with the first buffer continuing low-salt concentration elutes the intact antibody-peptide fusion protein from the cation exchange chromatography column. In some embodiments, the second buffer comprising a high-salt concentration comprises a concentration of salt no less than 350 mM, 360 mM, 370 mM, 380 mM, 390 mM, 400 mM, 410 mM, 420 mM, 430 mM, 440 mM, or 450 mM. In some embodiments, the second buffer comprising a high-salt concentration comprises a concentration of salt between 350 mM and 450 mM, 360 mM and 430 mM, 370 mM and 410 mM, 360 mM and 440 mM, 390 mM and 420 mM, or 380 mM and 410 mM or any range between these points. In some embodiments, the second buffer comprises a concentration of salt of between 350 mM and 450 mM or between 380 mM and 420 mM. In some embodiments, the first buffer comprising a low-salt concentration comprises a concentration of salt that is about 380 mM, 400 mM, 420 mM, or 440 mM. In some embodiments, the first buffer comprising a low-salt concentration comprises a concentration of salt that is about 400 mM. In some embodiments, the pH of the first and second buffers are between 4.5 and 6.5, 4.7 and 6.3, 5.1 and 5.7, 4.7 and 6.1, 5.5 and 5.9, or 5.3 and 5.7. In some embodiments, the pH of the first and second buffers are about 5.0, 5.1, 5.2, 5.3, 5.4, 5.5, 5.6, 5.7, 5.8, 5.9, or 6.0. In some embodiments, the pH of the first and second buffers are about 5.5. In some embodiments, the pH of the first and second buffers are the same. In some embodiments, the pH of the first and second buffers are the different.

In some embodiments, the method of producing comprises applying the antibody-peptide fusion protein to the cation exchange chromatography column, then washing the column with a first buffer containing low-salt concentrations, then eluting with a second buffer containing high-salt concentrations results in the isolation of an intact antibody-peptide fusion protein. In some embodiment, the method comprises applying the antibody-peptide fusion protein to the cation exchange chromatography column with a loading density, wherein the loading density is defined as grams antibody-peptide fusion protein per liter of resin (g/L). In some embodiments, the loading density is no more than 20, 25, 30, 35, 40, 45, 50, or 55 g/L, any range between these points. In some embodiments, the loading density is at least 15, 20, 25, 30, 35, 40, 45, or 50 g/L. In some embodiments, the loading density is between 15 and 55, 20 and 45, 25 and 50, 20 and 35, 30 and 40, 35 and 50, or 20 and 50 g/L. In some embodiments, the loading density is 50 g/L.

In some embodiments, the method of producing an antibody-peptide fusion protein comprises culturing a host cell, wherein the host cell is a mammalian cell. In some embodiments, the host cell is a CHO cell. In some embodiments, the host cell comprises a vector encoding an antibody-peptide fusion protein, including any of the antibody-peptide fusion proteins described herein.

In some embodiments, the method of producing an antibody-peptide fusion protein further comprises determining the purity of the antibody-peptide fusion protein. For example, sodium dodecyl sulfate capillary electrophoresis (CE-SDS) is an analytical method used to assess the purity of proteins, including the quantitative analysis of monoclonal antibodies. Antibody samples are mixed with a replaceable SDS-gel buffer and then electrophoresed through an SDS-gel filled capillary. Samples are injected into the capillary inlets capillary using high voltage. Protein migration through the separation matrix occurs in an anodic direction, and quantitative detection occurs near the distal end of the capillary using a UV absorbance detection system. In some embodiments, the purity of the antibody-peptide fusion protein is determined using one or more analytical methods comprising sodium dodecyl sulfate capillary electrophoresis (CE-SDS), liquid chromatography (LC), mass spectrometry (MS), or a combination thereof. In some embodiments, the purity of the antibody-peptide fusion protein is determined using sodium dodecyl sulfate capillary electrophoresis (CE-SDS).

In some embodiments, the method further comprises determining the purity, wherein the antibody-peptide fusion protein is purified to at least 80% intact antibody-peptide fusion protein. In some embodiments, the antibody-peptide fusion protein has a purity that is defined by the amount of the intact antibody-peptide fusion protein present. In some embodiments, the intact antibody-peptide fusion protein consists of the full length antibody-peptide fusion. In some embodiments, the antibody-peptide fusion protein has a purity of at least 80%. In some embodiments, the antibody-peptide fusion protein has a purity of at least 80%, 85%, 90%, 91%, 92%, 93%, 94%, 95%, 96%, 97%, 98%, 99%, or 99.5%. In some embodiments, the antibody-peptide fusion protein has a purity between 80% and 100%, 82% and 96%, 85% and 90%, 84% and 92%, 80% and 88%, 90% and 98%, or 95% and 100%. In some embodiments, the antibody-peptide fusion protein purity is positively correlated to amyloid substrate binding.

In some embodiments, the method further comprises determining the purity, wherein the antibody-peptide fusion protein is purified to at least 80% intact antibody-peptide fusion protein. In some embodiments, the antibody-peptide fusion protein has a purity that is defined by the amount of the intact antibody-peptide fusion protein present. In some embodiments, the intact antibody-peptide fusion protein consists of the full length antibody-peptide fusion. In some embodiments, the antibody-peptide fusion protein comprises no more than 20% of a cleavage product. In some embodiments, the cleavage product comprises a light chain comprising a light chain lacking one or more amino acid residues from the N-terminus or the C-terminus. In some embodiments, the cleavage product comprises a heavy chain comprising a heavy chain lacking one or more amino acid residues from the N-terminus or the C-terminus. In some embodiments, the antibody-peptide fusion protein comprises no more than 20%, 15%, 12%, 10%, 9%, 8%, 7%, 6%, 5%, 4%, 3%, 2%, 1%, or 0.5% of the cleavage product. In some embodiments, the antibody-peptide fusion protein comprises between 20% and 0%, 15% and 2%, 12% and 4%, 15% and 8%, 10% and 1%, 5% and 2%, or 2% and 0% cleavage product.

VII. KITS

The present disclosure also provides kits containing an antibody-peptide fusion protein of the present disclosure. Kits of the present disclosure may include one or more containers comprising a purified antibody-peptide fusion protein. In some embodiments, the kits further include instructions for use in accordance with the methods of this disclosure. In some embodiments, these instructions comprise a description of administration of the antibody-peptide fusion protein as described herein to treat an amyloid disease, according to any methods of this disclosure.

In some embodiments, the instructions comprise a description of how to detect an amyloid deposit, for example in a subject, in a tissue sample, or in a cell. The kit may further comprise a description of selecting an individual suitable for treatment based on identifying whether that individual has an amyloid disease, as described herein.

The label or package insert indicates that the composition is used for treating, e.g., a disease of the present disclosure. Instructions may be provided for practicing any of the methods described herein.

VIII. EXAMPLES

The following examples further illustrate the invention but should not be construed as in any way limiting its scope. In light of the present disclosure and the general level of skill in the art, those of skill will appreciate that the following Examples are intended to be exemplary only and that numerous changes, modifications, and alterations can be employed without departing from the scope of the presently disclosed subject matter. The attached figures are meant to be considered as integral parts of the specification and description of the disclosure.

Example 1. Design of Antibody-Peptide Fusion Proteins

The following example describes the design of exemplary amyloid-reactive peptide-antibody fusion protein constructs. The structures of exemplary constructs are provided in FIGS. 1-4. Amino acids sequences of the constructs are provided in Table E1 and Table E2, below. In Tables E1-E2, the amino acid sequence of the amyloid-reactive peptide p5R shown in bold, and spacer sequences are underlined and italicized.

TABLE E1

| Antibody-peptide fusion protein light chain sequences | | | |
|---|---|---|---|
| Description | Amino Acid Sequence | SEQ ID NO | Figure with exemplary structure |
| VH9-D54E/VL4-N33S. p5R fused to N-terminus of light chain via short rigid spacer (VSPSV). | APGGGRAQRAQARQARQAQRAQRAQARQ ARQ_VSPSV_DVVMTQSPLSLPVTLGQPAS ISCRSSQSLVHRSGNTYLHWFQQRPGQS PRLLIYKVSNRFSGVPDRESGSGSGTDE TLKISRVEAEDVGVYFCFQTTYVPNTFG GGTKLEIKRTVAAPSVFIFPPSDEQLKS GTASVVCLLNNFYPREAKVQWKVDNALQ SGNSQESVTEQDSKDSTYSLSSTLTLSK ADYEKHKVYACEVTHQGLSSPVTKSENR GEC | 87 | FIG. 1 |
| VH9-D54E/VL4-N33S. p5R fused to C-terminus of heavy chain via short rigid spacer (VSPSV). | DVVMTQSPLSLPVTLGQPASISCRSSQS LVHRSGNTYLHWFQQRPGQSPRLLIYKV SNRFSGVPDRFSGSGSGTDFTLKISRVE AEDVGVYFCFQTTYVPNTFGGGTKLEIK RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSENRGEC | 88 | FIG. 2 |

TABLE E1-continued

Antibody-peptide fusion protein light chain sequences

| Description | Amino Acid Sequence | SEQ ID NO | Figure with exemplary structure |
|---|---|---|---|
| VH9-D54E/VL4-N33S. p5R fused to C-terminus of light chain via short rigid spacer (VSPSV). | DVVMTQSPLSLPVTLGQPASISCRSSQS LVHRSGNTYLHWFQQRPGQSPRLLIYKV SNRFSGVPDRFSGSGSGTDFTLKISRVE AEDVGVYFCFQTTYVPNTFGGGTKLEIK RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSENRGEC*VSPSV* RAQRAQARQARQAQRAQRAQARQARQ | 89 | FIG. 3 |
| VH9-D54E/VL4-N33S. p5R fused to C-terminus of light chain via long spacer (GGGGSGGGGS). | DVVMTQSPLSLPVTLGQPASISCRSSQS LVHRSGNTYLHWFQQRPGQSPRLLIYKV SNRFSGVPDRFSGSGSGTDFTLKISRVE AEDVGVYFCFQTTYVPNTFGGGTKLEIK RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSENRGEC*GGGGS GGGGS*RAQRAQARQARQAQRAQRAQRQ ARQ | 90 | FIG. 4 |

TABLE E2

Antibody-peptide fusion protein heavy chain sequences

| Description | Amino Acid Sequence | SEQ ID NO | Figure with exemplary structure |
|---|---|---|---|
| VH9-D54E/VL4-N33S. p5R fused to N-terminus of light chain via short rigid spacer (VSPSV). | QVQLQESGPGLVKPSETLSLTCTVSGFS LSSYGVSWIRQPPGKGLEWLGVIWGEGS TNYHPNLMSRVTISVDTSKSQVLFKLSS VTAADTAVYYCATLDYWGQGTSVTVSSA STKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKKVEPKSCDKTHTCPPCP APELLGGPSVFLFPPKPKDTLMISRTPE VTCVVVDVSHEDPEVKENWYVDGVEVHN AKTKPREEQYNSTYRVVSVLTVLHQDWL NGKEYKCKVSNKALPAPIEKTISKAKGQ PREPQVYTLPPSRDELTKNQVSLTCLVK GFYPSDIAVEWESNGQPENNYKTTPPVL DSDGSFFLYSKLTVDKSRWQQGNVFSCS VMHEALHNHYTQKSLSLSPGK | 91 | FIG. 1 |
| VH9-D54E/VL4-N33S. p5R fused to C-terminus of heavy chain via short rigid spacer (VSPSV). | QVQLQESGPGLVKPSETLSLTCTVSGES LSSYGVSWIRQPPGKGLEWLGVIWGEGS TNYHPNLMSRVTISVDTSKSQVLEKLSS VTAADTAVYYCATLDYWGQGTSVTVSSA STKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKKVEPKSCDKTHTCPPCP APELLGGPSVFLFPPKPKDTLMISRTPE VTCVVVDVSHEDPEVKENWYVDGVEVHN AKTKPREEQYNSTYRVVSVLTVLHQDWL NGKEYKCKVSNKALPAPIEKTISKAKGQ PREPQVYTLPPSRDELTKNQVSLTCLVK GFYPSDIAVEWESNGQPENNYKTTPPVL DSDGSFFLYSKLTVDKSRWQQGNVFSCS VMHEALHNHYTQKSLSLSPGK*VSPSV*RA QRAQARQARQAQRAQRAQARQARQ | 92 | FIG. 2 |
| VH9-D54E/VL4-N33S. p5R fused to C-terminus of light chain via short rigid spacer (VSPSV). | See amino acid sequence above. | 91 | FIG. 3 |

TABLE E2-continued

Antibody-peptide fusion protein heavy chain sequences

| Description | Amino Acid Sequence | SEQ ID NO | Figure with exemplary structure |
|---|---|---|---|
| VH9-D54E/VL4-N33S. p5R fused to C-terminus of light chain via long spacer (GGGGSGGGGS). | See amino acid sequence above. | 91 | FIG. 4 |

Example 2. Binding Affinities of Humanized Anti-Amyloid Antibodies to Len(1-22) Monomer Peptide Binding affinities of humanized anti-amyloid antibodies have been determined, for example, as described in International Application No. PCT/US2020/060596. Table E3, below, provides the results of surface plasmon resonance (SPR) assays measuring the binding of the humanized anti-amyloid antibodies to a Len(1-22) Monomer peptide. Specifically, the humanized VH9 and VL4 sequences were tested with or without additional amino acid substitutions, as indicated in the "Ligand" column of Table E3.

Figure 5A:
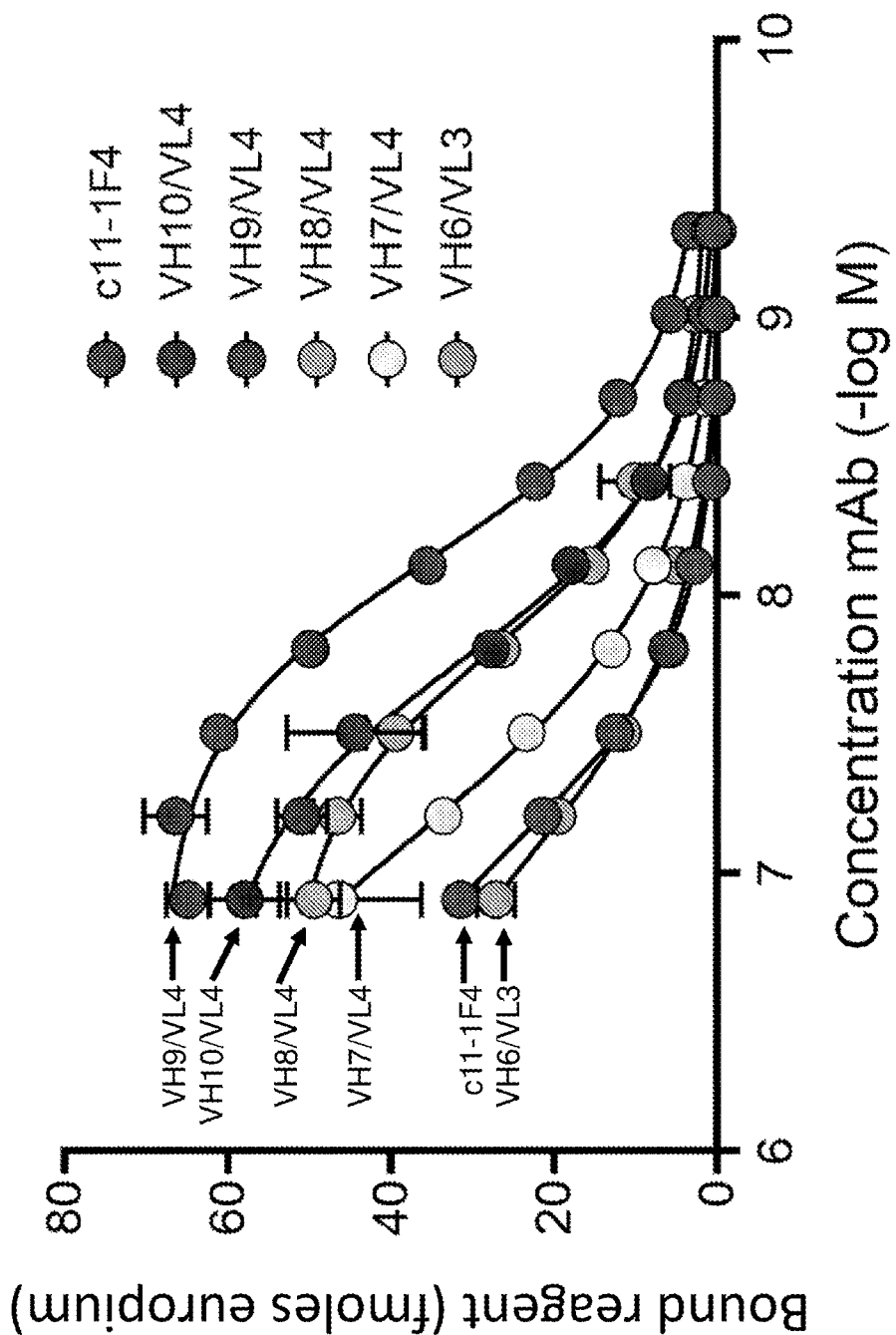
FIG. 5A shows data from a euripoium-linked immunosorbent assay (EuLISA) measuring binding of chimeric (c) 11-1F4, and humanized variants, VH10/VL4, VH9/VL4, VH8/VL4, VH7/VL4, or VH6/VL3 to synthetic rVX6Wil light chain amyloid-like fibrils.

Example 3. Binding Affinities of Humanized Anti-Amyloid Antibodies to rVλ6Wil Fibrils The ability of humanized anti-amyloid antibodies to bind rVλ6Wil fibrils has been tested, for example, by euripoium-linked immunosorbent assay (EuLISA), compared to the chimeric antibody c11-1F4 (FIG. 5A). Based on that data presented in FIG. 5A, c11-1F4 bound with an $EC_{50}$ value of ~72 nM, VH10/VL4 bound with an $EC_{50}$ value of 17 nM, VH9/VL4 bound with an $EC_{50}$ value of 7 nM, VH8/VL4 bound with an $EC_{50}$ value of 16 nM, V/H7/VL4 bound with an $EC_{50}$ value of 75 nM and VH6/VL3 bound with an $EC_{50}$ value of 95 nM. VH9/VL4 exhibited increased binding

TABLE E3

Exemplary SPR analysis of binding of humanized antibodies to Len(1-22) monomer peptide

| Ligand | Analyte | $Chi^2$ ($RU^2$) | $k_a$ (1/Ms) | $k_d$ (1/s) | $K_D$ (M) | $R_{max}$ (RU) |
|---|---|---|---|---|---|---|
| VH9 - D54S + VL4 | Len 1-22 Monomer peptide | 2.29E-02 | 2.30E+03 | 1.39E-04 | 6.05E-08 | 9.8 |
| VH9 - D54Q + VL4 | Len 1-22 Monomer peptide | 5.00E-03 | 3.90E+03 | 9.97E-04 | 2.56E-07 | 21.8 |
| VH9 - D54E + VL4 | Len 1-22 Monomer peptide | 1.04E-02 | 8.28E+03 | 1.35E-03 | 1.63E-07 | 26.8 |
| VH9 - D54A + VL4 | Len 1-22 Monomer peptide | 3.06E-02 | 3.56E+02 | 7.78E-04 | 2.18E-06 | 10.7 |
| VH9 - D54H + VL4 | Len 1-22 Monomer peptide | 1.97E-02 | 5.93E+03 | 1.39E-03 | 2.35E-07 | 15.1 |
| VH9 - G55A + VL4 | Len 1-22 Monomer peptide | 7.41E-02 | 2.82E+04 | 4.84E-04 | 1.72E-08 | 21.3 |
| VH9 - G55V + VL4 | Len 1-22 Monomer peptide | 8.29E-02 | 3.38E+03 | 1.63E-03 | 4.83E-07 | 9.8 |
| VH9 - M64V + VL4 | Len 1-22 Monomer peptide | 6.24E-02 | 2.38E+04 | 5.20E-04 | 2.18E-08 | 12.8 |
| VH9 - M64I + VL4 | Len 1-22 Monomer peptide | 1.07E-01 | 9.29E+04 | 1.92E-03 | 2.07E-08 | 6.5 |
| VH9 - M64L + VL4 | Len 1-22 Monomer peptide | 1.16E-01 | 9.30E+04 | 2.08E-03 | 2.24E-08 | 7.8 |
| VH9- M64A + VL4 | Len 1-22 Monomer peptide | 1.50E-01 | 7.79E+04 | 1.04E-03 | 1.33E-08 | 10.5 |
| VH9 + VL4 - N33S | Len 1-22 Monomer peptide | 1.10E-01 | 1.43E+04 | 9.54E-04 | 6.69E-08 | 23.8 |
| VH9 + VL4 - N33Q | Len 1-22 Monomer peptide | 6.49E-02 | 1.33E+04 | 1.04E-03 | 7.84E-08 | 21.7 |
| VH9 + VL4 - N33E | Len 1-22 Monomer peptide | 5.27E-02 | 1.23E+04 | 1.31E-03 | 1.06E-07 | 15.4 |
| VH9 + VL4 - N33A | Len 1-22 Monomer peptide | 5.56E-02 | 1.13E+04 | 1.00E-03 | 8.85E-08 | 17.4 |
| VH9 + VL4 - N33H | Len 1-22 Monomer peptide | 7.20E-02 | 1.31E+04 | 7.43E-04 | 5.66E-08 | 17.6 |
| VH9 + VL4 - G34A | Len 1-22 Monomer peptide | 9.04E-01 | 5.95E+04 | 1.81E-03 | 3.04E-08 | 24.9 |
| VH9 + VL4- G34V | Len 1-22 Monomer peptide | 5.83E-01 | 4.18E+04 | 1.46E-03 | 3.50E-08 | 29.7 |
| VH9 + VL4 | Len 1-22 Monomer peptide | 1.88E+00 | 6.04E+04 | 2.60E-03 | 4.30E-08 | 47.2 | relative to c11-1F4 (FIG. 5A). The VH9/VL4 antibody bound amyloid fibrils to a greater extent than VH6/VL3 did (FIG. 5A).

Figure 5B:
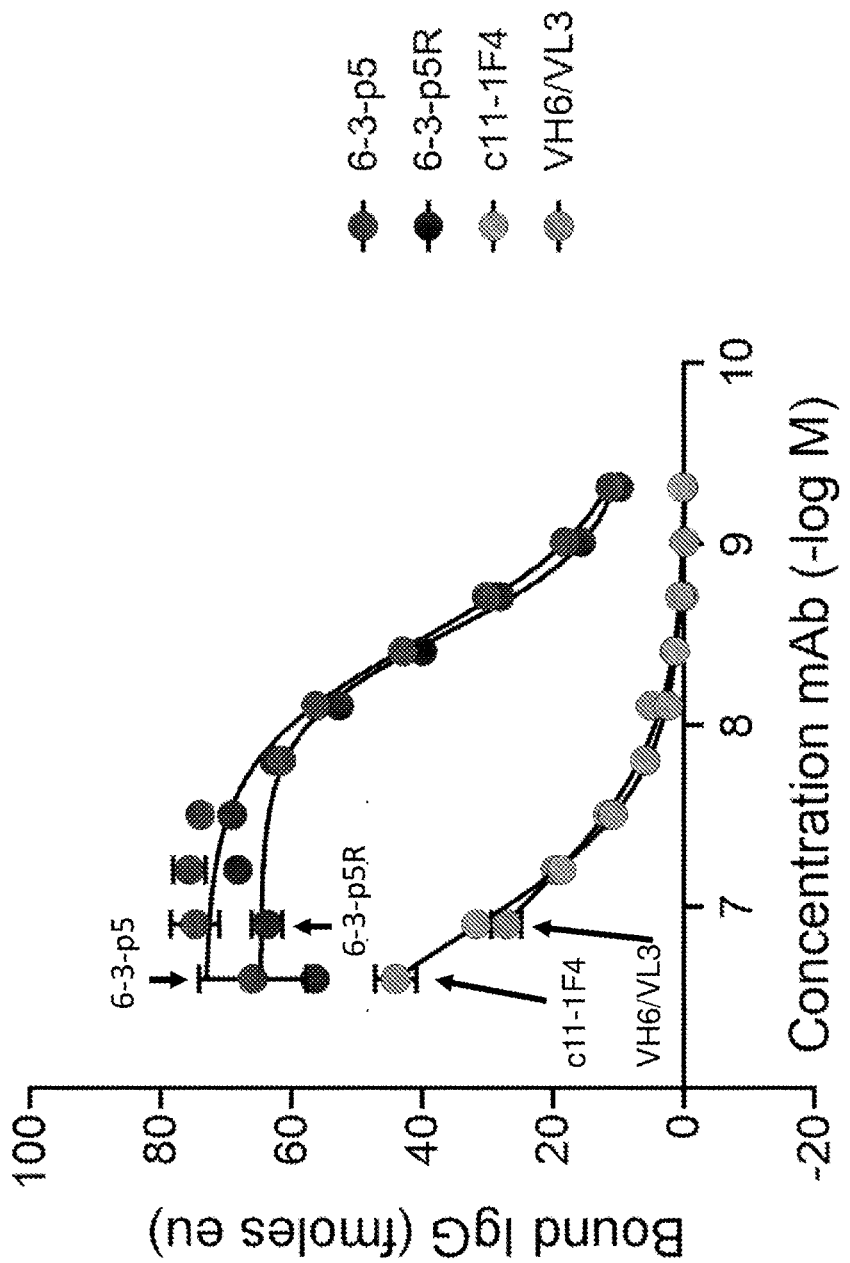
FIG. 5B shows data from an EuLISA measuring binding of VH6/VL3-p5 (6-3-p5), VH6/VL3-p5R (6-3-p5R), c11-1F4, or VH6/VL3 to rVλ6Wil fibrils.

As further described in PCT/US2020/060596, which is hereby incorporated by reference in its entirety, the peptides p5 and p5R were added to the N-terminal of the light chain of humanized antibodies with VH9/VL4 and VH6/VL3. As shown in FIG. 5B, addition of peptides p5 and p5R to the N-terminal of the light chain of VH6/VL3 enhanced the binding to rVλ6Wil fibrils by ~30-fold (based on $EC_{50}$). Based on that data presented in FIG. 5B, VH6/VL3-p5 bound with an $EC_{50}$ value of 3 nM, VH6/VL3-p5R bound with an $EC_{50}$ value of 3 nM, c11-1F4 bound with an $EC_{50}$ value of ~100 nM, and VH6/VL3 bound with an $EC_{50}$ value of 95 nM.

Figure 5C:
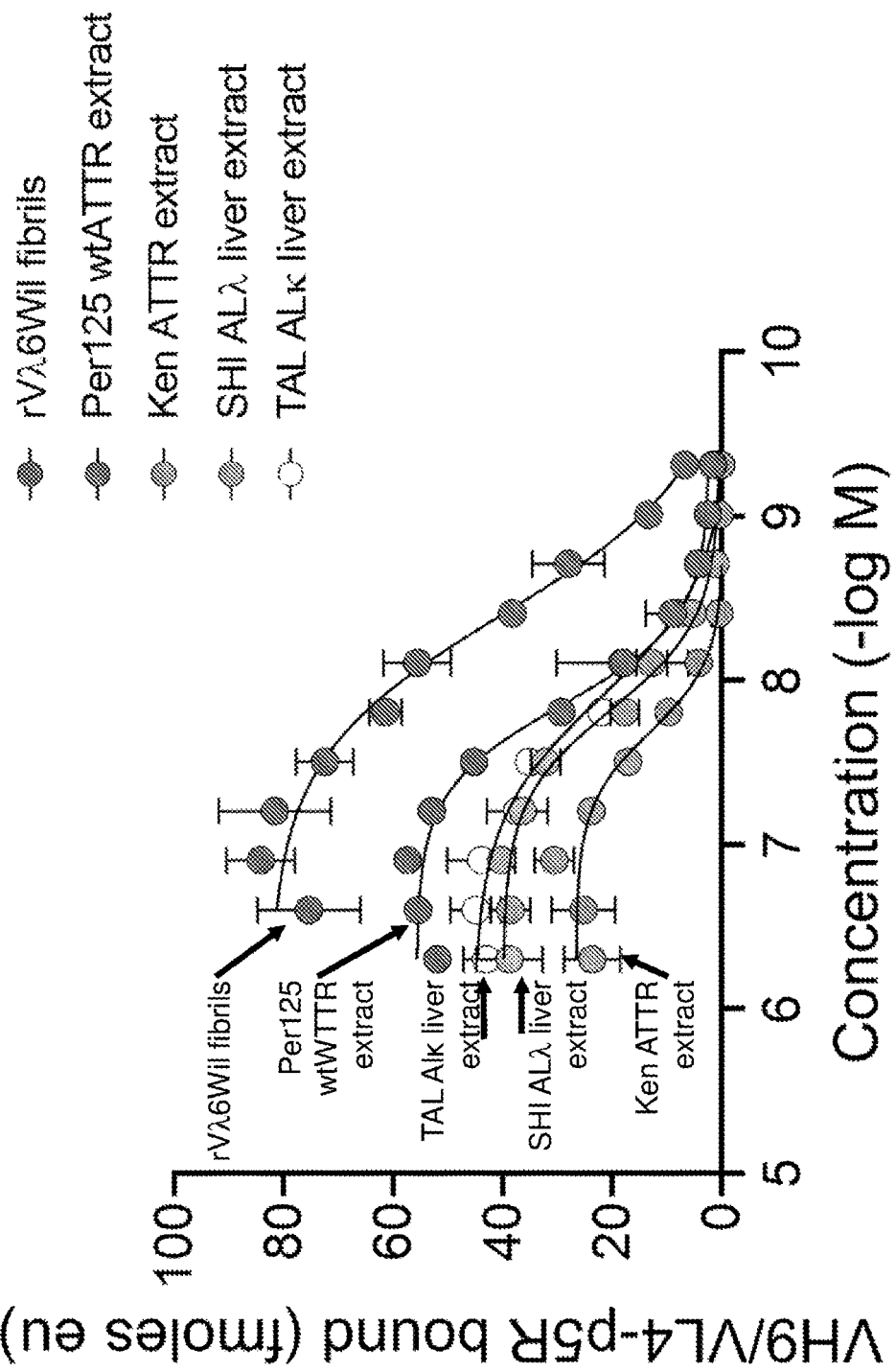
FIG. 5C shows data from an EuLISA measuring binding of VH9/VL/4-p5R to rVλ6Wil fibrils, Per125 wtATTR extract, Ken ATTR extract, SHI AU liver extract, or TAL ALκ liver extract.
Figure 5D:
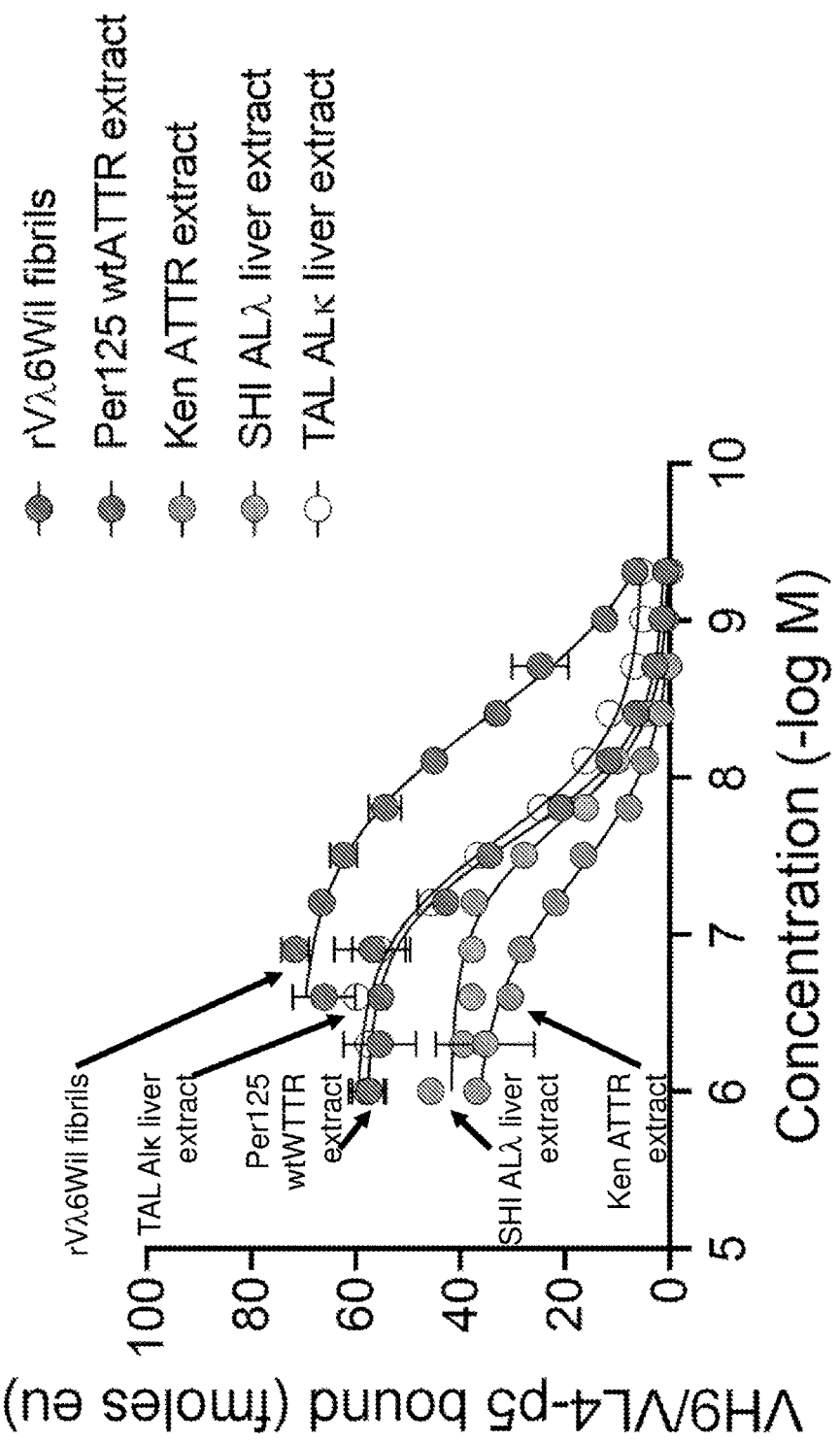
FIG. 5D shows data from an EuLISA measuring binding of VH9/VL/4-p5 to rVλ6Wil fibrils, Per125 wtATTR extract, Ken ATTR extract, SHI AL liver extract, or TAL ALκ liver extract.

In general, variants with the arginine variant of p5 (p5R) were superior to the p5 variants (FIG. 5C and FIG. 5D).

Figure 5E:
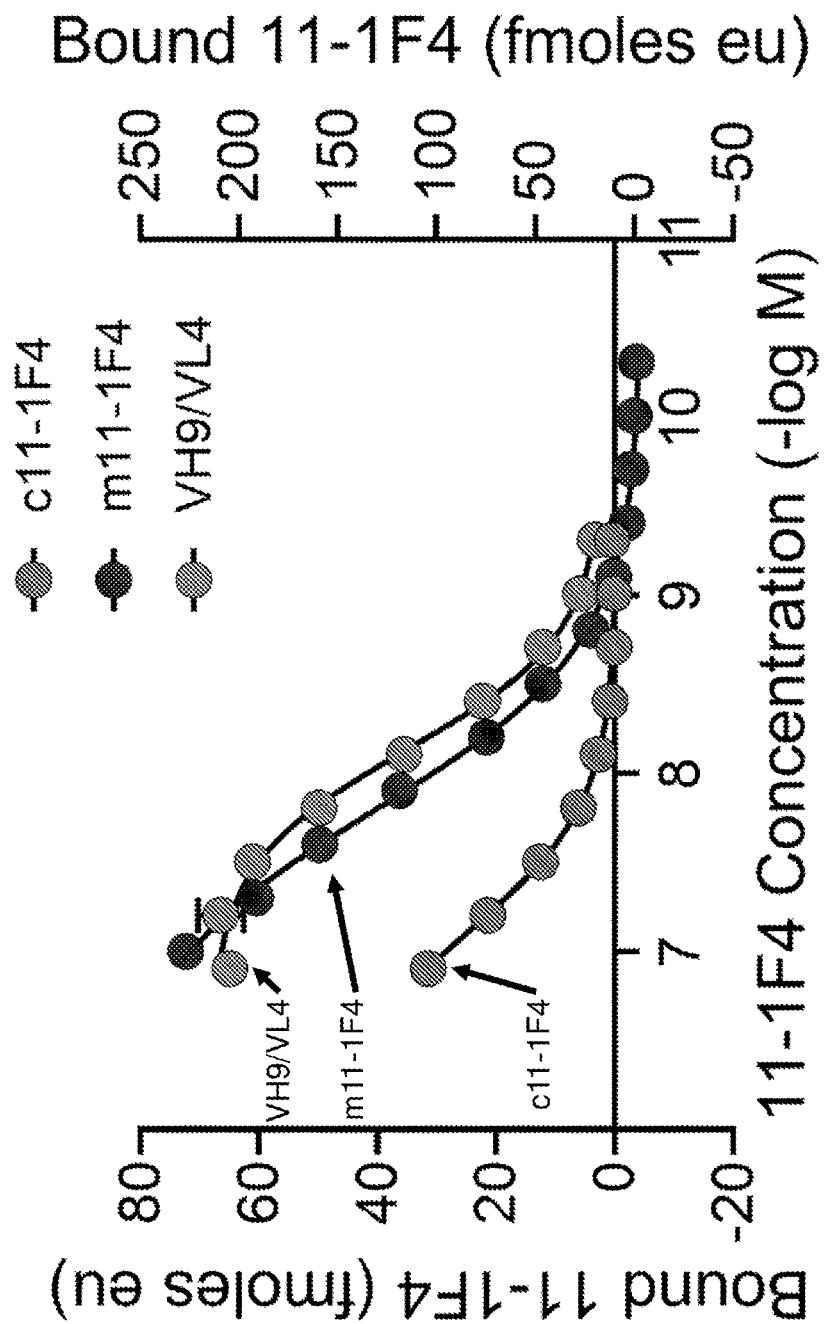
FIG. 5E shows data from an EuLISA measuring binding of c11-1F4, m11-1F4, or VH9/VL4 to rVλ6Wil fibrils.
Figure 5G:
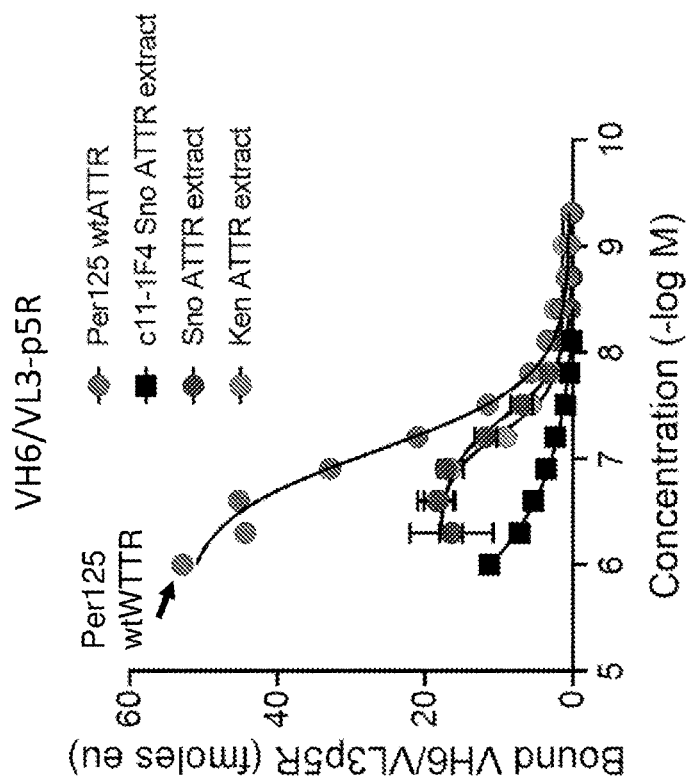
FIG. 5G shows data from an EuLISA measuring binding of VH6/VL3-p5R to Per125 wtATTR (gray circles, see label), Sno ATTR extract (dark gray circles), or Ken ATTR extract (light gray circles), and c11-1F4 binding to Sno ATTR extract (black squares). The log-transformed molar concentration of monoclonal antibody (–log(M)) is shown on the x-axis, and the level of binding (femtomoles europium) is shown on the y-axis.

As shown in FIG. 5E, VH9/VL4 had the same reactivity to rVλ6Wil fibrils as the murine parent.

Figure 5F:
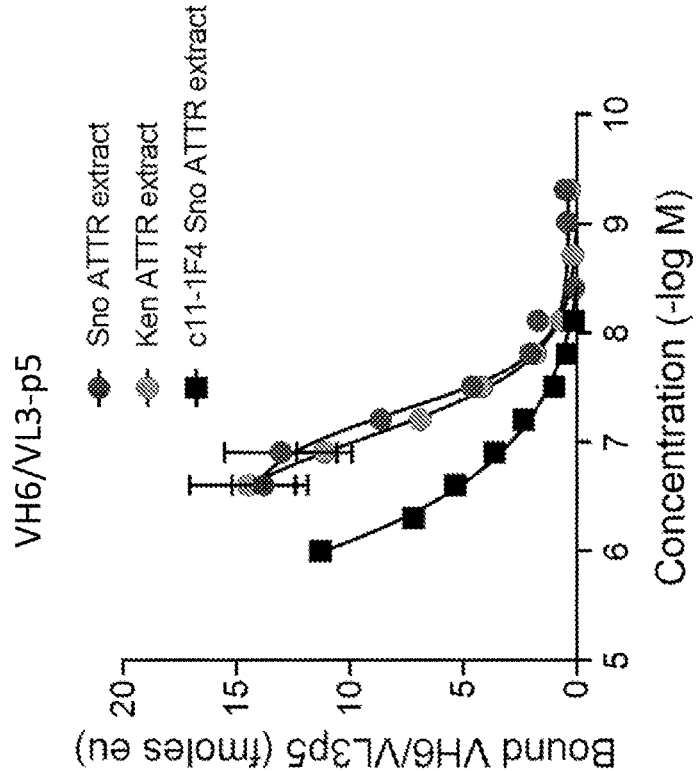
FIG. 5F shows data from an EuLISA measuring binding of VH6/VL3-p5 to Sno ATTR extract (dark gray circles) or Ken ATTR extract (light gray circles), and c11-1F4 binding to Sno ATTR extract (black squares).

As shown in FIG. 5E and FIG. 5F, both VH6/VL3-p5 and VH6/VL3-p5R exhibited binding to hATTR amyloid extracts. Based on the data in FIG. 5E and FIG. 5F, VH6/VL3-p5 bound to Sno hATTR extract with an $EC_{50}$ value of 50 nM, and to Ken ATTR extract with an $EC_{50}$ value of 90 nM, and VH6/VL3-p5R bound to Sno ATTR extract with an $EC_{50}$ value of 47 nM, Ken ATTR extract with an $EC_{50}$ value of 70 nM, and Per125 wtATTR with an $EC_{50}$ value of 85 nM.

Table E4, below, provides the results of the EuLISAs measuring the ability of mIgp5, hIgG1, c11-1F4, m11-1F4, VH6/VL3-p5, VH9/VL4-p5, and VH9/VL4-p5R to bind rVλ6Wil fibrils, Per125 wtATTR extract, KEN hATTR extract, SHI ALλ liver extract, and TAL ALκ liver extract. For each combination of antibody and substrate, the Log-transformed $EC_{50}$, $EC_{50}$, and maximal level of binding in the assay is shown. Conditions labeled "na" were not tested. As shown in Table E4, the humanized anti-amyloid antibodies fused to p5 or p5R were able to bind various amyloid fibrils and amyloid extracts. VH6/VL3-p5, VH9/VL4-p5, and VH9/VL4-p5R bound all fibrils and extracts tested with higher affinity (based on $EC_{50}$ measurements) than m11-1F4 and all other control antibodies. VH9/VL4-p5R generally exhibited lower $EC_{50}$s than VH9/VL4-p5 did, and VH9/VL4-p5 generally exhibited lower $EC_{50}$s than VH6/VL3-p5.

TABLE E4

Exemplary EuLISA data

| Substrate | LogEC$_{50}$ | EC$_{50}$ | Max |
|---|---|---|---|
| mIgp5 | | | |
| rVλ6Wil | 8.541 | 2.88E−09 | 58.5 |
| Per125 wtATTR | 8.205 | 6.24E−09 | 31.7 |
| KEN hATTR | 8.448 | 3.56E−09 | 19.9 |
| SHI ALλ liver | 8.532 | 2.94E−09 | 24.0 |
| TAL ALκ liver | 8.472 | 3.37E−09 | 24.6 |
| hIgG1 | | | |
| rVλ6Wil | 5.894 | 1.28E−06 | 39.3 |
| Per125 wtATTR | ~7.917 | na | ~8.378 |
| KEN hATTR | ~9.061 | na | −0.8 |
| SHI ALλ liver | ~7.878 | na | 2.5 |
| TAL ALκ liver | ~3.001 | na | ~2217 |
| c11-1F4 | | | |
| rVλ6Wil | 6.536 | 2.91E−07 | 63.9 |
| Per125 wtATTR | 6.419 | 3.81E−07 | 71.12 |

TABLE E4-continued

Exemplary EuLISA data

| Substrate | LogEC$_{50}$ | EC$_{50}$ | Max |
|---|---|---|---|
| KEN hATTR | ~−1.360 | na | ~19728 |
| SHI ALλ liver | 6.592 | 2.56E−07 | 51.31 |
| TAL ALκ liver | ~0.5994 | na | ~17788 |
| m11-1F4 | | | |
| rVλ6Wil | 6.265 | 5.43E−07 | 183.6 |
| Per125 wtATTR | 5.725 | 1.88E−06 | 208.8 |
| KEN hATTR | ~2.386 | na | ~294290 |
| SHI ALλ liver | ~4.447 | na | ~1506 |
| TAL ALκ liver | ~3.028 | na | ~35143 |
| VH6/VL3-p5 | | | |
| rVλ6Wil | 8.457 | 3.49E−09 | 65.3 |
| Per125 wtATTR | 7.404 | 3.94E−08 | 33.9 |
| KEN hATTR | 7.18 | 6.61E−08 | 16.9 |
| SHI ALλ liver | 7.303 | 4.98E−08 | 29.8 |
| TAL ALκ liver | 7.314 | 4.85E−08 | 29.5 |
| VH9/VL4-p5 | | | |
| rVλ6Wil | 8.393 | 4.05E−09 | 71.02 |
| Per125 wtATTR | 7.611 | 2.45E−08 | 58.06 |
| KEN hATTR | 7.357 | 4.40E−08 | 37.79 |
| SHI ALλ liver | 7.709 | 1.95E−08 | 41.93 |
| TAL ALκ liver | 7.613 | 2.44E−08 | 60.05 |
| VH9/VL4-p5R | | | |
| rVλ6Wil | 8.408 | 3.91E−09 | 82.68 |
| Per125 wtATTR | 7.855 | 1.40E−08 | 55.74 |
| KEN hATTR | 7.683 | 2.07E−08 | 26.64 |
| SHI ALλ liver | 7.823 | 1.50E−08 | 40 |
| TAL ALκ liver | 7.901 | 1.26E−08 | 45.28 |

Example 4. Wil Fibrils Substrate Pull Down by Humanized Anti-Amyloid Antibodies

Figure 6:
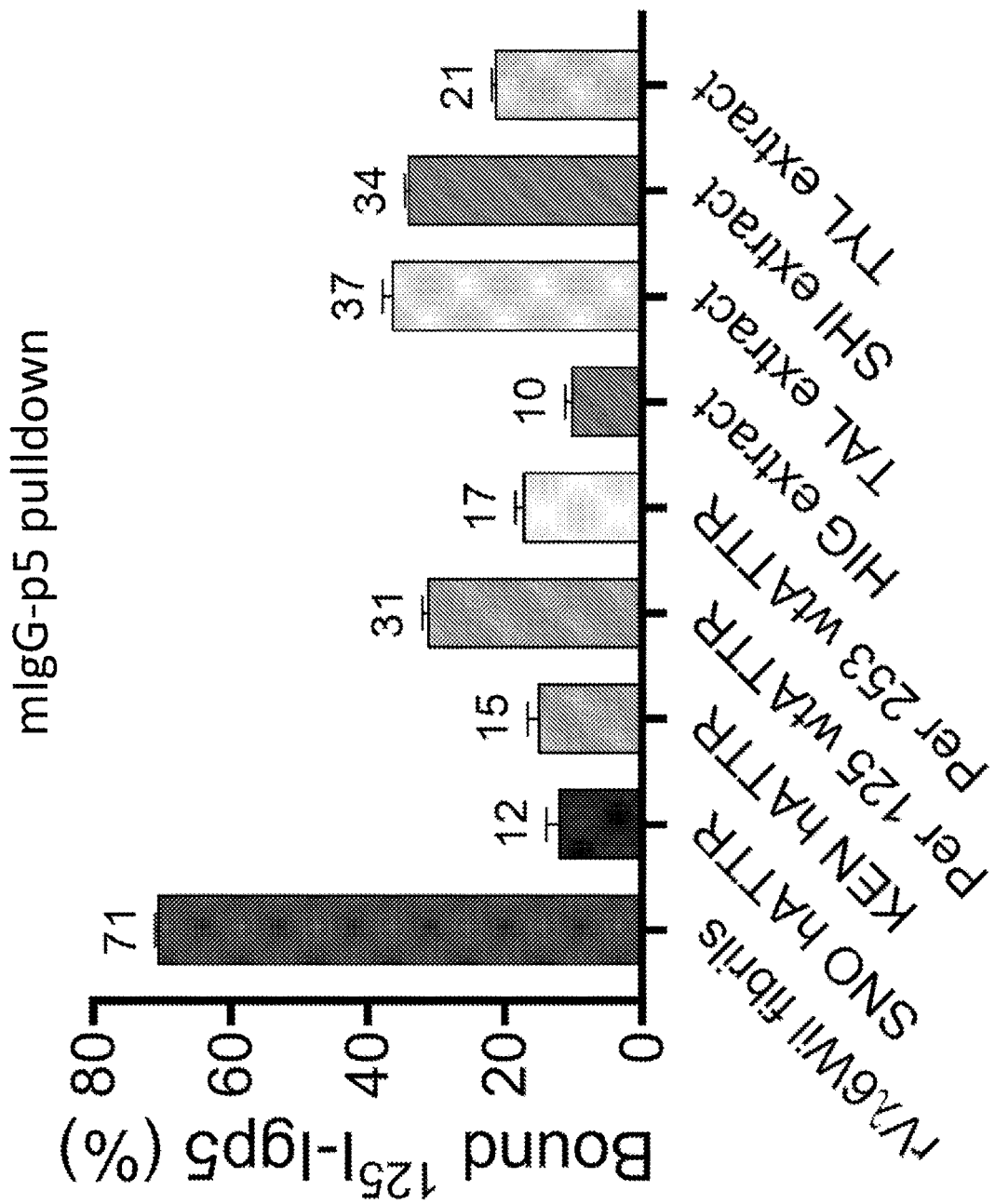
FIG. 6 shows the results of $^{125}$I-mIgp5 binding to rVλ6Wil amyloid-like fibrils and human amyloid extracts, obtained from tissues in a pulldown assay. The y-axis shows the percentage of bound $^{125}$I-mIgG-p5, and the percentage bound for each sample is indicated above the bars of the histograms. The x-axis shows the type of amyloid extract tested including rVλ6Wil fibrils, SNO hereditary (h) ATTR, KEN hATTR, Per 125 wtATTR, Per253 wild type (wt) ATTR, ALκ HIG extract, ALκ TAL extract, ALλ SHI extract, and ALλ TYL extract. The error bars represent the standard deviation.

The ability of anti-amyloid antibodies to pull down substrates was examined, as described in PCT/US2020/060596. mIgG-p5 yielded excellent binding to Wil fibrils and amyloid extracts in the pulldown assay (FIG. 6). The VH9/VL4 parent and variants ability to pulldown substrates was significantly decreased relative to mIgp5 as shown in Table E5, below. In Table E5, the values shown are the percent bound, and cells without data represent antibody/substrate combinations that were not tested.

TABLE E5

Summary of exemplary pulldown experiments

| Substrate | mIgp5 | VH9/VL4-p5 | VH9/VL4-p5R | VH9/VL4 | VH6/VL3-p5 |
|---|---|---|---|---|---|
| rVλ6Wil synthetic fibrils | 71 | 24.73 | 22.62 | 10.45 | 22.53 |
| Aβ(1-40) fibrils | | | | 7.38 | 20.57 |
| hIAPP fibril | | | | 2.46 | 4.82 |
| Vκ4(LEN(1-22) beads | | 54.44 | 50.17 | 57.44 | 54.87 |
| HIG ALκ1 | 10 | | | 0.19 | 0.51 |
| TAL ALκ | 37 | | | 0.72 | 0.94 |
| SHI ALλ | 34 | 1.97 | 1.22 | 0.68 | 0.60 |
| TYL ALλ | 21 | | | 0.56 | 0.69 |
| CAB ALκ4 | | | | 2.43 | 2.80 |
| SNO hATTR | 12 | | | 0.41 | 0.49 |
| KEN hATTR | 15 | | | 0.61 | 0.79 |
| wtATTR - PER125 | 31 | 1.33 | 1.12 | 1.36 | 1.00 |
| wtATTR - PER253 | 17 | | | 0.80 | 1.58 |

Figure 7A:
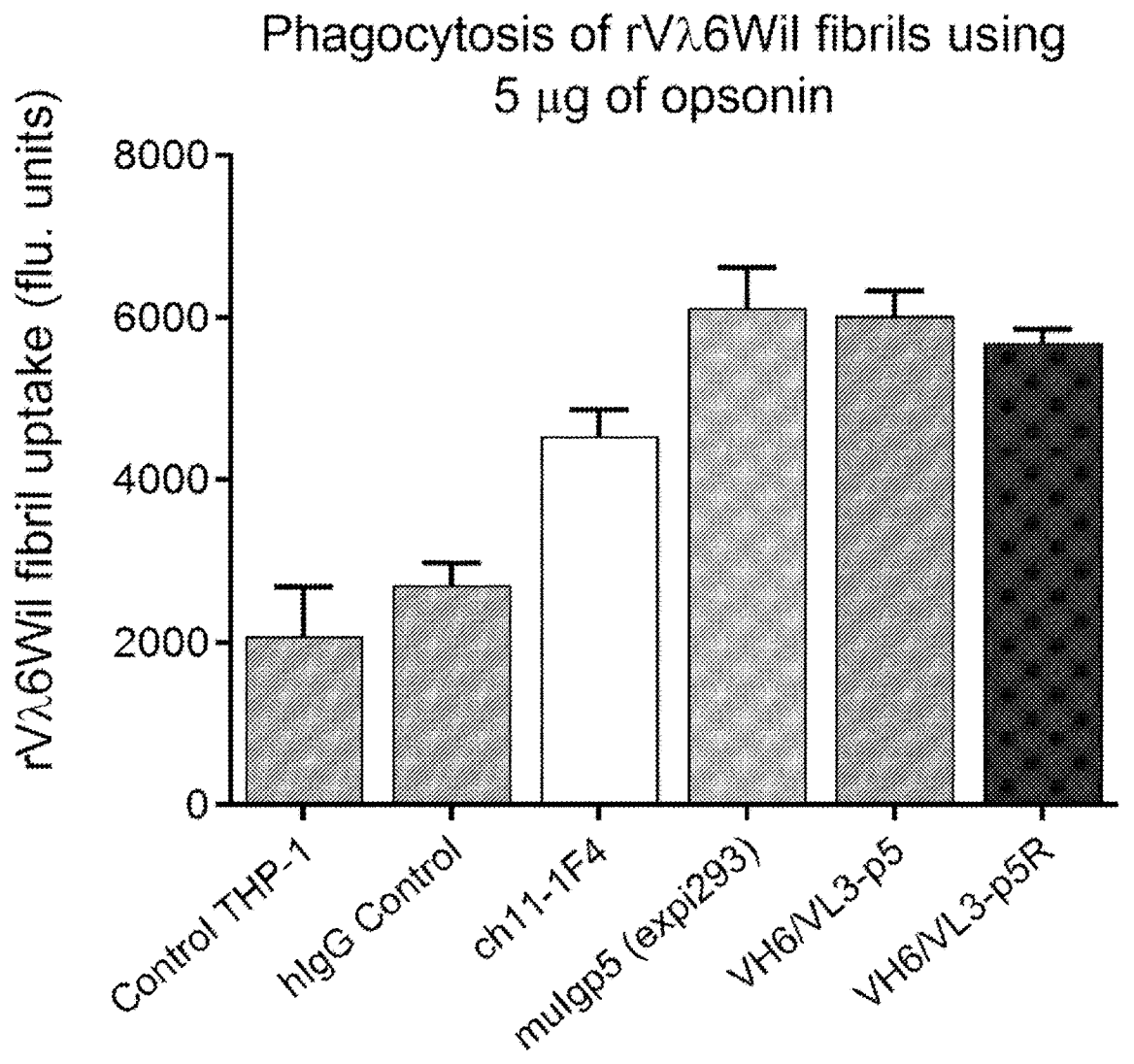
Figure 7B:
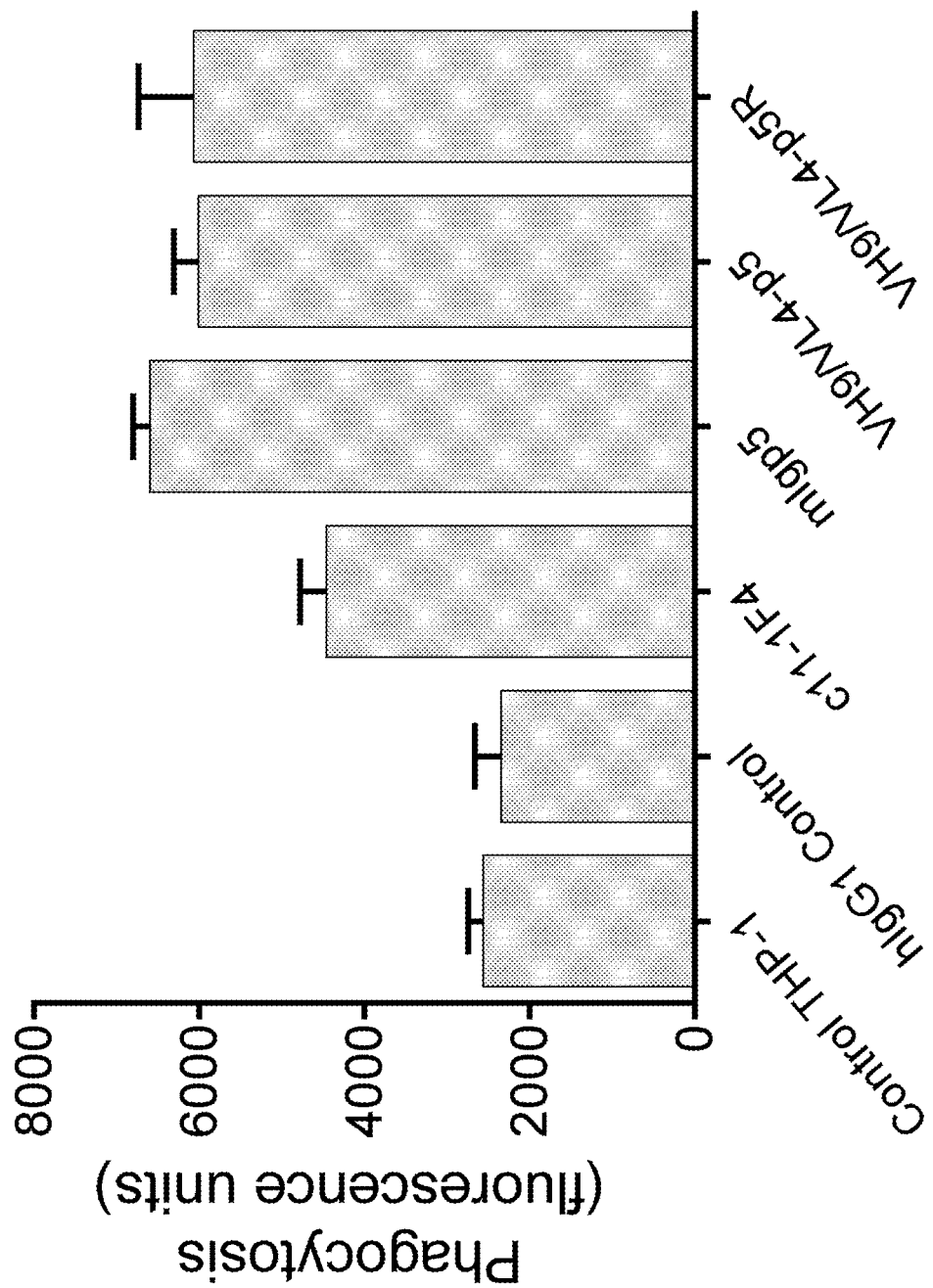
FIG. 7B shows phagocytosis of pHrodo red-labeled rVλ6Wil fibrils by macrophages in the presence of a THP-1 alone or with, hTgG control, c11-1F4, mIgp5, VH9/VL4-p5, or VH9/VL4-p5R, as indicated from left to right on the x-axis. The y-axis shows the level of phagocytosis (fluorescent units), and the error bars represent the standard deviation.
Figure 7C:
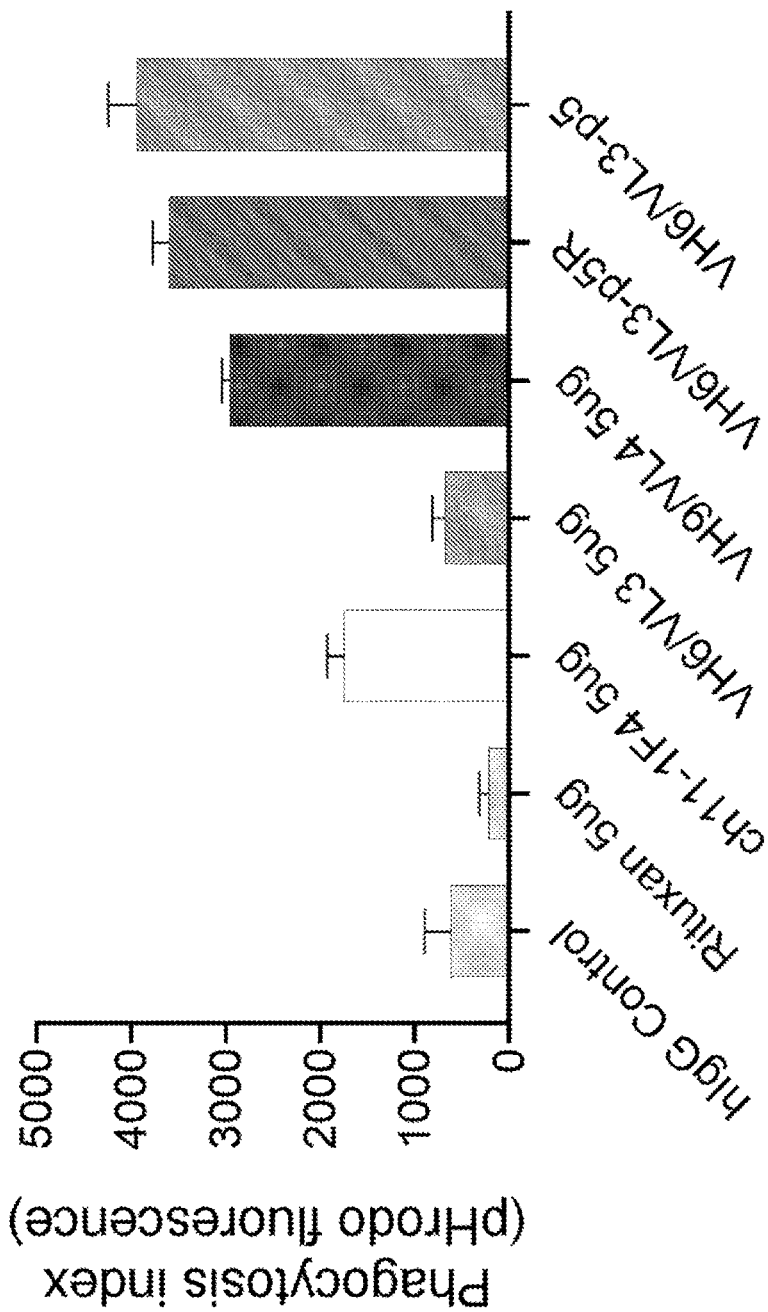
FIG. 7C shows phagocytosis of pHrodo red-labeled rVλ6Wil fibrils by macrophages in the presence of a hIgG control, 5 µg Rituxan (a chimeric mAb as a negative control), 5 µg c11-1F4, 5 µg VH6/VL3, 5 µg VH9/VL4, VH6/VL3-p5R, or VH6/VL3-p5, as indicated from left to right on the x-axis. The y-axis shows the level of phagocytosis (pHrodo fluorescence), and the error bars represent the standard deviation.

The ability of humanized anti-amyloid antibodies to act as opsonins for amyloid fibrils (i.e., promote the phagocytosis of amyloid fibrils) was tested, as described in PCT/US2020/060596. VH9/VL4-p5 and VH9/VL4-p5R promoted rVλ6Wil fibril uptake better than VH6/VL3-p5 and VH6/VL3-p5R did, which was consistent with the difference in ELISA binding data described above (see FIG. 7A and FIG. 7B). VH9/VL4 without peptide was approximately as good as VH6/VL3 with p5 or p5R attached and many fold better than VH6/V13 without peptide, as shown in FIG. 7C. VH9/VL4 alone was a better opsonin than c11-1F4 (FIG. 7B). VH6/VL3-p5 and VH6/VL3-p5R promoted equivalent levels of fibril uptake to the mIgp5, and performed better than c11-1F4 (FIG. 7A). VH9/VL4-p5 and VH9/VL4-p5R also promoted equivalent levels of fibril uptake to mIgp5, and performed better than c11-1F4 (FIG. 7B). Surprisingly, the humanized anti-amyloid antibodies conjugated to the p5 or p5R peptides provided significantly better opsonization than c11-1F4.

Figure 8A:
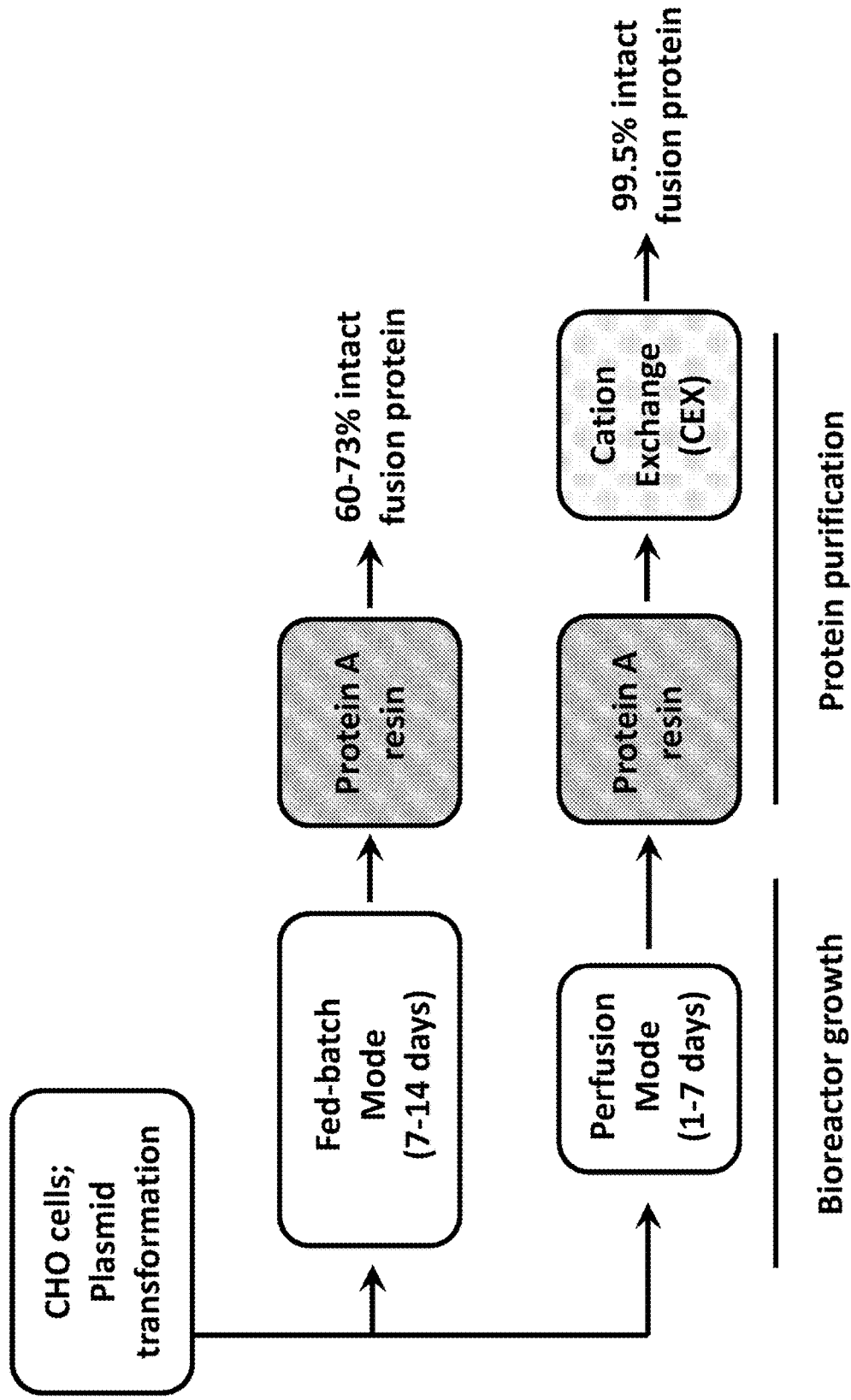
FIG. 8A shows fed-batch and perfusion workflows used to produce intact VH9-D54E/VL4-N33 S-VSPSV-p5R. Purity (% intact fusion protein) is indicated for each production method.
Figure 8B:
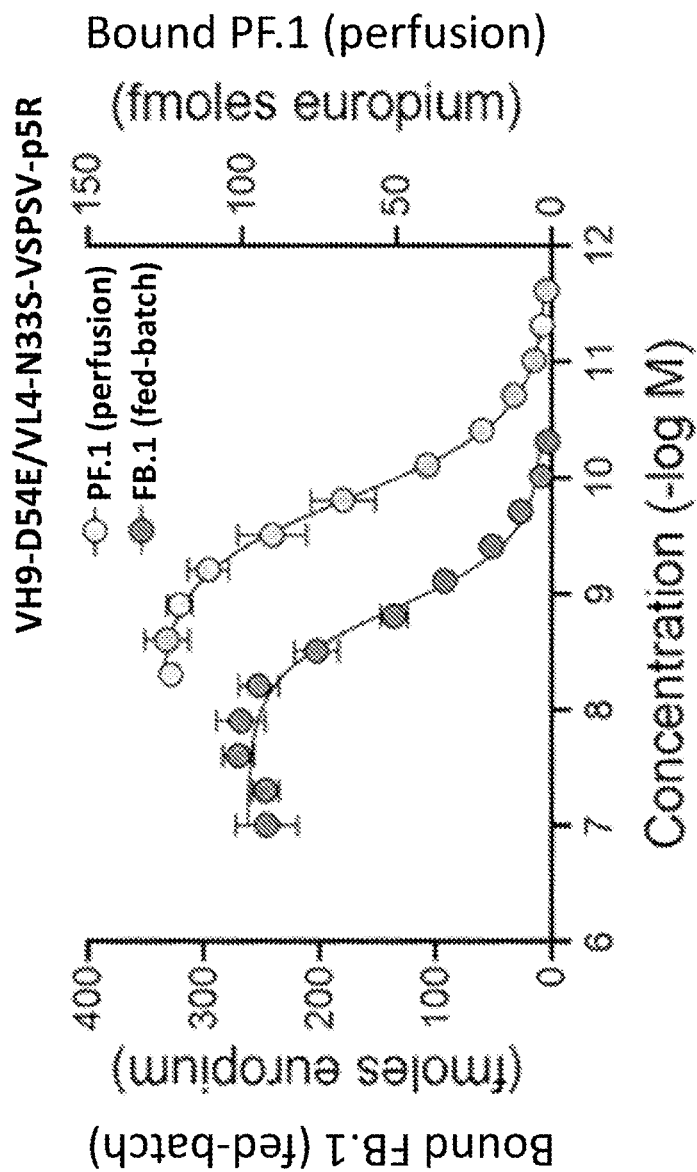
FIG. 8B shows the results of a binding experiment testing the affinity of fed-batch purified FB.1 and perfusion purified PF.1 on rVλWIL. The left y-axis scale is used for fed-batch purified FB.1 and the right y-axis scale is used for perfusion purified PF.1.

Example 5. Fed-Batch and Perfusion Production of VH9-D54E/VL4-N33S-p5R; Binding of Amyloid Substrate Fed-batch and other semi-continuous culturing methods are often used for production of recombinant proteins and antibodies due to their high culturing density, high product yield, and flexible productivity applications. However, high density cultures can influence the activity of inhibitory enzymes and toxins that may be detrimental to the overall production yield or strategy. Evaluation of the expression of early antibody-peptide fusion protein constructs by mammalian cells indicated that the fusion protein is highly susceptible to truncation, presumably by host-cell derived proteases. Perfusion is a type of continuous culturing method that avoids issues associated with high density culturing methods (e.g., fed-batch), but perfusion suffers from lower production yields and increased complexity. In this example, VH9-D54E/VL4-N33S-p5R (with VSPSV spacer) was isolated and assessed for purity (percent intact fusion protein) using exemplary fed-batch and perfusion mode culturing methods, overviewed in FIG. 8A. The binding affinity of antibody-peptide fusion protein, produced using a fed-batch and perfusion mode culturing methods, was tested, wherein substrate was amyloid like fibril rVλ6WIL (FIG. 8B).

Chinese hamster ovary cells were used for protein production by fed-batch mode and perfusion mode culturing methods. Cells were plated on 3-15 cm plates at a density of 0.1-2×10$^6$ cells/mL with fresh culture medium (chemically define, protein-free) with swirling at 120 RPM and incubated at 37° C. (5% $CO_2$). For production of VH9-D54E/VL4-N33S-VSPSV-p5R, 50-200×10$^6$ cells were passaged in fresh medium at 1×10$^6$ cells/mL the day prior to transfection with a plasmid encoding an antibody heavy chain comprising VH9-D54E and another plasmid encoding an antibody light chain comprising VL4-N33S-VSPSV-p5R. Cells were washed and transferred to fresh medium for either fed-batch mode culturing or perfusion mode culturing. Secreted antibody-peptide fusion protein (VH9-D54E/VL4-N33S-VSPSV-p5R) was collected from the fed-batch culture after about 7 days. Collected antibody peptide fusion protein was then applied to a protein A chromatography column, followed by anion exchange chromatography column. Eluate from the anion exchange column was collected and the isolated antibody-peptide fusion protein from this fed-batch culturing method was designated FB.1 (fed-batch 1).

Table E6 shows the mass spectrometry purity analysis of the antibody-peptide fusion protein using an alternative fed-batch culturing method.

TABLE E6

Mass spectrometry (MS) purity analysis of antibody-peptide fusion protein after an alternative fed-batch mode culturing method

| Antibody light chain | % (Day 10) | % (Day 14) |
|---|---|---|
| Truncated | 27.0 | 39.9 |
| Full-length | 73.0 | 60.1 |

To remedy the truncation observed during fed-batch cell culture, perfusion cell culture was evaluated. Perfusion cells were grown in a bioreactor, wherein the cell culture was passed through a membrane cartridge which retained cells but allowed passage of proteins away from cells and cellular debris. Secreted antibody-peptide fusion protein (VH9-D54E/VL4-N33S-VSPSV-p5R) was collected, after 1 or 7 days, and was immediately staged for sample processing. Secreted antibody peptide fusion protein was then applied to a protein A chromatography column, followed by anion exchange chromatography column. Eluate from the anion exchange column was collected and further subjected to cation exchange (CEX) chromatography, wherein the sample was loaded at a loading density between 20.0 and 50.0 g/L resin, washed with wash buffer comprising 260 mM NaCl (pH 5.5) and then eluted with elution buffer comprising 400 mM NaCL (pH 5.5). Application of the antibody-peptide fusion protein to the CEX column allowed for separation of truncated forms of the antibody-peptide fusion protein from the intact antibody-peptide fusion protein. Truncated forms of the antibody-peptide fusion protein were removed during the wash step with the wash buffer. Intact antibody-peptide fusion protein was eluted with elution buffer. Eluate from the CEX column was collected and analyzed sodium dodecyl sulfate capillary electrophoresis (CE-SDS) to determine the purity of the isolated antibody-peptide fusion protein. Over 99% purity was achieved using the perfusion method with the CEX column chromatography (Table E7). This eluate was designated PF.1 (perfusion 1) and was prepared for amyloid substrate binding analysis.

TABLE E7

Purity analysis of antibody-peptide fusion protein after CEX chromatography

| Peak No. | Load Material | Wash buffer (NaCl mM) | Yield (%) | CE-SDS (%, purity) |
|---|---|---|---|---|
| 1 | CEX Load | 200 | 42.2 | 12.1 |
| 2 | (47.5% purity) | 260 | 18.1 | 62.6 |
| 3 |  | 400 | 34.5 | 99.9 |

To assess the functional consequence of antibody-peptide fusion protein purity, obtain via fed-batch or perfusion mode production schemes, FB.1 and PF.1 antibody-peptide fusion proteins were prepared for amyloid substrate binding analysis. Amyloid like fibril rVλ6WIL was used as the substrate for investigating binding affinities of FB.1 or PF.1. The FB.1 antibody-peptide fusion protein was added to the wells in 2-fold serial dilution starting at 100 nM, and the PF.1 antibody-peptide fusion protein was added to the wells in 2-fold serial dilution starting at 5 nM. Detection of bound FB.1 or PF.1 was assessed by measuring time-resolved fluorescence, following addition of a biotinylated goat anti-human Fc-reactive secondary antibody and streptavidin-europium conjugate. The mean and standard deviation (SD) of three replicates were calculated and the potency (EC50) was determined following fitting with a sigmoidal four parameter logistic (4PL) equation with logarithmic x-axis (Prism) (FIG. 8B).

The estimated potency (EC50) value for the binding of FB.1 to rVλ6WIL was 13.4 nM, while the EC50 value for the binding of PF.1 to rVλ6WIL was 0.15 nM. These data demonstrate that the highly pure intact antibody-peptide fusion protein produced using the perfusion mode culturing and cation exchange chromatography method (PF.1) has a significantly higher binding affinity for the rVλ6WIL amyloid substrate than the antibody-peptide fusion protein produced using the fed-batch culturing method (FB.1). For all examples hereafter, antibody-peptide fusion protein was produced using the perfusion culturing and cation exchange chromatography method describe in this example.

Example 6. Biodistribution of PF.1 (VH9-D54E/VL4-N33S-p5R) in Mice

Figure 9A:
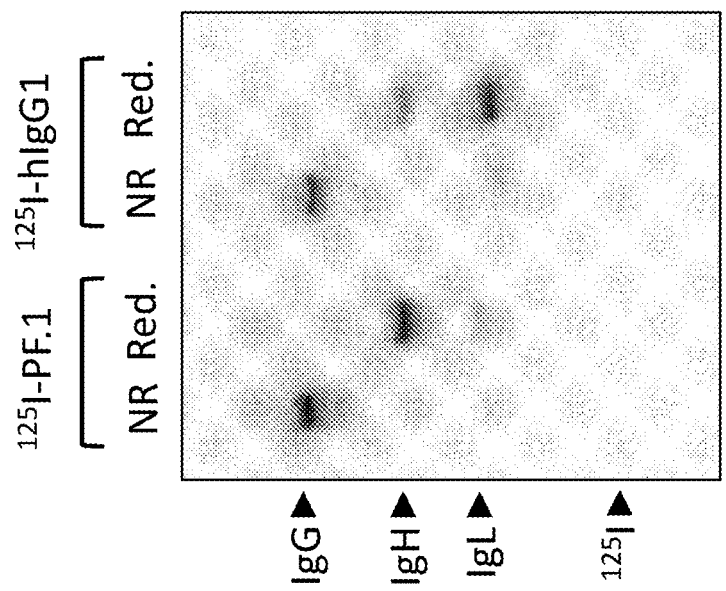
FIG. 9A shows the gel analysis of radiolabeled (125I) PF. 1 antibody-peptide fusion protein, in comparison to the radiolabeled (125I) antibody higG1 control. Reduced (Red.) and not reduced (NR) samples are shown, and the positions of the IgG, IgH, and IgL for each protein are indicated. Free radioiodide (125I) is also labeled.
Figure 9B:
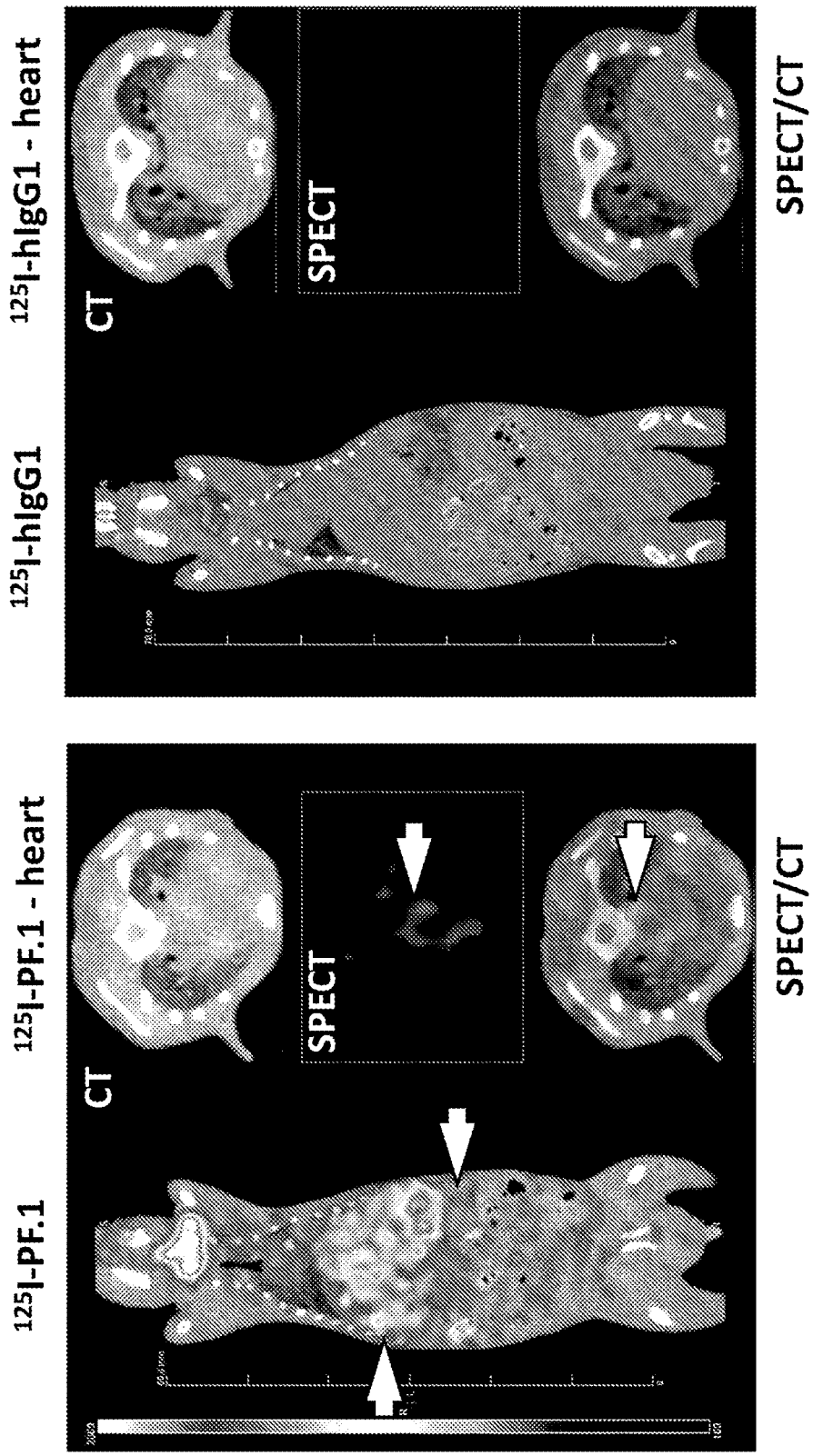
FIG. 9B shows single photon emission computed tomography (SPECT) and computed tomography (CT) imaging of systemic AA amyloidosis mice after 24 hours post-injection with either PF.1 or 125I-hIgG1.
Figure 9C:
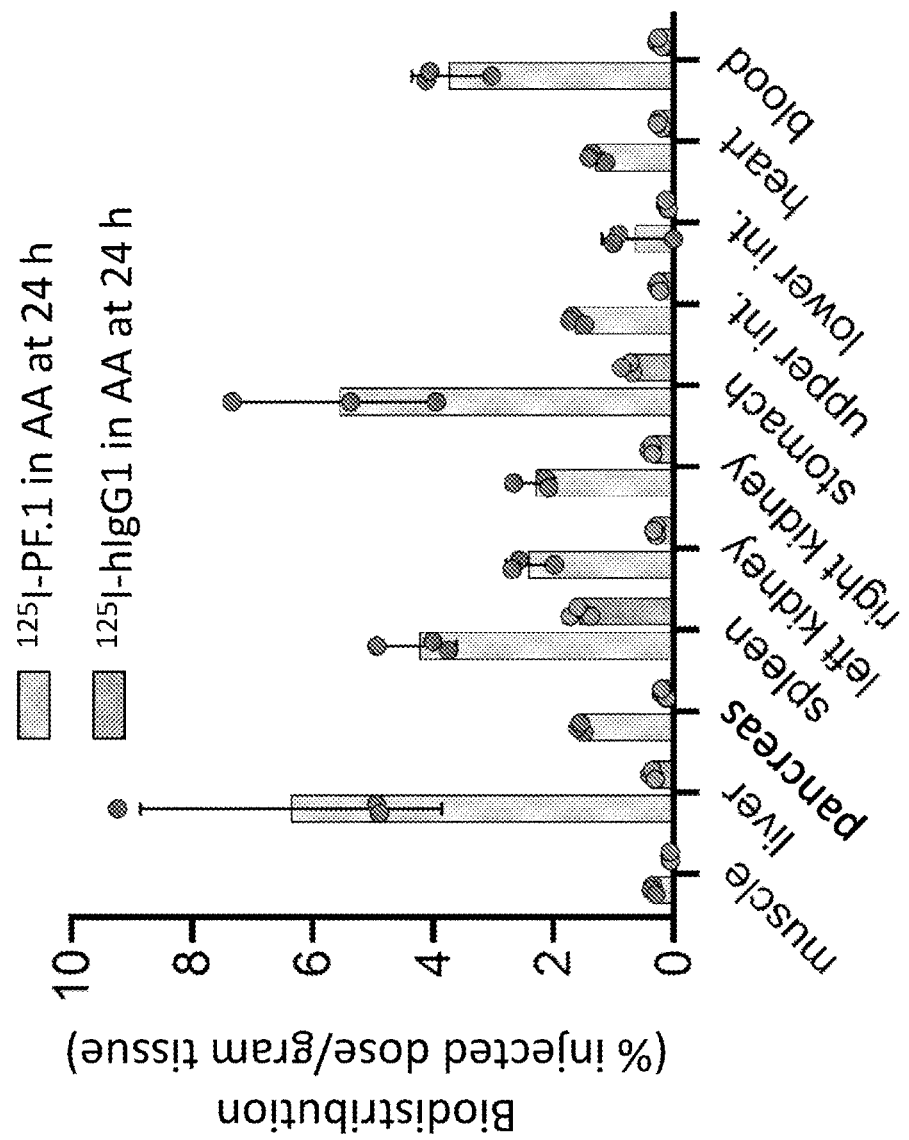
FIG. 9C shows the biodistribution of 125I-PF.1 and 125I-hIgG1 among different tissues in AA mice after 24 hours post-injection.
Figure 9D:
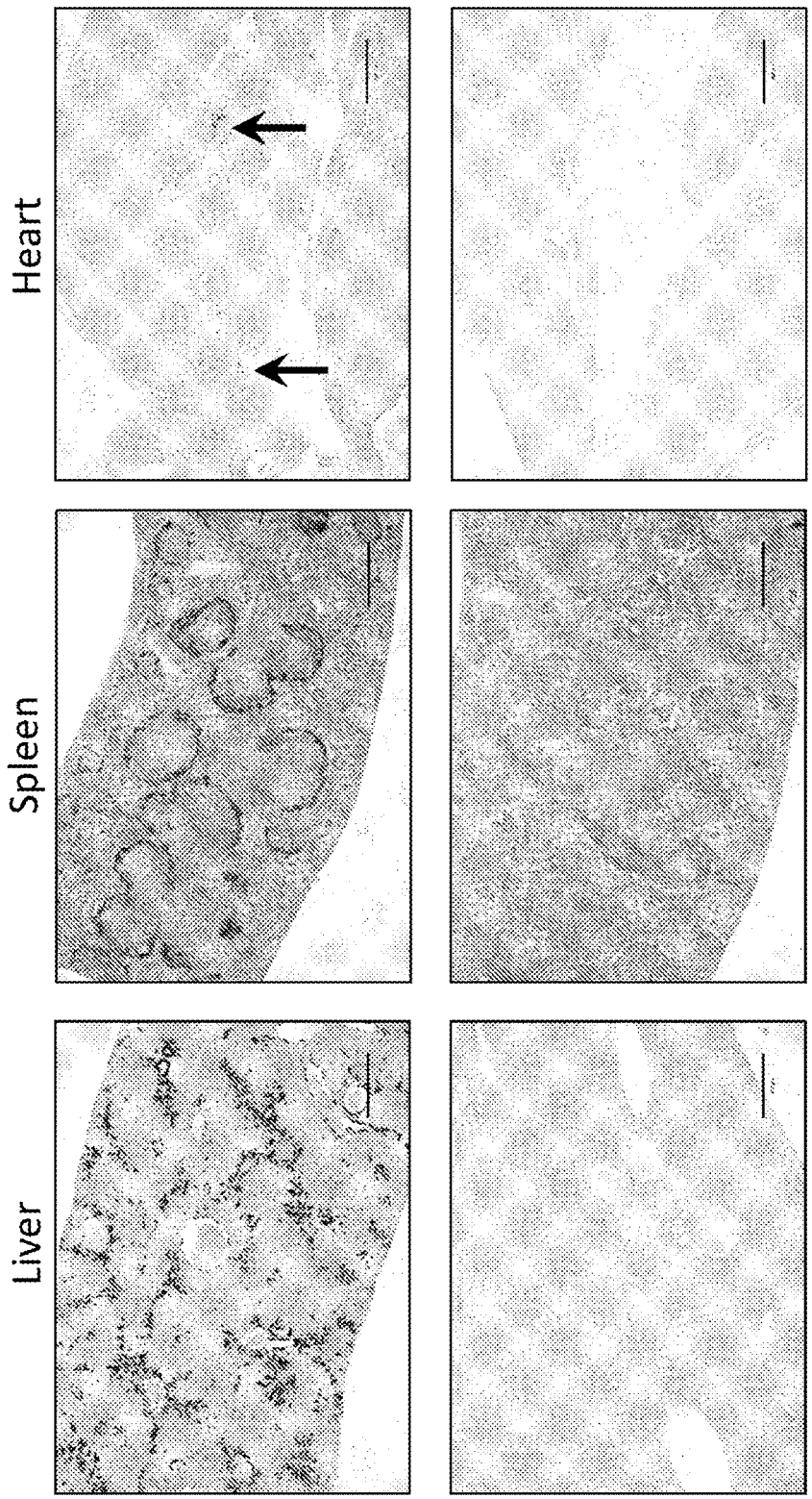
FIG. 9D shows microautoradiography of liver (left), spleen (center), and heart (right) tissues 24 hours post injection of AA mice with either 125I-PF.1 or 125I-hIgG1.
Figure 10A:
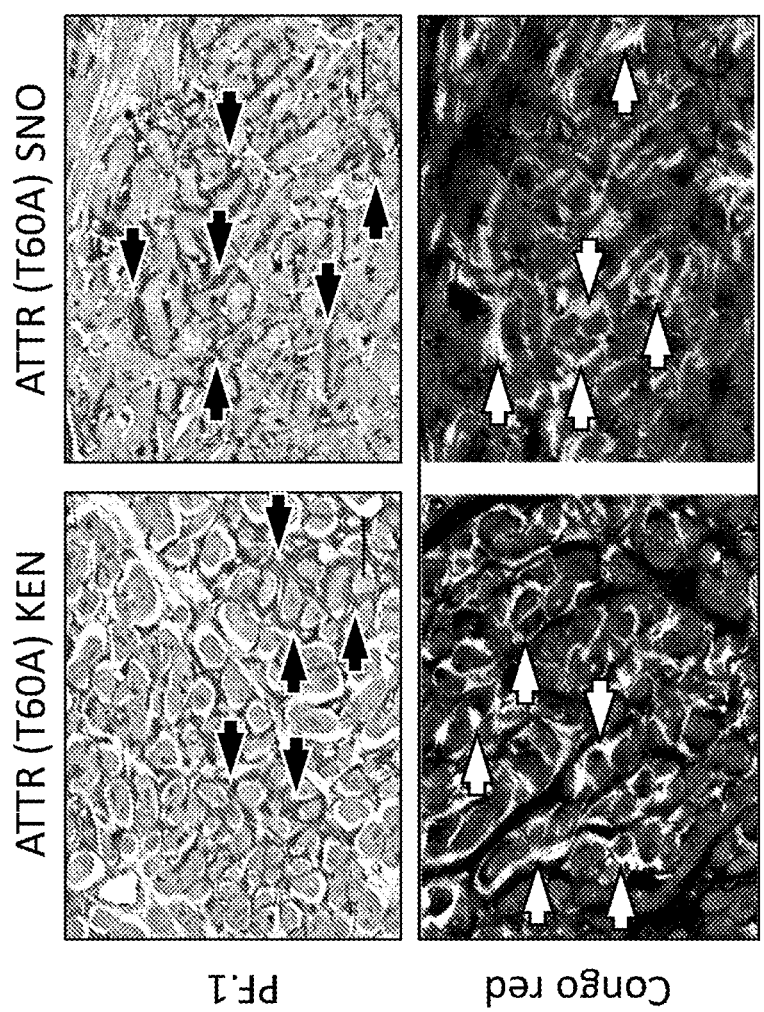
FIGS. 10A-10E shows immunohistochemical staining of different human tissues (heart, kidney, spleen, and brain) containing ATTR, AL, ALETC2 or Aβ amyloid with biotinylated PF.1 and Congo red. Black arrows highlight biotinylated PF.1 bound to the tissue sample and white arrows highlight the presence of amyloid in the tissue sample (Congo red staining).
Figure 10B:
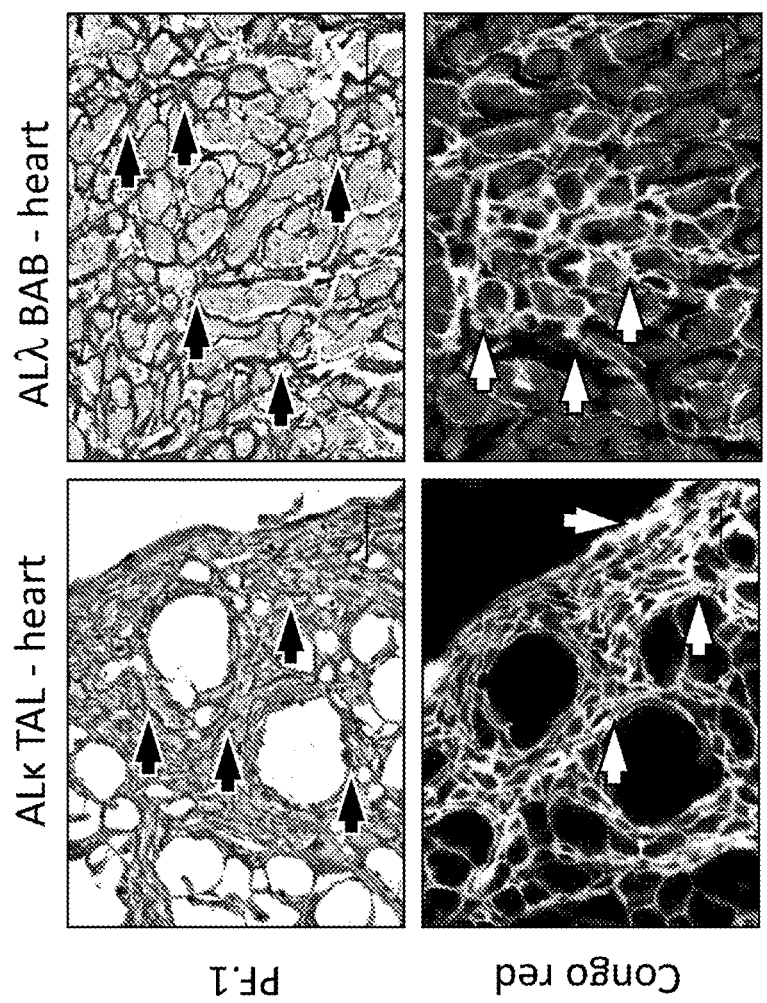
Figure 10C:
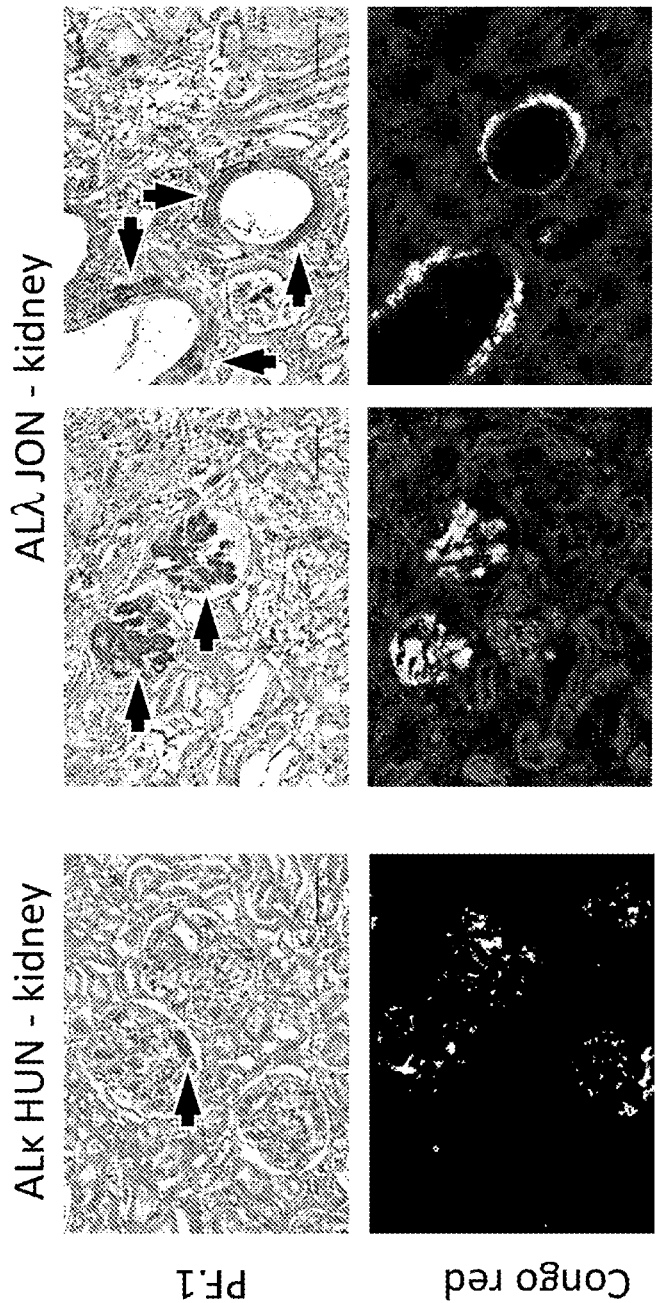
Figure 10D:
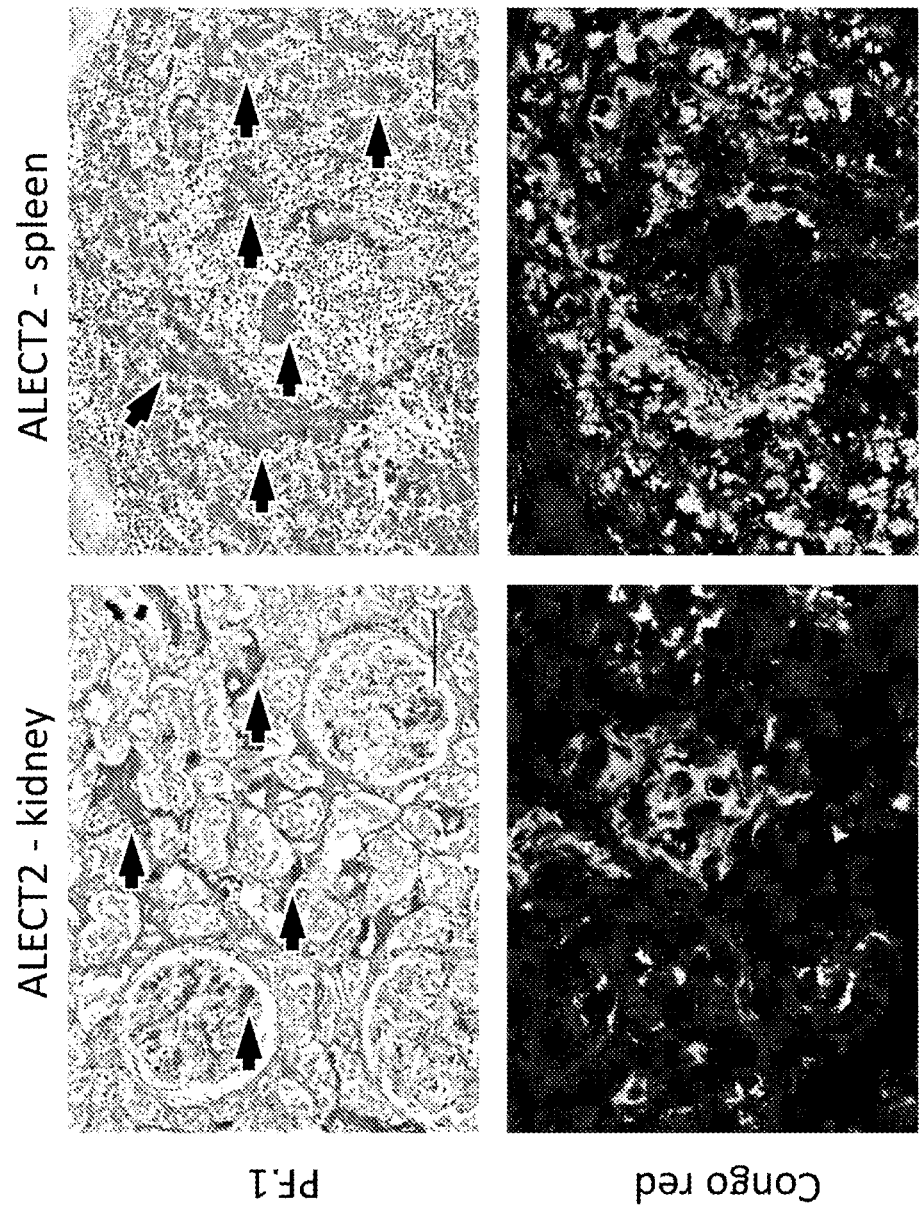
Figure 10E:
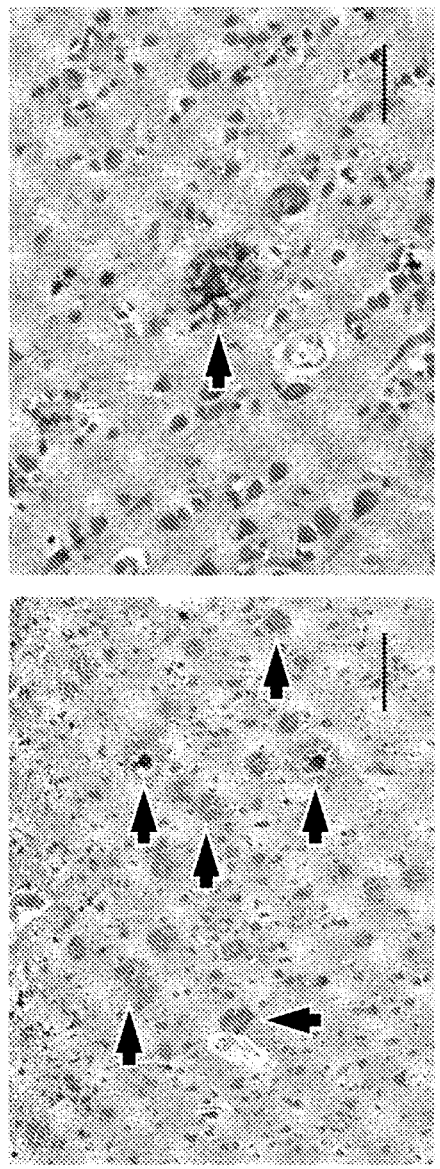

For this study, PF.1 (VH9-D54E/VL4-N33S-p5R with VSPSV spacer) was expressed by stably transfected CHO cells and produced by the perfusion tissue culture method for 1 day. The PF.1 antibody-peptide fusion was purified by Protein A and cation exchange chromatography as described in Example 5. The PF.1 antibody-peptide fusion and control hIgG1 were radiolabeled with iodine-125 by oxidative incorporation into tyrosine side chains. The free radioiodide was separated by size exclusion chromatography and the radiopurity assessed by SDS-PAGE and autoradiography (FIG. 9A). Both the heavy and light chain proteins of the reagents were radiolabeled and there was no evidence of free radioiodide. The light chain of the PF.1 was uniform (single species) and had a visibly higher molecular weight as compared to the control IgG1 due to the presence of the p5R peptide.

Approximately 100 μCi (10 μg reagent) was injected intravenously (IV) into the lateral tail vein of mice with systemic AA amyloidosis, principally involving the liver and spleen. At 24 hours post-injection the mice (n=3 per group) were euthanized by isoflurane overdose and the SPECT/CT images acquired (FIG. 9B). The 125I-PF.1 images revealed retention of radioactivity in the liver, spleen and GI tract of the AA mice, which contrasted to images of 125I-hIgG1 in AA mice at 24 hours post-injection. In addition, there was visually more radioactivity in the atrial region of the mouse heart in animals administered 125I-PF.1 as compared to the control reagent, which may indicate greater blood pool radioactivity or binding to the scant cardiac amyloid deposits in this mouse model.

Immediately thereafter, samples or organs and blood were collected for measurement of tissue associated radioactivity as a measure of the biodistribution of the reagents in the organs, wherein biodistribution was defined as a percentage of injected dose measured per gram tissue. Three mice per group were examined and the mean biodistribution with standard deviation (SD) was calculated. Organ analysis included muscle, liver, pancreas, spleen, left kidney, right kidney, stomach, upper intestine, lower intestine, heart, lung, and blood. This analysis revealed significantly higher retention of the 125I-PF.1 in the liver, spleen, kidneys, and stomach compared to the control hIgG1 (FIG. 9C). This suggests that the PF.1 reagent is selectively retained by amyloid in these organs.

Then distribution of the radiolabeled reagents in the mouse organs was assessed using microautoradiography. Briefly, samples of tissue were fixed for 24 hours in 10% buffered formalin, embedded in paraffin blocks and 6 μm-thick sections of tissue prepared on glass slides. The slides were exposed to photographic emulsion for three days and then counterstained with hematoxylin and eosin (H&E) stain. The presence of radioactivity in the tissues was evidenced by the deposition of black silver grains. In all organs evaluated the binding of 125I-PF.1 was observed in associated with amyloid deposits in the tissue, indicative of specific binding to the pathology (FIG. 9D) showing representative sections of liver, spleen and heart (bar=500 μm). In contrast, no retention of 125I-hIgG1 control was seen.

Example 7. Binding of PF.1 to Amyloid in Human Tissues

Formalin-fixed paraffin embedded sections were prepared from several human tissues containing ATTR (FIG. 10A), AL (FIGS. 10B and 10C), or ALETC2 (FIG. 10D) amyloid. An additional sample of brain tissue from a patient with Alzheimer's disease was also evaluated (FIG. 10E). The tissues were stained with biotinylated PF.1 (VH9-D54E/VL4-N33S-p5R with VSPSV spacer; 2 μg/mL in PBS) using standard immunohistochemical methods and visualized following addition of diaminobenzidine (black arrows). The presence of amyloid in slides from the same tissues was visualized by Congo red fluorescence following staining of the tissues with a solution of alkaline Congo red (white arrows).

PF.1 bound specifically to the cardiac amyloid deposits surrounding the cardiomyocytes in two samples of ATTRv amyloidosis (T60A KEN and T60A SNO) (FIG. 10A) and two samples of AL amyloidosis (ALκ TAL and ALκ BAB) (FIG. 10B). Similarly, specific binding with amyloid was observed with AL amyloid deposits (ALκ HUN and ALκ JON) in the kidney (FIG. 10C). Specific binding of PF.1 to ALECT2 amyloid was observed in renal and splenic tissue samples (FIG. 10D). Finally, the diffuse and core plaques composed of A3 amyloid in the brain of a patient with Alzheimer's disease were positively stained with PF.1 (FIG. 10E).

These data demonstrate the specific reactivity of PF.1 with tissue amyloid deposits of varied types in diverse tissues. Thus, the pan amyloid reactivity of PF.1, mediated by the p5R peptide, is evidenced by immunohistochemical staining using tissues from the four most common forms of amyloid-related diseases.

Example 8. Phagocytosis of Human AL Amyloid Extract by PF.1 In Vivo

A sample of human AL (BAL) amyloid extract was labeled with the pH sensitive dye succinimidyl-pHrodo red fluorophore. pHrodo red exhibits weak fluorescence at pH 7.5 but is enhanced as the pH becomes more acidic, as is found in the phagolysosome of macrophages following phagocytosis. Human AL (BAL) amyloid extract (roughly 10% w/w pHrodo red-labeled material) was preincubated with PF.1 (VH9-D54E/VL4-N33S-p5R with VSPSV spacer; 500 μg PF.1 per 2 mg of AL extract) for roughly 30 minutes. As a control, AL extract was incubated in a similar volume of PBS without PF.1. Immunocompromised (NU/NU) mice (n=4 per group) were administered 2 mg of the PF.1-coated AL extract subcutaneously in the back. The fluorescence emission from the pHrodo red-labeled amyloid was detected by optical imaging of the mice under isoflurane (1-2% in air) anesthesia. Mice were imaged 1 day, 5 days, 7 days, 10 days, and 12 days post injection of the amyloid and the fluorescence emission quantified.

Figure 11B:
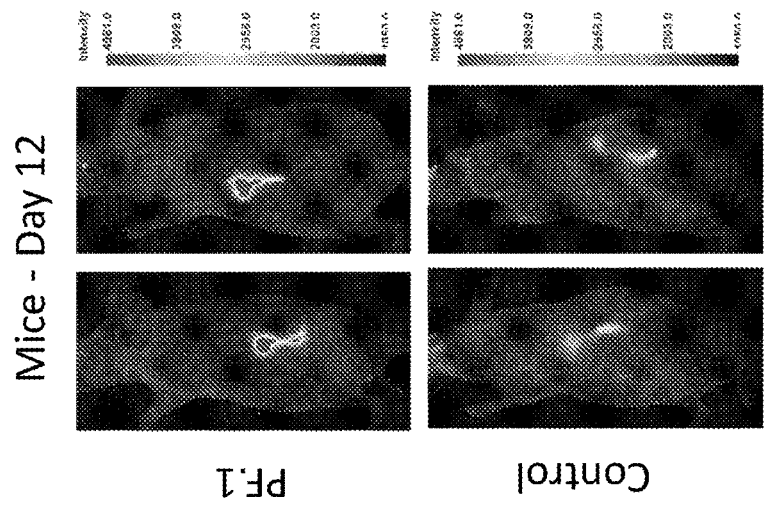
FIG. 11B shows the fluorescence emission of the PF.1-treated and control-treated mice at 12 days post injection.
Figure 11A:
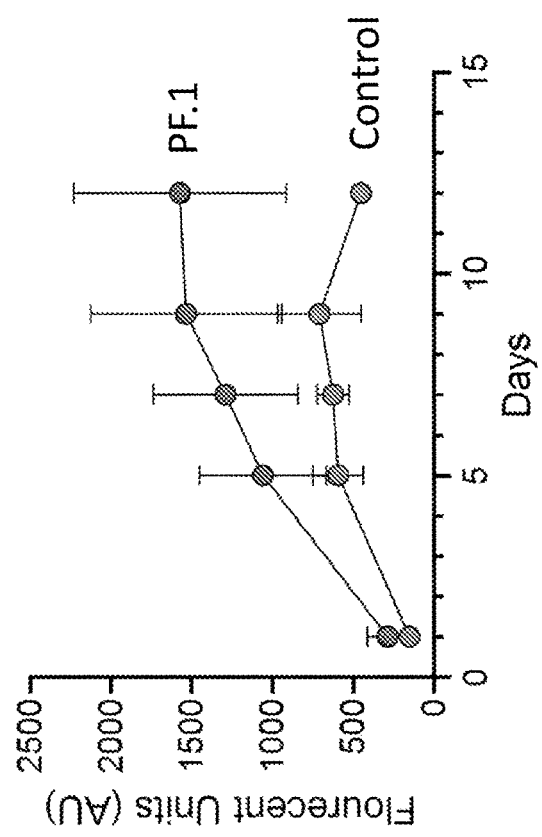
FIG. 11A shows quantified fluorescence emission from the pHrodo red in mice post injection with pHrodo red-labeled amyloid, wherein the injected amyloid was either preincubated with PF.1 or alone. Increased fluorescence emission is indicative of amyloid phagocytosis.

Preincubation of the amyloid with PF.1 resulted in a rapid and sustained increase in phagocytosis of the amyloid over 12 days post-injection as evidenced by the increase in pHrodo red fluorescence emission (FIG. 11A). In contrast, the fluorescence emission from the amyloid extract alone (control) was significantly lower (FIG. 11A). The difference in fluorescence emission between the PF.1-treated and control groups at 12 days post injection was visibly enhanced in the treated group (representative mice shown in FIG. 11B).

These data demonstrate that amyloid bound PF.1 can enhance the phagocytosis of amyloid by phagocytic cells, principally macrophages in vivo.

Example 9. Phagocytosis of Human AL Amyloid Extract by PF.1 In Vitro

Human AL extracts (ALκ or ALU) and human ATTR (v or wt) amyloid extracts were labeled with the pH sensitive dye succinimidyl-pHrodo red fluorophore, for use in an ex vivo phagocytosis assay. Human THP-1 cells were activated by addition of phorbol myristate acetate (PMA) and seeded onto the wells of a 24-well tissue culture plate. A 20-µg mass of amyloid extract was added to the wells with increasing amounts of PF.1 (VH9-D54E/VL4-N33S-p5R with VSPSV spacer) or control hIgG1 antibody (6 nM, 20 nM, 60 nM, and 200 nM) and the plates were incubated for 1 hour at 37° C. The wells were viewed using an inverted fluorescence microscope (Keyance BZ X800) and four digital images (4× objective) captured for each well. The fluorescence in each image was quantified using spectral segmentation and the mean and standard deviation (SD) of the four images determined (FIGS. 12A-12D).

The results demonstrate that PF.1 enhances phagocytosis of diverse amyloid extracts by activated human THP-1 macrophages in a dose-dependent manner with maximum effect in these assay conditions observed at approximately 60 nM PF.1 for ALκ extracts (FIG. 12A), ALλ extracts (FIG. 12B), ATTRv extracts (FIG. 12C), and ATTRwt extracts (FIG. 12D). The enhancement of fluorescence emission due to increased phagocytosis of the amyloid substrates was significantly greater than the control hIgG1 in all instances.

These data demonstrate that opsonization of human amyloid by PF.1 results in significant phagocytosis of the material by human macrophages.

Example 10. Potent Binding of Diverse Amyloid Substrates by PF.1

Synthetic amyloid like fibrils (rVλ6WIL and Aβ(1-40)) as well as human AL extracts (ALλ or ALκ) and human ATTRV and ATTRwt amyloid extracts were used as the substrate for investigating binding affinities of PF.1. The antibody-peptide conjugate was added to the wells in 2-fold serial dilution starting at 100 nM. For wells containing rVλ6WIL, the antibody-peptide conjugate was added to the wells in 2-fold serial dilution starting at 5 nM. Detection of bound PF.1 (VH9-D54E/VL4-N33S-p5R with VSPSV spacer) was assessed by measuring time-resolved fluorescence, following addition of a biotinylated goat anti-human Fc-reactive secondary antibody and streptavidin-europium conjugate. The mean and standard deviation (SD) of three replicates were calculated and the potency (EC50) was determined following fitting with a sigmoidal four parameter logistic (4PL) equation with logarithmic x-axis (Prism) (FIG. 13A). A non-reactive hIgG1 was used as a negative control in a parallel assay (FIG. 13B).

The estimated potency (EC50) values for the binding of PF.1 to the amyloid substrates ranged from 0.15 nM for synthetic fibrils to 0.6 nM for the ALκ(GRA) amyloid extract (Table E8). These data demonstrate that the high affinity binding of PF.1 for synthetic fibrils and human AL and ATTR amyloid extracts.

TABLE E8

| EC50 values for PF.1 binding of diverse amyloid substrates | |
|---|---|
| Amyloid Substrate | EC50 (nM) |
| rVλ6WIL | 0.15 |
| Aβ(1-40) | 0.15 |
| ATTRwt (125) | 0.18 |
| ATTRv (T60A, KEN) | 0.45 |
| ALλ (SHI) | 0.32 |
| ALκ (TAL) | 0.40 |
| ALλ (BAL) | 0.36 |
| ALλ (GRA) | 0.60 |

Aβ(1-40), 40 amino acid version of Aβ; wt, wild-type; v, variant type; T60A, mutation in transthyretin. 125, KEN, SHI, TAL, BAL, and GRA, are patient sample designations for ALκ and ALλ fibrils.

Example 11. Binding of Synthetic Amyloid Substrates by PF.7 In Vitro

Figure 14:
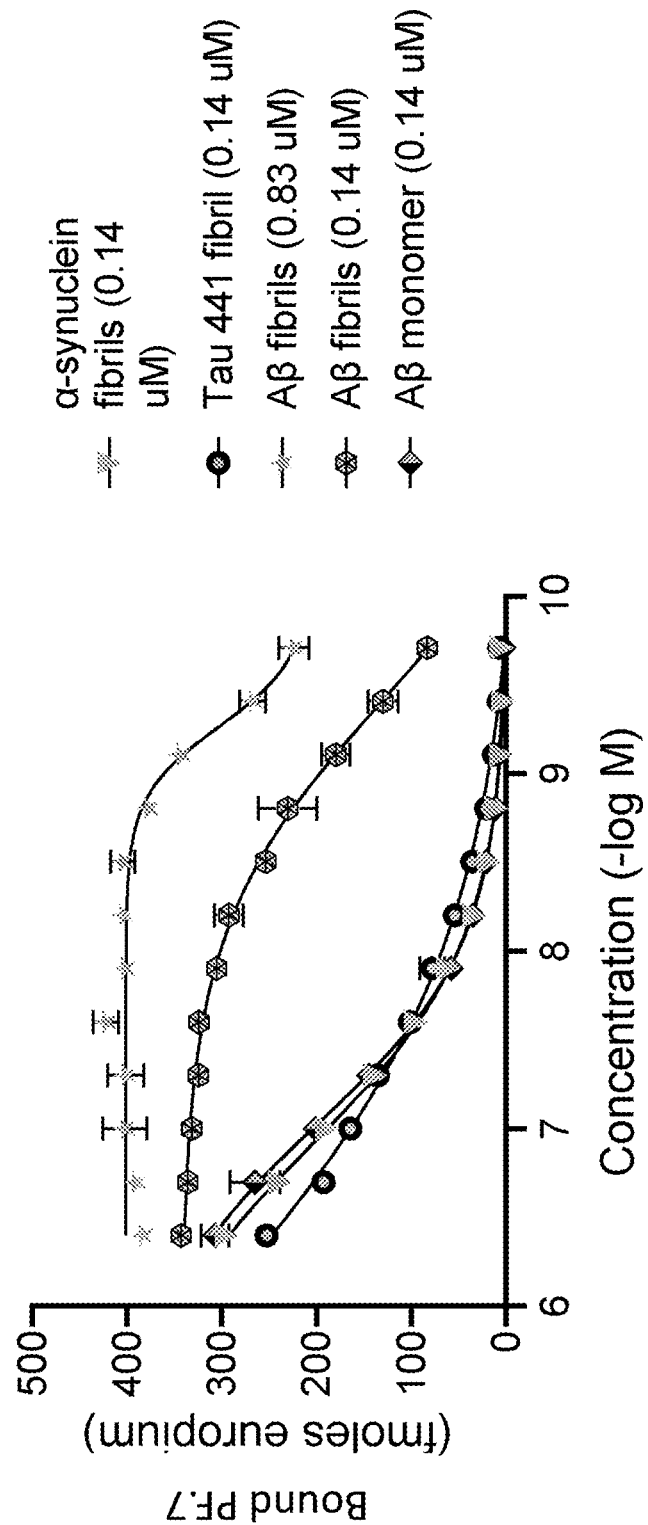
FIG. 14 shows the results of a binding experiment testing the affinity of PF.7 on synthetic amyloid-like fibrils α-synuclein, Tau 441, and Aβ(1-40). PF.7 is VH9-D54E/VL4-N33S-VSPSV-p5R antibody-peptide fusion protein collected after 7 days of perfusion culturing.

For this study VH9-D54E/VL4-N33S-p5R (with VSPSV spacer) was expressed by CHO cells and produced by the perfusion tissue culture method for 7 days, using a similar method as described for PF.1. The antibody-peptide fusion was purified by Protein A and cation exchange chromatography—the isolated material was designated PF.7. Synthetic amyloid like fibrils (Tau 441, α-synuclein, and Aβ(1-40)) were used as the substrate for PF.7 binding analysis. The PF.7 was added to the wells in 2-fold serial dilution starting at 100 nM. Detection of bound PF.7 was assessed by measuring time-resolved fluorescence, following addition of a biotinylated goat anti-human Fc-reactive secondary antibody and streptavidin-europium conjugate. The mean and standard deviation (SD) of three replicates were calculated and the potency (EC50) was determined following fitting with a sigmoidal four parameter logistic (4PL) equation with logarithmic x-axis (Prism) (FIG. 14). A non-reactive hIgG1 was used as a negative control in a parallel assay (FIG. 13B).

The estimated potency (EC50) values for the binding of PF.7 to the different fibril substrates were 127 nM, 1.3 uM, and 0.4 nM for α-synuclein, Tau 441, and Aβ(1-40) (Table E9).

TABLE E9

| EC50 values for PF.7 for synthetic fibril substrates. | |
|---|---|
| Synthetic fibril substrate | EC50 (nM |
| α-synuclein | 127 nM |
| Tau 441 | 1300 nM |
| Aβ(1-40) | 0.4 nM |

Figure 15:
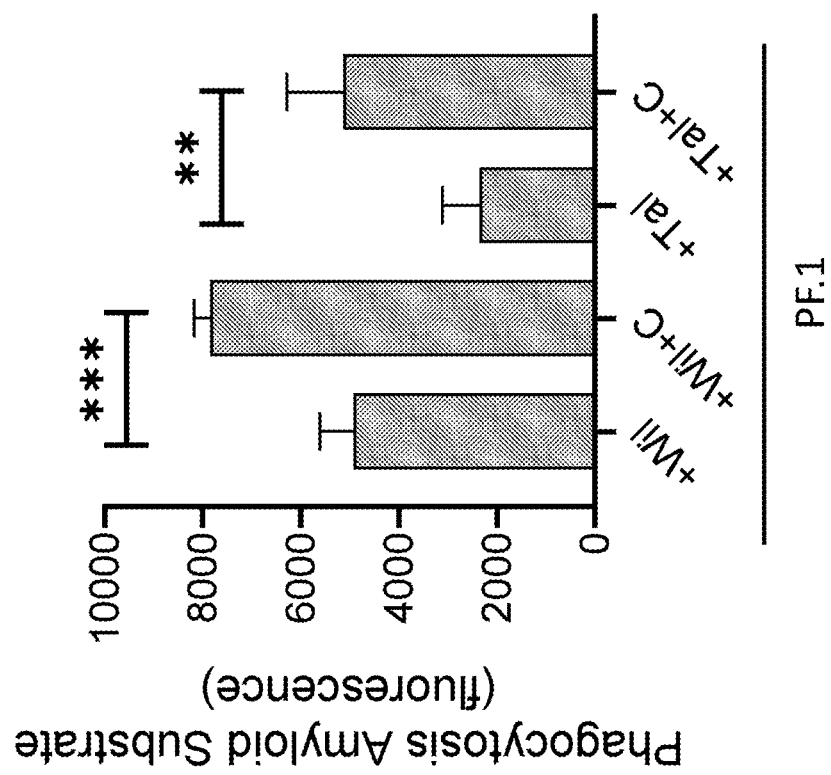
FIG. 15 shows the results of an ex vivo phagocytosis assay performed with PF.1 on rVλWIL (WIL) and ALκ (TAL) fibrils in the presence or absence of 20% human serum as a source of human complement. +C indicates the presence of human serum complement.

Example 12. Phagocytosis of Human AL Amyloid Extract by PF.1 In Vitro is Enhanced by Human Serum Synthetic rVλ6WIL (Wil) fibrils and human ALκ (TAL) amyloid extract were labeled with the pH sensitive dye succinimidyl-pHrodo red fluorophore, for use in an ex vivo phagocytosis assay. Human THP-1 cells were activated by addition of phorbol myristate acetate (PMA) and seeded onto the wells of a 24-well tissue culture plate. A 20-μg mass of amyloid extract was added to the wells with 60 nM PF.1 (V19-D54E/VL4-N33S-p5R with VSPSV spacer) in the presence or absence of 20% human serum as a source of complement. The plates were incubated for 1 hour at 37° C. The wells were viewed using an inverted fluorescence microscope (Keyance BZ X800) and four digital images (4× objective) captured for each well. The fluorescence in each image was quantified using spectral segmentation and the mean and standard deviation (SD) of the four images determined (FIG. 15).

The results demonstrate that human serum as a source of complement significantly enhanced the phagocytosis of amyloid substrates following opsonization by PF.1 by activated human THP-1 macrophages.

These data demonstrate that opsonization of human amyloid by PF.1 and phagocytosis by human macrophages can be significantly enhanced by human serum, as a source of complement.

IX. EXEMPLARY EMBODIMENTS

1. An antibody-peptide fusion protein, comprising: an amyloid-reactive peptide; and an antibody that binds to human amyloid fibrils, wherein antibody comprises a heavy chain comprising a heavy chain variable region (VH) and a light chain comprising a light chain variable region (VL), wherein the amyloid-reactive peptide and antibody are linked at the C-terminal end of the light chain via a spacer, or without a spacer.
2. The antibody-peptide fusion protein of embodiment 1, wherein the amyloid-reactive peptide is linked to the C-terminal end of the light chain via a spacer.
3. The antibody-peptide fusion protein of embodiment 1 or embodiment 2, wherein the spacer is a peptide spacer.
4. The antibody-peptide fusion protein of any one of the preceding embodiments, wherein the light chain further comprises a light chain constant region, and the heavy chain comprises a heavy chain constant region.
5. The antibody-peptide fusion protein of any one of the preceding embodiments, wherein the antibody-peptide fusion protein comprises two light chains and two heavy chains.
6. The antibody-peptide fusion protein of any one of the preceding embodiments, wherein the spacer comprises an amino acid sequence selected from the group consisting of SEQ ID NOS: 23-24, 27, and 83-86.
7. An antibody-peptide fusion protein, comprising: an amyloid-reactive peptide; and an antibody that binds to human amyloid fibrils, wherein antibody comprises a heavy chain comprising a heavy chain variable region (VH) and a light chain comprising a light chain variable region (VL), wherein the amyloid-reactive peptide and the antibody are linked at the N- and/or C-terminal end of the light chain and/or the N- and/or C-terminal end of the heavy chain, wherein the amyloid-reactive peptide is linked to the antibody via a spacer, wherein the spacer comprises an amino acid sequence selected from the group consisting of SEQ ID NOS: 83-86.
8. The antibody-peptide fusion protein of embodiment 7, wherein the amyloid-reactive peptide and the antibody are linked at the N-terminal end of the light chain or the N-terminal end of the heavy chain.
9. The antibody-peptide fusion protein of embodiment 7, wherein the amyloid-reactive peptide and the antibody are linked at the C-terminal end of the light chain or the C-terminal end of the heavy chain.
10. The antibody-peptide fusion protein of any one of embodiments 7-9, wherein the light chain further comprises a light chain constant region, and the heavy chain comprises a heavy chain constant region.
11. The antibody-peptide fusion protein of any one of embodiments 7-10, wherein the antibody-peptide fusion protein comprises two light chains and two heavy chains.
12. The antibody-peptide fusion protein of any one of the preceding embodiments, wherein the amyloid-reactive peptide comprises an amino acid sequence having at least 85% sequence identity to any one of the amino acid sequences set forth as SEQ ID NOS:1-13.
13. The antibody-peptide fusion protein of any one of the preceding embodiments, wherein the antibody-peptide fusion protein comprises at least two amyloid-reactive peptides and wherein the amyloid-reactive peptides are the same peptide or different peptides.
14. The antibody-peptide fusion protein of any one of the preceding embodiments, wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO:18, and a CDR-H3 comprising the amino acid sequence set forth in SEQ ID NO:19.
15. The antibody-peptide fusion protein of any one of the preceding embodiments, wherein the antibody is a chimeric antibody or humanized antibody.
16. The antibody-peptide fusion protein of embodiments 1-13 and 15, wherein a) the VL comprises a CDR-LT comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO:18, and a CDR-H3 comprising the amino acid sequence set forth in SEQ ID NO:19; b) the VL comprises a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO: 71-81; and a CDR-H3 comprising the amino acid sequence set forth in SEQ ID NO: 19, or c) the VL comprises a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence set forth in SEQ ID NO: 19.
17. The antibody-peptide fusion protein of any one of embodiments 14-16, wherein the VL comprises an amino acid sequence set forth in the group consisting of SEQ ID NOs:32-42.
18. The antibody-peptide fusion protein of any one of embodiments 14-17, wherein the VH comprises an amino acid sequence set forth in the group consisting of SEQ ID NOs:43-63.
19. The antibody-peptide fusion protein of any one of embodiments 14-18, wherein a) the VL comprises an amino acid sequence set forth in SEQ ID NO:34, and the VH comprises an amino acid sequence set forth in SEQ ID NO:48; b) the VL comprises an amino acid sequence set forth in SEQ ID NO:35, and the VH comprises an amino acid sequence set forth in SEQ ID NO:51; c) the VL comprises an amino acid sequence set forth in SEQ ID NO:36, and the VH comprises an amino acid sequence set forth in SEQ ID NO:55; d) the VL comprises an amino acid sequence set forth in SEQ ID NO:35, and the VH comprises an amino acid sequence set forth in SEQ ID NO:52; e) the VL comprises an amino acid sequence set forth in SEQ ID NO:35, and the VH comprises an amino acid sequence set forth in SEQ ID NO:50; or f) the VL comprises an amino acid sequence set forth in SEQ ID NO:35, the V comprises an amino acid sequence set forth in SEQ ID NO:69.
20. The antibody-peptide fusion protein of any one of embodiments 14-19, wherein the VL comprises an amino acid sequence set forth in SEQ ID NO:34, and the VH comprises an amino acid sequence set forth in SEQ ID NO:48.
21. The antibody-peptide fusion protein of any one of embodiments 14-19, wherein the VL comprises an amino acid sequence set forth in SEQ ID NO:35, and the VH comprises an amino acid sequence set forth in SEQ ID NO:51.
22. The antibody-peptide fusion protein of any one of embodiments 14-19, wherein the VL comprises an amino acid sequence set forth in SEQ ID NO:36, and the VH comprises an amino acid sequence set forth in SEQ ID NO:55.
23. The antibody-peptide fusion protein of any one of the preceding embodiments, wherein the antibody is a full-length antibody, a Fab fragment, or a scFv.
24. The antibody-peptide fusion protein of any one of the preceding embodiments, wherein the antibody comprises an Fc region.
25. The antibody-peptide fusion protein of embodiment 24, wherein the Fc region is of an IgG1, IgG2, IgG3, or IgG4 isotype.
26. An antibody-peptide fusion protein, comprising a) a first polypeptide and a second polypeptide comprising an amyloid-reactive peptide linked to the N-terminus of a light chain of an antibody that binds to human amyloid fibrils, and a third and a fourth polypeptide comprising a heavy chain of an antibody that binds to human amyloid fibrils, wherein the first polypeptide and second polypeptide comprise the amino acid set forth in SEQ ID NO:87, and the third and fourth polypeptide comprise the amino acid sequence set forth in SEQ ID NO:91; b) a first polypeptide and a second polypeptide comprising a light chain of an antibody that binds to human amyloid fibrils, and a third and a fourth polypeptide comprising an amyloid-reactive peptide linked to the C-terminus of a heavy chain of an antibody that binds to human amyloid fibrils, wherein the first polypeptide and second polypeptide comprise the amino acid set forth in SEQ ID NO:88, and the third and fourth polypeptide comprise the amino acid sequence set forth in SEQ ID NO:92; c) a first polypeptide and a second polypeptide comprising an amyloid-reactive peptide linked to the C-terminus of a light chain of an antibody that binds to human amyloid fibrils, and a third and a fourth polypeptide comprising a heavy chain of an antibody that binds to human amyloid fibrils, wherein the first polypeptide and second polypeptide comprise the amino acid set forth in SEQ ID NO:89, and the third and fourth polypeptide comprise the amino acid sequence set forth in SEQ ID NO:91; or d) a first polypeptide and a second polypeptide comprising an amyloid-reactive peptide linked to the C-terminus of a light chain of an antibody that binds to a human amyloid fibrils, and a third and a fourth polypeptide comprising a heavy chain of an antibody that binds to human amyloid fibrils, wherein the first polypeptide and second polypeptide comprise the amino acid set forth in SEQ ID NO:90, and the third and fourth polypeptide comprise the amino acid sequence set forth in SEQ ID NO:91.
27. The antibody-peptide fusion protein of any one of the preceding embodiments, wherein the antibody-peptide fusion protein is conjugated to a detectable label.
28. The antibody-peptide fusion protein of any one of the preceding embodiments, wherein the antibody-peptide fusion protein binds to rVλ6Wil, Aβ, Aβ(1-40), IAAP, ALκ4, Alλ1, or ATTR fibrils.
29. A pharmaceutical composition comprising the antibody-peptide fusion protein of any one of embodiments 1-28.
30. Nucleic acid(s) encoding the antibody-peptide fusion protein of any one of embodiments 1-28.
31. A vector comprising the nucleic acid(s) of embodiment 30.
32. A host cell comprising the vector of embodiment 31.
33. The host cell of embodiment 32, wherein the host cell is a mammalian cell, optionally a Chinese hamster ovary (CHO) cell.
34. A method of making an antibody-peptide fusion protein comprising culturing the host cell of embodiment 32 or embodiment 33 under conditions suitable for expression of the vector encoding the antibody-peptide fusion protein.
35. The method of embodiment 34, wherein the method further comprises recovering the antibody-peptide fusion protein.
36. A method of treating a subject having an amyloid related disorder, comprising administering to the subject a therapeutically effective amount of the antibody-peptide fusion protein of any one of embodiments 1-28.
37. The method of embodiment 36, wherein the amyloid related disorder is systematic or localized amyloidosis.
38. The method of embodiment 36, wherein the amyloid related disorder is selected from the group consisting of AL, AH, A02M, ATTR, AA, AApoAI, AApoAII, AGel, ALys, ALECT2, AFib, ACys, ACal, AMed, AIAPP, APro, AIns, APrP, or Aβ amyloidosis.
39. The method of any one of embodiments 36-38, wherein treatment with the antibody-peptide fusion protein results in the clearance of amyloid.
40. The method of any one of embodiments 36-39, wherein the subject is a human.

41. A method of targeting an amyloid deposit for clearance, comprising contacting an amyloid deposit with the antibody-peptide fusion protein of any one of embodiments 1-28.

42. The method of embodiment 41, wherein the amyloid deposit is removed.

43. The method of embodiment 41 or 42, wherein the amyloid deposit is opsonized by the antibody-peptide fusion protein.

44. A method of treating a subject suffering from, or suspected to be suffering from, an amyloid-based disease, comprising a) determining whether the subject has an amyloid deposit by i) administering the antibody-peptide fusion protein of any one of embodiments 1-28 to the subject, wherein the antibody-peptide fusion protein comprises a detectable label, and ii) determining whether a signal associated with the detectable label can be detected from the subject; and b) if the signal is detected, administering to the subject an amyloidosis treatment.

45. The method of embodiment 44, wherein, if a signal is not detected, monitoring the subject for a later development of an amyloid deposit.

46. The method of embodiment 45, further comprising determining the intensity of the signal and comparing the signal to a threshold value, above which the subject is determined to possess an amyloid deposit.

47. The method of any of embodiments 44-46, wherein the amyloidosis treatment comprises administering the antibody-peptide fusion protein of any one of embodiments 1-28 to the subject.

48. The method of embodiment 47, wherein administration of the antibody-peptide fusion protein results in clearance of the amyloid deposit in the subject.

49. A method of identifying an amyloid deposit in a subject, comprising administering the antibody-peptide fusion protein of any one of embodiments 1-28 to the subject, wherein the antibody-peptide fusion protein comprises a detectable label, and detecting a signal from the antibody peptide fusion protein.

50. The method of any of embodiments 44-49, wherein the subject is determined to be amyloid free or suffering from monoclonal gammopathy of unknown significance (MGUS), multiple myeloma (MM), or one or more related plasma cell diseases.

51. A method of detecting a ligand, comprising contacting the ligand with the antibody-peptide fusion protein of any one of embodiments 1-28, wherein the antibody-peptide fusion protein comprises a detectable label, wherein the peptide of the antibody-peptide fusion protein has binding affinity to the ligand and, determining a signal from the detectable label, thereby detecting the ligand.

52. A kit comprising the antibody-peptide fusion protein of any one of embodiments 1-28, for use in the method of any one of embodiments 36-51.

1A. An antibody-peptide fusion protein, comprising:
an amyloid-reactive peptide; and
an antibody capable of inducing phagocytosis and serving as an opsonin, wherein the antibody comprises a heavy chain comprising a heavy chain variable region (VH) and a light chain comprising a light chain variable region (VL), wherein the amyloid-reactive peptide and the antibody are linked at the N-terminal end or the C-terminal end of the heavy chain or the light chain, wherein the amyloid-reactive peptide is linked to the antibody via a spacer comprising an amino acid sequence selected from the group consisting of SEQ ID NOs: 23-24, 27, 83-86.

2A. The antibody-peptide fusion protein of embodiment 1A, wherein the light chain comprises a light chain constant region, and the heavy chain comprises a heavy chain constant region.

3A. The antibody-peptide fusion protein of embodiment 1A or 2A, wherein the amyloid-reactive peptide and the antibody are linked at the C-terminal end of the light chain.

4A. The antibody-peptide fusion protein of embodiment 1A or 2A, wherein the spacer is selected from the group consisting of SEQ ID NO: 83 and SEQ ID NO: 86.

5A. The antibody-peptide fusion protein of any one of embodiments 1A-4A, wherein the amyloid-reactive peptide comprises an amino acid sequence having at least 85%, 90%, 95%, 96%, 97%, 98%, 99%, 99.5%, or 100% sequence identity to any one of the amino acid sequences set forth as SEQ ID NOs: 1-13.

6A. The antibody-peptide fusion protein of any one of embodiments 1A-5A, wherein the antibody-peptide fusion protein comprises two heavy chains and two light chains and wherein each light chain is linked at the C-terminal end to the amyloid-reactive peptide.

7A. The antibody-peptide fusion protein of any one of embodiments 1A-6A, wherein the antibody is a chimeric antibody or humanized antibody.

8A. The antibody-peptide fusion protein of any one of embodiments 1A-7A, wherein the antibody binds to human amyloid fibrils.

9A. The antibody-peptide fusion protein of any one of embodiments 1A-8A, wherein
a) the VL comprises a CDR-L1 comprising the amino acid sequence set forth in SEQ ID NOs: 64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO: 18, and a CDR-H3 comprising the amino acid sequence set forth in SEQ ID NO:19;
b) the VL comprises a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NOs: 71-81; and a CDR-H3 comprising the amino acid sequence set forth in SEQ ID NO: 19; or
c) the VL comprises a CDR-L1 comprising the amino acid sequence set forth in SEQ ID NOs: 64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NOs: 71-81; and a CDR-H3 comprising the amino acid sequence set forth in SEQ ID NO: 19.

10A. The antibody-peptide fusion protein of any one of embodiments 1A-8A, wherein the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO:19.

11A. The antibody-peptide fusion protein of any one of embodiments 1A-8A, wherein:
a) the VL comprises an amino acid sequence set forth in SEQ ID NO:34, and the VH comprises an amino acid sequence set forth in SEQ ID NO:48;
b) the VL comprises an amino acid sequence set forth in SEQ ID NO:35, and the VH comprises an amino acid sequence set forth in SEQ ID NO:51;
c) the VL comprises an amino acid sequence set forth in SEQ ID NO: 36, and the VH comprises an amino acid sequence set forth in SEQ ID NO: 55;
d) the VL comprises an amino acid sequence set forth in SEQ ID NO:35, and the VH comprises an amino acid sequence set forth in SEQ ID NO:52;
e) the VL comprises an amino acid sequence set forth in SEQ ID NO:35, and the VH comprises an amino acid sequence set forth in SEQ ID NO:50; or
f) the VL comprises an amino acid sequence set forth in SEQ ID NO:35, the VH comprises an amino acid sequence set forth in SEQ ID NO:49.

12A. The antibody-peptide fusion protein of any one of embodiments 1A-11A, wherein the VL comprises an amino acid sequence set forth in SEQ ID NO:36, and the VH comprises an amino acid sequence set forth in SEQ ID NO:55.

13A. The antibody-peptide fusion protein of any one of embodiments 1A-12A, wherein the antibody is a full-length antibody.

14A. The antibody-peptide fusion protein of embodiment 13A, wherein the Fc region is of an IgG1 isotype.

15A. An antibody-peptide fusion protein, comprising:
an antibody that binds to amyloid fibrils comprising a first polypeptide and a second polypeptide each comprising a light chain of the antibody, and a third and a fourth polypeptide each comprising a heavy chain of the antibody, and
an amyloid-reactive peptide that is linked to the N-terminus or the C-terminus of the light chain or the heavy chain, wherein
a) the first polypeptide and second polypeptide comprise the amino acid set forth in SEQ ID NO:87, and the third and fourth polypeptide comprise the amino acid sequence set forth in SEQ ID NO:91;
b) the first polypeptide and second polypeptide comprise the amino acid set forth in SEQ ID NO:88, and the third and fourth polypeptide comprise the amino acid sequence set forth in SEQ ID NO:92;
c) the first polypeptide and second polypeptide comprise the amino acid set forth in SEQ ID NO:89, and the third and fourth polypeptide comprise the amino acid sequence set forth in SEQ ID NO:91; or
d) the first polypeptide and second polypeptide comprise the amino acid set forth in SEQ ID NO:90, and the third and fourth polypeptide comprise the amino acid sequence set forth in SEQ ID NO:91.

16A. An antibody-peptide fusion protein, comprising:
an amyloid-reactive peptide comprising the amino acid sequence set forth in SEQ ID NO:1 or SEQ ID NO:2; and
an antibody that binds to a human amyloid fibrils wherein the antibody comprises a variable heavy chain (VH) and a variable light chain (VL) wherein the VH comprises a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO: 19, and the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22; wherein the amyloid-reactive peptide and antibody are linked at the C-terminal end of the light chain, wherein the amyloid-reactive peptide is linked to the antibody via a spacer comprising an amino acid sequence selected from the group consisting of SEQ ID NOs: 23-24, 27, 83-86.

17A. An antibody-peptide fusion protein, comprising:
an amyloid-reactive peptide comprising the amino acid sequence set forth in SEQ ID NO:2; and
an antibody that binds to human amyloid fibrils wherein the antibody comprises a variable heavy chain (VH) and a variable light chain (VL) wherein the VH comprises a CDR-H1 comprising the amino acid sequence set forth in SEQ ID NO: 17, a CDR-H2 comprising the amino acid sequence set forth in SEQ ID NO:73, and a CDR-H3 comprising the amino acid sequence set forth in SEQ ID NO: 19, and the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22; wherein the amyloid-reactive peptide and antibody are linked at the C-terminal end of the light chain, wherein the amyloid-reactive peptide is linked to the antibody via a spacer comprising the amino acid sequence set forth in SEQ ID NO:83.

18A. The antibody-peptide fusion protein of any one of embodiments 1A-17A, wherein the antibody-peptide fusion protein exhibits an EC50 less than 1.5 nM for an amyloid substrate.

19A. The antibody-peptide fusion protein of any one of embodiments 1A-18A, wherein the antibody-peptide fusion protein is conjugated to a detectable label wherein the detectable label comprises a fluorescent label or a radiolabel.

20A. The method of embodiment 19A, wherein the radiolabel is I-123, I-124, F-18, ZR-89, or Tc-99m.

21A. The antibody-peptide fusion protein of any one of embodiments 1A-20A, wherein the antibody-peptide fusion protein exhibits one or more in vivo features selected from among improved biodistribution, pan amyloid reactivity, and enhanced phagocytosis compared to a reference IgG antibody.

22A. The antibody-peptide fusion protein of any one of embodiments 1A-21A, wherein the antibody-peptide fusion protein binds to rVX6Wil, Aβ, Aβ(1-40), IAAP, ALκ4, Alλ1, ATTR, α-synuclein, or Tau 441 fibrils.

23A. A composition comprising
an antibody-peptide fusion protein, comprising:
i) an amyloid-reactive peptide; and
ii) an antibody that is capable of inducing phagocytosis and serving as an opsonin, wherein the antibody comprises a heavy chain comprising a heavy chain variable region (VH) and a light chain comprising a light chain variable region (VL), wherein the amyloid-reactive peptide and antibody are linked at the N-terminal end or the C-terminal end of the heavy chain or the light chain, wherein the amyloid-reactive peptide is linked to the antibody via a spacer, or without a spacer; and
wherein at least 90% of the antibody-peptide fusion protein is intact.

24A. The composition of embodiment 23A, wherein the intact antibody-peptide fusion protein comprises the antibody-peptide fusion protein of any one of embodiments 1A-22A.

25A. The composition of embodiment 23A, wherein the composition comprises no more than 10% of a cleavage product, wherein the cleavage product comprises a heavy chain lacking one or more amino acid residues from the N-terminus or C-terminus compared to the amino acid sequence set forth by SEQ ID NO:89 or a light chain lacking one or more amino acid residues from the N-terminus or C-terminus compared to the amino acid sequence set forth in SEQ ID NO:91.

26A. The composition of any one of embodiments 23A-25A, wherein antibody-peptide fusion protein exhibits an EC50 binding affinity for one or more amyloid substrate, wherein the EC50 binding affinity is less than 1.5 nM.

27A. The composition of any one of embodiments 23A-26A, further comprising a pharmaceutically acceptable carrier.

28A. A polynucleotide encoding the antibody-peptide fusion protein of any one of embodiments 1A-22A.

29A. A vector comprising the polynucleotide of embodiment 28A.

30A. A host cell comprising the vector of embodiment 29A.

31A. The host cell of embodiment 30A, wherein the host cell is a mammalian cell, optionally a Chinese hamster ovary (CHO) cell.

32A. A method of producing an antibody-peptide fusion protein comprising
a) culturing a host cell comprising a vector encoding an antibody-peptide fusion protein under perfusion cell culture conditions suitable for expression of the antibody-peptide fusion protein; and
b) recovering the antibody-peptide fusion protein about every 12-36 hours; wherein the antibody-peptide fusion protein comprises
i) an amyloid-reactive peptide; and
ii) an antibody that is capable of inducing phagocytosis and serving as an opsonin, wherein the antibody comprises a heavy chain comprising a heavy chain variable region (VH) and a light chain comprising a light chain variable region (VL), wherein the amyloid-reactive peptide and antibody are linked at the C-terminal end of the light chain, wherein the amyloid-reactive peptide is linked to the antibody via a spacer, or without a spacer.

33A. The method of embodiment 32A, further comprising applying the antibody-peptide fusion recovered in step b) to a cation exchange chromatography column and eluting the antibody-peptide fusion protein from the cation exchange chromatography column.

34A. The method of embodiment 33A, wherein the antibody-peptide fusion protein is eluted separately from a truncated antibody-peptide fusion protein.

35A. The method of any one of embodiments 32A-34A, wherein the antibody-peptide fusion protein comprises the antibody-peptide fusion protein of any one of embodiments 1A-22A.

36A. The method of any one of embodiments 32A-35A, wherein the host cell is a CHO cell.

37A. The method of any of embodiments 32A-36A, further comprising determining the purity of the antibody-peptide fusion protein, wherein the purity of the antibody-peptide fusion protein is determined using one or more analytical methods comprising sodium dodecyl sulfate capillary electrophoresis (CE-SDS), liquid chromatography (LC), mass spectrometry (MS), or a combination thereof.

38A. The method of any one of embodiments 32A-37A, wherein the antibody-peptide fusion protein is purified to at least 90% intact antibody-peptide fusion protein.

39A. An antibody-peptide fusion protein produced by the method of any of embodiments 32A-38A.

40A. A method of treating a subject having an amyloid related disorder comprising an amyloid deposit, comprising administering to the subject a therapeutically effective amount of the antibody-peptide fusion protein of any one of embodiments 1A-22A and 39A or the composition of any one of embodiments 23A-27A.

41A. The method of embodiment 40A, wherein the amyloid related disorder is systematic or localized amyloidosis.

42A. The method of embodiment 40A or 41A, wherein the amyloid related disorder is selected from the group consisting of AL, AH, Aβ2M, ATTR, transthyretin, AA, AApoAI, AApoAII, AGel, ALys, ALEct2, AFib, ACys, ACal, AMed, AIAPP, APro, AIns, APrP, Parkinson's disease, Alzheimer's disease, or Aβ amyloidosis.

43A. The method of any one of embodiments 40A-42A, wherein the amyloid deposit is opsonized by the antibody-peptide fusion protein.

44A. The method of any one of embodiments 40A-43A, wherein treating the subject with the antibody-peptide fusion protein causes phagocytosis of the amyloid deposit.

45A. A method of treating a subject having an amyloid-based disease or suspected of having an amyloid-based disease, comprising:
a) determining whether the subject has an amyloid deposit by:
i) administering the antibody-peptide fusion protein of any one of embodiments 1A-22A and 39A or the composition of any one of embodiments 23A-27A to the subject, wherein the antibody-peptide fusion protein comprises a detectable label, and
ii) determining whether a signal associated with the detectable label can be detected from the subject; and
b) if the signal is detected, administering to the subject an amyloidosis treatment.

46A. The method of embodiment 45A, wherein, if a signal is not detected, monitoring the subject for a later development of an amyloid deposit.

47A. The method of embodiment 45A or 46A, further comprising determining the intensity of the signal and comparing the signal to a threshold value, above which the subject is determined to possess an amyloid deposit.

48A. The method of any one of embodiments 45A-47A, wherein the antibody-peptide fusion protein is detected by SPECT/CT imaging, PET/CT imagining, gamma scintigraphy, or optical imaging.

49A. The method of any of embodiments 45A-48A, wherein the amyloidosis treatment comprises administering the antibody-peptide fusion protein of any one of embodiments 1A-22A and 39A or the composition of any one of embodiments 23A-27A to the subject.

50A. A method of identifying an amyloid deposit in a subject, comprising administering the antibody-peptide fusion protein of any one of embodiments 1A-22A and 39A or the composition of any one of embodiments 23A-27A, wherein the antibody-peptide fusion protein comprises a detectable label, and detecting a signal from the antibody peptide fusion protein.

51A. A method of monitoring amyloid clearance in a subject comprising
contacting the amyloid substrate in the subject with the antibody-peptide fusion protein of any one of embodiments 1A-22A and 39A or the composition of any one of embodiments 23A-27A, wherein the antibody-peptide fusion protein comprises a detectable label, and wherein the peptide of the antibody-peptide fusion protein has binding affinity for an amyloid substrate; and
determining a signal from the detectable label, thereby detecting the amyloid clearance.

52A. The method of any one of embodiments 40A-51A, wherein the subject is a human.

53A. A kit comprising the antibody-peptide fusion protein of any one of embodiments 1A-22A and 39A or the composition of any one of embodiments 23A-27A, for use in the method of any one of embodiments 40A-52A.

EXEMPLARY SEQUENCES

All polynucleotide sequences are depicted in the 5'→3 direction. All polypeptide sequences are depicted in the N-terminal to C-terminal direction.

```
11-1F4 VH sequence (SEQ ID NO: 15)
QVQLKESGPGLVAPSQSLSITCTVSGFSLSSYGVSWVRQPPGKGLEWLGVIWGDGS
TNYHPNLMSRLSISKDISKSQVLFKLNSLQTDDTATYYCVTLDYWGQGTSVTVSS 11-1F4 VL sequence (SEQ ID NO: 16)
DVVMTQTPLSLPVSLGDQASISCRSSQSLVHRNGNTYLHWYLQKPGQSPKLLIYKV
SNRFSGVPDRFSGSGSGTDFTLKISRVEAEDLGLYFCFQTTYVPNTFGGGTKLEIK 11-1F4 CDR-H1 sequence (SEQ ID NO: 17)
GFSLSSYGVS 11-1F4 CDR-H2 sequence (SEQ ID NO: 18)
VIWGDGSTNYHPNLMS 11-1F4 CDR-H3 sequence (SEQ ID NO: 19)
LDY 11-1F4 CDR-L1 sequence (SEQ ID NO: 20)
RSSQSLVHRNGNTYLH 11-1F4 CDR-L2 sequence (SEQ ID NO: 21)
KVSNRFS 11-1F4 CDR-L3 sequence (SEQ ID NO: 22)
FQTTYVPNT 5' spacer sequence (SEQ ID NO: 23)
AQAGQAGQAQGGGYS 3' spacer sequence (SEQ ID NO: 24)
VTPTV Igp5 light chain construct (SEQ ID NO: 25)
AQAGQAGQAQGGGYSKAQKAQAKQAKQAQKAQKAQAKQAKQVTPTVDVVMTQ
TPLSLPVSLGDQASISCRSSQSLVHRNGNTYLHWYLQKPGQSPKLLIYKVSNRFSGVP
DRFSGSGSGTDFTLKISRVEAEDLGLYFCFQTTYVPNTFGGGTKLEIK p5-3'spacer-11-1F4 VL sequence (SEQ ID NO: 26)
KAQKAQAKQAKQAQKAQKAQAKQAKQVTPTVDVVMTQTPLSLPVSLGDQASISCR
SSQSLVHRNGNTYLHWYLQKPGQSPKLLIYKVSNRFSGVPDRFSGSGSGTDFTLKISR
VEAEDLGLYFCFQTTYVPNTFGGGTKLEIK Linker sequence (SEQ ID NO: 27)
GGGYS IGKV2-30*02-Human germline sequence (SEQ ID NO: 28)
DVVMTQSPLSLPVTLGQPASISCRSSQSLVHSDGNTYLNWFQQRPGQSPRRLIYKVSN
RDSGVPDRFSGSGSGTDFTLKISRVEAEDVGVYYCMQGTHWPP
```

```
Human VL acceptor sequence (SEQ ID NO: 29)
DVVMTQSPLSLPVTLGQPASISCRSSQSLVHSDGNTYLNWFQQRPGQSPRRLIYKVSN
RDSGVPDRFSGSGSGTDFTLKISRVEAEDVGVYYCFQTTYVPNTFGGGTKLEIK IGHV4-4*08-Human germline sequence (SEQ ID NO: 30)
QVQLQESGPGLVKPSETLSLTCTVSGGSISSYYWSWIRQPPGKGLEWIGYIYTSGSTN
YNPSLKSRVTISVDTSKNQFSLKLSSVTAADTAVYYCAR Human VL acceptor sequence (SEQ ID NO: 31)
QVQLQESGPGLVKPSETLSLTCTVSGGSISSYYWSWIRQPPGKGLEWIGYIYTSGSTN
YNPSLKSRVTISVDTSKNQFSLKLSSVTAADTAVYYCARLDYWGQGTSVTVSS VL1 (SEQ ID NO: 32)
DVVMTQSPLSLPVTLGQPASISCRSSQSLVHRNGNTYLHWFQQRPGQSPRRLIYKVS
NRFSGVPDRFSGSGSGTDFTLKISRVEAEDVGVYYCFQTTYVPNTFGGGTKLEIK VL2 (SEQ ID NO: 33)
DVVMTQSPLSLPVTLGQPASISCRSSQSLVHRNGNTYLHWYLQRPGQSPRRLIYKVS
NRFSGVPDRFSGSGSGTDFTLKISRVEAEDVGVYYCFQTTYVPNTFGGGTKLEIK VL3 (SEQ ID NO: 34)
DVVMTQSPLSLPVTLGQPASISCRSSQSLVHRNGNTYLHWYLQRPGQSPRLLIYKVS
NRFSGVPDRFSGSGSGTDFTLKISRVEAEDVGLYFCFQTTYVPNTFGGGTKLEIK VL4 (SEQ ID NO: 35)
DVVMTQSPLSLPVTLGQPASISCRSSQSLVHRNGNTYLHWFQQRPGQSPRLLIYKVS
NRFSGVPDRFSGSGSGTDFTLKISRVEAEDVGVYFCFQTTYVPNTFGGGTKLEIK VL4-N33S (SEQ ID NO: 36)
DVVMTQSPLSLPVTLGQPASISCRSSQSLVHRSGNTYLHWFQQRPGQSPRLLIYKVSN
RFSGVPDRFSGSGSGTDFTLKISRVEAEDVGVYFCFQTTYVPNTFGGGTKLEIK VL4-N33Q (SEQ ID NO: 37)
DVVMTQSPLSLPVTLGQPASISCRSSQSLVHRQGNTYLHWFQQRPGQSPRLLIYKVS
NRFSGVPDRFSGSGSGTDFTLKISRVEAEDVGVYFCFQTTYVPNTFGGGTKLEIK VL4-N33E (SEQ ID NO: 38)
DVVMTQSPLSLPVTLGQPASISCRSSQSLVHREGNTYLHWFQQRPGQSPRLLIYKVSN
RFSGVPDRFSGSGSGTDFTLKISRVEAEDVGVYFCFQTTYVPNTFGGGTKLEIK VL4-N33A (SEQ ID NO: 39)
DVVMTQSPLSLPVTLGQPASISCRSSQSLVHRAGNTYLHWFQQRPGQSPRLLIYKVS
NRFSGVPDRFSGSGSGTDFTLKISRVEAEDVGVYFCFQTTYVPNTFGGGTKLEIK VL4-N33H (SEQ ID NO: 40)
DVVMTQSPLSLPVTLGQPASISCRSSQSLVHRHGNTYLHWFQQRPGQSPRLLIYKVS
NRFSGVPDRFSGSGSGTDFTLKISRVEAEDVGVYFCFQTTYVPNTFGGGTKLEIK VL4-G34A (SEQ ID NO: 41)
DVVMTQSPLSLPVTLGQPASISCRSSQSLVHRAGNTYLHWFQQRPGQSPRLLIYKVS
NRFSGVPDRFSGSGSGTDFTLKISRVEAEDVGVYFCFQTTYVPNTFGGGTKLEIK VL4-G34V (SEQ ID NO: 42)
DVVMTQSPLSLPVTLGQPASISCRSSQSLVHRVGNTYLHWFQQRPGQSPRLLIYKVS
NRFSGVPDRFSGSGSGTDFTLKISRVEAEDVGVYFCFQTTYVPNTFGGGTKLEIK VH1 (SEQ ID NO: 43)
QVQLQESGPGLVKPSETLSLTCTVSGFSLSSYGVSWIRQPPGKGLEWIGVIWGDGSTN
YHPNLMSRVTISVDTSKNQFSLKLSSVTAADTAVYYCARLDYWGQGTSVTVSS VH2 (SEQ ID NO: 44)
QVQLQESGPGLVKPSETLSLTCTVSGFSLSSYGVSWVRQPPGKGLEWLGVIWGDGST
NYHPNLMSRVTISVDTSKNQFSLKLSSVTAADTAVYYCARLDYWGQGTSVTVSS VH3 (SEQ ID NO: 45)
QVQLQESGPGLVKPSETLSLTCTVSGFSLSSYGVSWIRQPPGKGLEWIGVIWGDGSTN
YHPNLMSRLSISVDTSKNQFSLKLSSVTAADTATYYCVTLDYWGQGTSVTVSS VH4 (SEQ ID NO: 46)
QVQLQESGPGLVKPSETLSLTCTVSGFSLSSYGVSWVRQPPGKGLEWLGVIWGDGST
NYHPNLMSRLSISVDTSKNQFSLKLSSVTAADTAVYYCARLDYWGQGTSVTVSS VH5 (SEQ ID NO: 47)
QVQLQESGPGLVKPSETLSLTCTVSGFSLSSYGVSWVRQPPGKGLEWLGVIWGDGST
NYHPNLMSRLSISVDTSKNQFSLKLSSVTAADTAVYYCVTLDYWGQGTSVTVSS VH6 (SEQ ID NO: 48)
QVQLQESGPGLVKPSETLSLTCTVSGFSLSSYGVSWVRQPPGKGLEWLGVIWGDGST
NYHPNLMSRLSISKDTSKNQFSLKLSSVTAADTATYYCVTLDYWGQGTSVTVSS
```

```
VH7 (SEQ ID NO: 49)
QVQLQESGPGLVKPSETLSLTCTVSGFSLSSYGVSWIRQPPGKGLEWIGVIWGDGSTN
YHPNLMSRVTISKDTSKNQVLLKLSSVTAADTAVYYCVTLDYWGQGTSVTVSS

VH8 (SEQ ID NO: 50)
QVQLQESGPGLVKPSETLSLTCTVSGFSLSSYGVSWIRQPPGKGLEWIGVIWGDGSTN
YHPNLMSRVTISKDTSKSQFSLKLSSVTAADTAVYYCVTLDYWGQGTSVTVSS

VH9 (SEQ ID NO: 51)
QVQLQESGPGLVKPSETLSLTCTVSGFSLSSYGVSWIRQPPGKGLEWLGVIWGDGST
NYHPNLMSRVTISVDTSKSQVLFKLSSVTAADTAVYYCATLDYWGQGTSVTVSS

VH10 (SEQ ID NO: 52)
QVQLQESGPGLVKPSETLSLTCTVSGFSLSSYGVSWIRQPPGKGLEWLGVIWGDGST
NYHPNLMSRLSISKDTSKSQVLLKLSSVTAADTAVYYCVTLDYWGQGTSVTVSS

VH9-D54S (SEQ ID NO: 53)
QVQLQESGPGLVKPSETLSLTCTVSGFSLSSYGVSWIRQPPGKGLEWLGVIWGSGST
NYHPNLMSRVTISVDTSKSQVLFKLSSVTAADTAVYYCATLDYWGQGTSVTVSS

VH9-D54Q (SEQ ID NO: 54)
QVQLQESGPGLVKPSETLSLTCTVSGFSLSSYGVSWIRQPPGKGLEWLGVIWGQGST
NYHPNLMSRVTISVDTSKSQVLFKLSSVTAADTAVYYCATLDYWGQGTSVTVSS

VH9-D54E (SEQ ID NO: 55)
QVQLQESGPGLVKPSETLSLTCTVSGFSLSSYGVSWIRQPPGKGLEWLGVIWGEGST
NYHPNLMSRVTISVDTSKSQVLFKLSSVTAADTAVYYCATLDYWGQGTSVTVSS

VH9-D54A (SEQ ID NO: 56)
QVQLQESGPGLVKPSETLSLTCTVSGFSLSSYGVSWIRQPPGKGLEWLGVIWGAGST
NYHPNLMSRVTISVDTSKSQVLFKLSSVTAADTAVYYCATLDYWGQGTSVTVSS

VH9-D54H (SEQ ID NO: 57)
QVQLQESGPGLVKPSETLSLTCTVSGFSLSSYGVSWIRQPPGKGLEWLGVIWGHGST
NYHPNLMSRVTISVDTSKSQVLFKLSSVTAADTAVYYCATLDYWGQGTSVTVSS

VH9-G55A (SEQ ID NO: 58)
QVQLQESGPGLVKPSETLSLTCTVSGFSLSSYGVSWIRQPPGKGLEWLGVIWGDAST
NYHPNLMSRVTISVDTSKSQVLFKLSSVTAADTAVYYCATLDYWGQGTSVTVSS

VH9-G55V (SEQ ID NO: 59)
QVQLQESGPGLVKPSETLSLTCTVSGFSLSSYGVSWIRQPPGKGLEWLGVIWGDVST
NYHPNLMSRVTISVDTSKSQVLFKLSSVTAADTAVYYCATLDYWGQGTSVTVSS

VH9-M64V (SEQ ID NO: 60)
QVQLQESGPGLVKPSETLSLTCTVSGFSLSSYGVSWIRQPPGKGLEWLGVIWGDGST
NYHPNLVSRVTISVDTSKSQVLFKLSSVTAADTAVYYCATLDYWGQGTSVTVSS

VH9-M64I (SEQ ID NO: 61)
QVQLQESGPGLVKPSETLSLTCTVSGFSLSSYGVSWIRQPPGKGLEWLGVIWGDGST
NYHPNLISRVTISVDTSKSQVLFKLSSVTAADTAVYYCATLDYWGQGTSVTVSS

VH9-M64L (SEQ ID NO: 62)
QVQLQESGPGLVKPSETLSLTCTVSGFSLSSYGVSWIRQPPGKGLEWLGVIWGDGST
NYHPNLLSRVTISVDTSKSQVLFKLSSVTAADTAVYYCATLDYWGQGTSVTVSS

VH9-M64A (SEQ ID NO: 63)
QVQLQESGPGLVKPSETLSLTCTVSGFSLSSYGVSWIRQPPGKGLEWLGVIWGDGST
NYHPNLASRVTISVDTSKSQVLFKLSSVTAADTAVYYCATLDYWGQGTSVTVSS

VL4-N33S CDR-L1 (SEQ ID NO: 64)
RSSQSLVHRSGNTYLH

VL4-N33Q CDR-L1 (SEQ ID NO: 65)
RSSQSLVHRQGNTYLH

VL4-N33E CDR-L1 (SEQ ID NO: 66)
RSSQSLVHREGNTYLH

VL4-N33A CDR-L1 (SEQ ID NO: 67)
RSSQSLVHRAGNTYLH

VL4-N33H CDR-L1 (SEQ ID NO: 68)
RSSQSLVHRHGNTYLH

VL4-G34A CDR-L1 (SEQ ID NO: 69)
RSSQSLVHRNANTYLH
```

```
VL4-G34V CDR-L1 (SEQ ID NO: 70)
RSSQSLVHRNVNTYLH

VH9-D54S CDR-H2 (SEQ ID NO: 71)
VIWGSGSTNYHPNLMS

VH9-D54Q CDR-H2 (SEQ ID NO: 72)
VIWGQGSTNYHPNLMS

VH9-D54E CDR-H2 (SEQ ID NO: 73)
VIWGEGSTNYHPNLMS

VH9-D54A CDR-H2 (SEQ ID NO: 74)
VIWGAGSTNYHPNLMS

VH9-D54H CDR-H2 (SEQ ID NO: 75)
VIWGHGSTNYHPNLMS

VH9-G55A CDR-H2 (SEQ ID NO: 76)
VIWGDASTNYHPNLMS

VH9-G55V CDR-H2 (SEQ ID NO: 77)
VIWGDVSTNYHPNLMS

VH9-M64V CDR-H2 (SEQ ID NO: 78)
VIWGDGSTNYHPNLVS

VH9-M64I CDR-H2 (SEQ ID NO: 79)
VIWGDGSTNYHPNLIS

VH9-M64L CDR-H2 (SEQ ID NO: 80)
VIWGDGSTNYHPNLLS

VH9-M64A CDR-H2 (SEQ ID NO: 81)
VIWGDGSTNYHPNLAS

N-terminus of Ig light chain (SEQ ID NO: 82)
DVVMTQTP

Short, rigid spacer (SEQ ID NO: 83)
VSPSV

Long, rigid spacer (SEQ ID NO: 84)
VSPSVVSPSV

Short, flexible spacer (SEQ ID NO: 85)
GGSGG

Long, flexible spacer (SEQ ID NO: 86)
GGGGSGGGGS
```

We claim:

1. An antibody-peptide fusion protein, comprising:

an antibody that binds to human amyloid fibrils comprising i) a heavy chain and ii) a light chain with an amyloid-reactive peptide fused to the C-terminus of the light chain via a linker, wherein the heavy chain comprises the amino acid sequence of SEQ ID NO:91, and the light chain with the amyloid-reactive peptide fused to the C-terminus of the light chain via the linker comprises the amino acid sequence of SEQ ID NO:89.

2. A pharmaceutical composition comprising the antibody-peptide fusion protein of claim 1 and a pharmaceutical acceptable carrier.

3. A polynucleotide encoding an antibody-peptide fusion protein comprising:

an antibody that binds to human amyloid fibrils comprising i) a heavy chain and ii) a light chain with an amyloid-reactive peptide fused to the C-terminus of the light chain via a linker, wherein the heavy chain comprises the amino acid sequence of SEQ ID NO:91, and the light chain with the amyloid-reactive peptide fused to the C-terminus of the light chain via the linker comprises the amino acid sequence of SEQ ID NO:89.

4. A vector comprising the polynucleotide of claim 3.

5. A host cell comprising the vector of claim 4.

6. An antibody-peptide fusion protein that binds to human amyloid fibrils produced by a method comprising:

a) culturing a host cell comprising a vector encoding the antibody-peptide fusion protein under perfusion cell culture conditions suitable for expression of the antibody-peptide fusion protein, wherein the antibody-peptide fusion protein comprises an antibody that binds to human amyloid fibrils comprising i) a heavy chain and ii) a light chain with an amyloid-reactive peptide fused to the C-terminus of the light chain via a linker, wherein the heavy chain comprises the amino acid sequence of SEQ ID NO:91, and the light chain with the amyloid-reactive peptide fused to the C-terminus of the light chain via a linker comprises the amino acid sequence of SEQ ID NO: 89; and b) recovering the antibody-peptide fusion protein produced by the host cell.

7. The antibody-peptide fusion protein of claim 6, wherein the method comprises recovering the antibody-peptide fusion protein about every 12-36 hours.

8. The antibody-peptide fusion protein of claim 6, wherein the host cell is a Chinese hamster ovary (CHO) cell.

9. An antibody-peptide fusion protein that bind to human amyloid fibrils, wherein the fusion protein comprises a first polypeptide, a second polypeptide, a third polypeptide, and a fourth polypeptide, wherein the first polypeptide and the second polypeptide each comprise the amino acid sequence set forth in SEQ ID NO:89, and the third polypeptide and the fourth polypeptide each comprise the amino acid sequence set forth in SEQ ID NO:91.

* * * * *